(12) United States Patent
Lee et al.

(10) Patent No.: US 11,319,556 B2
(45) Date of Patent: May 3, 2022

(54) YEAST STRAIN WITH GLUCOSE AND XYLOSE CO-UTILIZATION CAPACITY

(71) Applicant: KOREA INSTITUTE OF SCIENCE AND TECHNOLOGY, Seoul (KR)

(72) Inventors: Sun Mi Lee, Seoul (KR); Phuong Nguyen Hoang Tran, Seoul (KR); Youngsoon Um, Seoul (KR); Gyeongtaek Gong, Seoul (KR); Ja Kyong Ko, Seoul (KR); Yeonjung Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 198 days.

(21) Appl. No.: 16/551,335

(22) Filed: Aug. 26, 2019

(65) Prior Publication Data
US 2020/0149071 A1    May 14, 2020

(30) Foreign Application Priority Data

Nov. 8, 2018  (KR) .......... 10-2018-0136647
May 27, 2019  (KR) .......... 10-2019-0061921

(51) Int. Cl.
| | |
|---|---|
| C12N 15/90 | (2006.01) |
| C12N 1/16 | (2006.01) |
| C12N 15/81 | (2006.01) |
| C12P 7/06 | (2006.01) |
| C12P 7/16 | (2006.01) |
| C12N 9/04 | (2006.01) |
| C12N 9/02 | (2006.01) |
| C12N 9/10 | (2006.01) |
| C12N 9/12 | (2006.01) |
| C12N 9/92 | (2006.01) |
| C12N 15/11 | (2006.01) |
| C12N 9/22 | (2006.01) |

(52) U.S. Cl.
CPC ............ *C12N 15/905* (2013.01); *C12N 1/16* (2013.01); *C12N 9/001* (2013.01); *C12N 9/0006* (2013.01); *C12N 9/0008* (2013.01); *C12N 9/1022* (2013.01); *C12N 9/1029* (2013.01); *C12N 9/1205* (2013.01); *C12N 9/22* (2013.01); *C12N 9/92* (2013.01); *C12N 15/11* (2013.01); *C12N 15/81* (2013.01); *C12P 7/06* (2013.01); *C12Y 101/01157* (2013.01); *C12Y 102/01057* (2013.01); *C12Y 202/01002* (2013.01); *C12Y 203/01009* (2013.01); *C12Y 207/01017* (2013.01); *C12Y 503/01005* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 9,790,511 B2 | 10/2017 | Desfougeres et al. | |
| 2010/0129885 A1* | 5/2010 | Khramtsov | C12P 7/16 435/160 |

FOREIGN PATENT DOCUMENTS

| | | |
|---|---|---|
| JP | 2014-512818 A | 5/2014 |
| JP | 2015-532107 A | 11/2015 |
| WO | WO 2012/143513 A2 | 10/2012 |

OTHER PUBLICATIONS

Feng, X., et al. 2013 Biotechnology for Biofuels 6:96 (17 pages). (Year: 2013).*
Hoffmann, B., et al. 1999 Molecular Microbiology 31(3): 804-822. (Year: 1999).*
DiCarlo, J.E., et al. 2013 Nucleic Acids Research 41(7): 4336-4343. (Year: 2013).*
Genbank Accession No. EF058916.1, 2007.
Genbank Accession No. M25488.1, 1994.
Lee et al., "Systematic and evolutionary engineering of a xylose isomerase-based pathway in *Saccharomyces cerevisiae* for efficient conversion yields", Biotechnology for Biofuels, vol. 7, 8 pages, 2014.
Verhoeven et al., "Mutations in PMR1 stimulate xylose isomerase activity and anaerobic growth on xylose of engineered *Saccharomyces cerevisiae* by influencing manganese homeostasis", Scientific Reports, Apr. 12, 2017, 11 pages.

* cited by examiner

*Primary Examiner* — Marsha Tsay
(74) *Attorney, Agent, or Firm* — Birch, Stewart, Kolasch & Birch, LLP

(57) ABSTRACT

The present specification relates to a transformed yeast strain capable of simultaneously utilizing xylose and glucose as carbon sources, a preparation method thereof and a biofuel production method using the same. The transformed yeast strain transforms a wild-type yeast strain incapable of using xylose as a carbon source and simultaneously convert glucose and xylose, thereby enabling high yield production of a biofuel. The economics and sustainability of the biofuel and biomaterial production processes can be highly enhanced by providing a strain which can easily be converted to a strain capable of producing a biofuel/material in a high yield through an additional modification.

19 Claims, 11 Drawing Sheets
Specification includes a Sequence Listing.

O— Wild-type *ASC1*-expressed strain (Comparative Example 3)

●— *ASC1*$^{Q237*}$-expressed strain (Example 4)

O··· *ASC1*-deficient strain (Example 3)

SEQUENCE LISTING

<160> NUMBER OF SEQ ID NOS: 25

<210> SEQ ID NO 1
<211> LENGTH: 2853
<212> TYPE: DNA
<213> ORGANISM: Artificial Sequence
<220> FEATURE:
<223> OTHER INFORMATION: Synthetic: PMR1

<400> SEQUENCE: 1

| | | | | | |
|---|---|---|---|---|---|
| atgagtgaca | atccatttaa | tgcgagtctt | cttgacgagg | actcaaaccg | tgagagagaa | 60 |
| atactagatg | ccacagcaga | ggcccttccg | aaaccaagcc | cttctttaga | gtattgtact | 120 |
| ttatccgtgg | acgaagctct | agaaaaactg | gacactgaca | aaaacggtgg | tttacgatca | 180 |
| tctaacgagg | ccaacaatag | gagatcactt | tatggcccca | atgaaataac | cgtagaagat | 240 |
| gatgaaagtc | ttttcaagaa | gttcttgtca | aatttcattg | aggatcgaat | gattctactt | 300 |
| ttaataggat | ccgcagtggt | ctctctttt | atgggtaaca | ttgatgatgc | tgttagtatc | 360 |
| acactggcca | ttttcatagt | tgtcactgtc | ggttttgtcc | aagaatatag | gtctgaaaaa | 420 |
| tctctagaag | cgttgaataa | attggttcct | gctgaatgtc | acttaatgag | atgtggtcaa | 480 |
| gagagtcatg | tactggcttc | caccttggtt | cctggtgatt | tagtgcactt | cagaataggt | 540 |
| gacagaatcc | ccgcagacat | tagaattatt | gaagcaatcg | atttatccat | cgatgaaagt | 600 |
| aatttaactg | gtgaaaatga | accggtacat | aaaacctcac | aaacgatcga | aaatcttcc | 660 |
| tttaacgatc | agcctaattc | aattgtaccg | atttctgaga | gatcttgtat | agcttatatg | 720 |
| ggtacattag | tcaaggaagg | tcatggtaag | ggtatcgtcg | taggaacagg | tacaaacaca | 780 |
| tcctttggtg | ccgtttttga | aatgatgaat | aatattgaaa | aaccgaagac | tccattgcag | 840 |
| ttaacaatgg | acaaattggg | aaaggacttg | tcactggtta | gcttcatagt | tattggtatg | 900 |
| atttgtttag | ttggtatcat | acaaggtaga | tcttggttag | aaatgttcca | atatcggta | 960 |
| tccttagcgg | ttgctgctat | tccagaaggg | ttaccaatta | ttgtcactgt | tactttggca | 1020 |
| ttgggtgttc | tgagaatggc | caagcgtaaa | gccatcgtga | aaggttacc | aagtgtcgaa | 1080 |
| actttaggct | ctgtcaacgt | tatctgctcc | gacaaaacag | gtacactaac | ctcaaaccac | 1140 |
| atgaccgtat | ctaaactttg | gtgcttggac | agtatgtcca | ataagctaaa | cgtcctctca | 1200 |
| ttagacaaaa | ataagaagac | taaaaattct | aatggaaatt | tgaaaaacta | tttgactgaa | 1260 |
| gacgttaggg | aaactctaac | tatcggtaat | ctctgtaata | atgcatcttt | ctctcaagaa | 1320 |
| catgccatat | ttctgggaaa | tcctactgat | gtagctcttt | tagagcaatt | ggcaaacttt | 1380 |
| gaaatgcctg | atatcagaaa | caccgttcaa | aaagttcagg | aacttccatt | taactcgaaa | 1440 |
| agaaaattaa | tggcaaccaa | gattctcaac | cctgtcgaca | ataagtgtac | agtttatgtt | 1500 |
| aaaggtgcat | ttgaaagaat | tcttgagtac | tccacaagtt | atttgaaatc | aaagggtaaa | 1560 |
| aaaactgaaa | agttgactga | agcccaaaaa | gctacgaata | atgagtgcgc | aaattctatg | 1620 |
| gcatctgaag | gtttgcgtgt | ctttggattt | gctaaactaa | ctttgtctga | ttcatcaact | 1680 |
| cctctaaccg | aagacctaat | caaagattta | accttactg | gtttaatcgg | tatgaatgac | 1740 |
| ccaccaagac | cgaacgttaa | atttgccatc | gaacaattac | tacaaggtgg | tgtccatatt | 1800 |
| attatgatca | ctggtgattc | tgagaatacc | gcagtaaaca | ttgcaaaaca | aattggtatt | 1860 |
| ccagttattg | atccaaagct | ttccgtttta | tccggtgata | aattagatga | aatgtcagat | 1920 |
| gatcaactgg | ccaatgtcat | cgaccacgtt | aatattttg | ctcgtgctac | gcctgagcat | 1980 |
| aagttaaaca | ttgttcgtgc | attaagaaag | agggtgatg | tggtagcaat | gactggtgat | 2040 |

-continued

```
ggtgttaacg acgctcctgc gttgaaactt tcagatattg gtgtttctat gggtagaatt    2100
ggtacagatg tagccaaaga agcctcgat atggtcttaa ctgatgatga cttcagtact     2160
attttaactg ccattgaaga gggtaaaggt atctttaata atattcagaa tttcctgact   2220
tttcaattgt ctacttctgt tgccgcacta tcattagttg cactatctac agcgtttaaa   2280
ctacccaatc cactgaacgc aatgcaaatt ctttggataa atattttaat ggatgggcca   2340
ccagctcaat ccttaggtgt ggaacctgtt gatcatgaag ttatgaaaaa acctccaaga   2400
aaacgtaccg ataaaatttt gacccatgat gtaatgaaac gtttactaac caccgcggcc   2460
tgtatcatcg ttgggacagt ttacattttt gttaaagaga tggccgaaga tggtaaagta   2520
actgctagag atactactat gacatttact tgttttgttt ttttgatat gtttaatgct    2580
ttggcctgca gacataacac aaagtcaatc ttcgaaatcg gcttttcac gaacaaaatg    2640
ttcaactacg ccgttggact gtctctgtta ggtcaaatgt gcgctatata tataccattt   2700
ttccaaagta tctttaaaac tgagaaactt ggtatctctg atatactatt gttattgctc   2760
atcagcagta gcgttttcat cgttgatgaa ttgagaaaat tgtggacgag aaaaagaat    2820
gaagaagact caacgtattt ctcaaatgtt tga                               2853
```

<210> SEQ ID NO 2
<211> LENGTH: 2853
<212> TYPE: DNA
<213> ORGANISM: Artificial Sequence
<220> FEATURE:
<223> OTHER INFORMATION: Synthetic: PMR1 mutant

<400> SEQUENCE: 2

```
atgagtgaca atccatttaa tgcgagtctt cttgacgagg actcaaaccg tgagagagaa     60
atactagatg ccacagcaga ggcccttcg aaaccaagcc cttctttaga gtattgtact    120
ttatccgtgg acgaagctct agaaaaactg gacactgaca aaaacggtgg tttacgatca   180
tctaacgagg ccaacaatag gagatcactt tatggcccca atgaaataac cgtagaagat   240
gatgaaagtc ttttcaagaa gttcttgtca aatttcattg aggatcgaat gattctactt    300
ttaataggat ccgcagtggt ctctcttttt atgggtaaca ttgatgatgc tgttagtatc   360
acactggcca ttttcatagt tgtcactgtc ggttttgtcc aagaatatag gtctgaaaaa   420
tctctagaag cgttgaataa attggttcct gctgaatgtc acttaatgag atgtggtcaa   480
gagagtcatg tactggcttc caccttggtt cctggtgatt tagtgcactt cagaataggt   540
gacagaatcc ccgcagacat tagaattatt gaagcaatcg atttatccat cgatgaaagt   600
aatttaactg gtgaaaatga accggtacat aaaacctcac aaacgatcga aaaatcttcc   660
tttaacgatc agcctaattc aattgtaccg atttctgaga atcttgtat agcttatatg    720
ggtacattag tcaaggaagg tcatggtaag ggtatcgtcg taggaacagg tacaaacaca   780
tccttggtg ccgtttttga aatgatgaat aatattgaaa aaccgaagac tccattgcag    840
ttaacaatgg acaaattggg aaaggacttg tcactggtta gcttcatagt tattggtatg   900
atttgtttag ttggtatcat acaaggtaga tcttggttag aaatgttcca aatatcggta   960
tccttagcgg ttgctgctat tccagaaggg ttaccaatta ttgtcactgt tacttttggca  1020
ttgggtgttc tgagaatggc caagcgtaaa gccatcgtga aaggttacc aagtgtcgaa    1080
actttaggct ctgtcaacgt tatctgctcc gacaaaacag gtacactaac ctcaaaccac  1140
atgaccgtat ctaaactttg gtgcttggac agtatgtcca ataagctaaa cgtcctctca  1200
```

```
ttagacaaaa ataagaagac taaaaattct aatggaaatt tgaaaaacta tttgactgaa    1260
gacgttaggg aaactctaac tatcggtaat ctctgtaata atgcatcttt ctctcaagaa    1320
catgccatat ttctgggaaa tcctactgat gtagctcttt tagagcaatt ggcaaacttt    1380
gaaatgcctg atatcagaaa caccgttcaa aaagttcagg aacttccatt taactcgaaa    1440
agaaaattaa tggcaaccaa gattctcaac cctgtcgaca ataagtgtac agtttatgtt    1500
aaaggtgcat ttgaaagaat tcttgagtac tccacaagtt atttgaaatc aaagggtaaa    1560
aaaactgaaa agttgactga agcccaaaaa gctacgataa atgagtgcgc aaattctatg    1620
gcatctgaag gtttgcgtgt ctttggattt gctaaactaa ctttgtctga ttcatcaact    1680
cctctaaccg aagacctaat caaagattta acctttactg gtttaatcgg tatgaatgac    1740
ccaccaagac cgaacgttaa atttgccatc gaacaattac tacaaggtgg tgtccatatt    1800
attatgatca ctggtgattc tgagaatacc gcagtaaaca ttgcaaaaca aattggtatt    1860
ccagttattg atccaaagct ttccgtttta tccggtgata aattagatga aatgtcagat    1920
gatcaactgg ccaatgtcat cgaccacgtt aatattttg ctcgtgctac gcctgagcat    1980
aagttaaaca ttgttcgtgc attaagaaag aggggtgatg tggtagcaat gactggtgat    2040
gatgttaacg acgctcctgc gttgaaactt tcagatattg tgtttctat gggtagaatt    2100 ggtacagatg tagccaaaga agcctcagat atggtcttaa ctgatgatga cttcagtact    2160
attttaactg ccattgaaga gggtaaaggt atctttaata atattcagaa tttcctgact    2220
tttcaattgt ctacttctgt tgccgcacta tcattagttg cactatctac agcgtttaaa    2280
ctacccaatc cactgaacgc aatgcaaatt ctttggataa atattttaat ggatgggcca    2340
ccagctcaat ccttaggtgt ggaacctgtt gatcatgaag ttatgaaaaa acctccaaga    2400
aaacgtaccg ataaaatttt gacccatgat gtaatgaaac gtttactaac caccgcggcc    2460
tgtatcatcg ttgggacagt ttacattttt gttaaagaga tggccgaaga tggtaaagta    2520
actgctagag atactactat gacatttact tgttttgttt tttttgatat gtttaatgct    2580
ttggcctgca gacataacac aaagtcaatc ttcgaaatcg gcttttcac gaacaaaatg    2640 ttcaactacg ccgttggact gtctctgtta ggtcaaatgt gcgctatata tataccattt    2700
ttccaaagta tctttaaaac tgagaaactt ggtatctctg atatactatt gttattgctc    2760
atcagcagta gcgttttcat cgttgatgaa ttgagaaaat tgtggacgag gaaaaagaat    2820
gaagaagact caacgtattt ctcaaatgtt tga                                 2853

<210> SEQ ID NO 3
<211> LENGTH: 1233
<212> TYPE: DNA
<213> ORGANISM: Artificial Sequence
<220> FEATURE:
<223> OTHER INFORMATION: Synthetic: ASC1

<400> SEQUENCE: 3
atggcatcta acgaagtttt agttttgaga ggtaccttgg aaggtcacaa cggttgggtc      60
acatctttgg ctacttctgc tggtcaacca aacctattgt tgtccgcttc ccgtgataag     120
actttgatct cctggaagtt gactggtgac gaccaaaagt ttggtgtccc agttagatct     180
ttcaagggtc acagtcacat tgtccaagac tgtactttga ctgctgacgg tgcttacgct     240
ttgtctgctt cttgggacaa gaccttgaga ttatgggatg ttgccaccgg tgaaacctac     300
caaagattcg tcggtcacaa gtccgatgtt atgtccgttg acattgacaa gaaggcttcc     360
atgattatct ctggttcccg tgacaagacc atcaaggtct ggaccatcaa aggtcaatgt     420
```

```
ttggccactt tgttgggtca caatgactgg gtttcccaag tcagagttgt tccaaacgaa    480
aaagctgatg atgactctgt caccatcatt tctgccggta acgacaaaat ggttaaggta    540
tgtgatatat tttctttcca tgatagaata tgatgacaat cgagtagaag aagaaaagtg    600
gatttgtgta tgccattcaa atgatgtaat aacatatttg ctacttcaga tggaactttg    660
agttccgaat gagacatacc aattatcacc aagatctctg atgaatggtt tagcattact    720
ctgctcttct ctttactcgt tatgtcaaaa tggaaacttt tttttaaat taattttgtt     780 cccttactaa caaaaatgat ataatgacag gcttggaact taaaccaatt ccaaattgaa    840
gctgacttca tcggtcacaa ctccaacatc aacactttga ctgcttcccc agacggaact    900
ttgattgctt ccgctggtaa ggacggtgaa attatgttgt ggaacttggc tgctaagaag    960
gctatgtaca ctttgtctgc caagatgaa gttttctctt tggctttctc tccaaacaga     1020
tactggttgg ctgctgccac tgctaccggt attaaggtct tttctttgga cccacaatac    1080
ttggtcgatg acttgagacc agaatttgct ggttacagca aggccgctga accacatgct    1140
gtttctttgg cttggtctgc tgacggtcaa actttgtttg ccggttacac cgacaacgtc    1200
attagagttt ggcaagttat gactgctaac taa                                 1233

<210> SEQ ID NO 4
<211> LENGTH: 1233
<212> TYPE: DNA
<213> ORGANISM: Artificial Sequence
<220> FEATURE:
<223> OTHER INFORMATION: Synthetic:  ASC1 mutant

<400> SEQUENCE: 4
atggcatcta acgaagtttt agttttgaga ggtaccttgg aaggtcacaa cggttgggtc     60
acatctttgg ctacttctgc tggtcaacca aacctattgt tgtccgcttc ccgtgataag    120
actttgatct cctggaagtt gactggtgac gaccaaaagt ttggtgtccc agttagatct    180
ttcaagggtc acagtcacat tgtccaagac tgtactttga ctgctgacgg tgcttacgct    240
ttgtctgctt cttgggacaa gaccttgaga ttatgggatg ttgccaccgg tgaaacctac    300
caaagattcg tcggtcacaa gtccgatgtt atgtccgttg acattgacaa gaaggcttcc    360
atgattatct ctggttcccg tgacaagacc atcaaggtct ggaccatcaa aggtcaatgt    420
ttggccactt tgttgggtca caatgactgg gtttcccaag tcagagttgt tccaaacgaa    480
aaagctgatg atgactctgt caccatcatt tctgccggta acgacaaaat ggttaaggta    540
tgtgatatat tttctttcca tgatagaata tgatgacaat cgagtagaag aagaaaagtg    600
gatttgtgta tgccattcaa atgatgtaat aacatatttg ctacttcaga tggaactttg    660
agttccgaat gagacatacc aattatcacc aagatctctg atgaatggtt tagcattact    720
ctgctcttct ctttactcgt tatgtcaaaa tggaaacttt tttttaaat taattttgtt     780 cccttactaa caaaaatgat ataatgacag gcttggaact taaaccaatt ccaaattgaa    840
gctgacttca tcggtcacaa ctccaacatc aacactttga ctgcttcccc agacggaact    900
ttgattgctt ccgctggtaa ggacggtgaa attatgttgt ggaacttggc tgctaagaag    960
gctatgtaca ctttgtctgc ctaagatgaa gttttctctt tggctttctc tccaaacaga    1020
tactggttgg ctgctgccac tgctaccggt attaaggtct tttctttgga cccacaatac    1080
ttggtcgatg acttgagacc agaatttgct ggttacagca aggccgctga accacatgct    1140
gtttctttgg cttggtctgc tgacggtcaa actttgtttg ccggttacac cgacaacgtc    1200
```
attagagttt ggcaagttat gactgctaac taa    1233

<210> SEQ ID NO 5
<211> LENGTH: 1314
<212> TYPE: DNA
<213> ORGANISM: Artificial Sequence
<220> FEATURE:
<223> OTHER INFORMATION: Synthetic:  xylA3*

<400> SEQUENCE: 5

```
atggctaaag aatatttccc tcaaattcaa aagataaaat tcgatggtaa agatagcaag     60
aacccattgg cctttcatta ctatgatgcc gaaaaagagg tcatgggtaa aaaaatgaaa    120
gactggttaa gatttgccat ggcttggtgg cacaccttgt gtgctgaagg agcagatcaa    180
tttggaggag ggactaaaag tttcccatgg aacgaaggta cagacgcaat tgaaatagca    240
aagcaaaaag ttgatgctgg tttcgagata atgcaaaaat taggtattcc ttactattgt    300
tttcatgacg tggatttagt atctgaaggt aactctattg gggaatatga atccaacttg    360
aaggcagttg tcgcgtactt gaaagataaa cagaaggaaa ctgggattaa gttattatgg    420
tcatctgcta atgtatttgg tcataaaagg tatatgaacg gagcttcgac taatcctgat    480
tttgatgtgt tgcgagggc tattgtacaa attaaaaacg caatcgacac aggcatcgaa    540
ttgggcgcag aaaattacgt gttttggggc ggtagagaag gttatatgtc attacttaat    600
actgatcaaa aagagaaaaa agaacatatg gcaaccatgt tgaccatggc tagggactat    660
gcacgtagta aaggctttaa aggtaccttc cttattgaac ctaagcctat ggaacctact    720
aaacaccaat acgacgtaga cactgagact gcaatcggtt tcttgaaagc tcataatcta    780
gataaagact tcaaagtcaa tattgaagtt aatcacgcta ctctagccgg tcatacgttc    840
gagcatgagt tggcttgcgc tgtagacgca gggatgttag gtagcataga tgccaatagg    900
ggtgactatc aaaatggctg ggacactgac cagtttccta tcgaccagta cgaattggta    960
caggcttgga tggaaattat aagggggtgg cgttttgtaa ccggtggaac aaacttcgac   1020
gctaagacaa gacgtaattc gactgactta gaagatatta ttatcgctca tgtgtctggt   1080
atggatgcca tggctcgtgc attggagaat gcagctaaat tgttacagga gtctccatac   1140
acaaaaatga agaaggaaag atatgcttca ttcgattctg aataggaaa agattttgaa   1200
gatgggaaac tgacattgga gcaagtctat gaatatggaa agaagaatgg agaaccgaaa   1260
caaacctcag gaaaacaaga actatacgag gctattatcg cgatgtatca ataa         1314
```

<210> SEQ ID NO 6
<211> LENGTH: 1314
<212> TYPE: DNA
<213> ORGANISM: Artificial Sequence
<220> FEATURE:
<223> OTHER INFORMATION: Synthetic:  xylA from Piromyces sp.

<400> SEQUENCE: 6

```
atggctaagg aatacttccc acaaatccaa aagatcaagt tcgaaggtaa ggactctaag     60
aacccattgg ctttccacta ctacgacgct gaaaaggaag ttatgggtaa gaagatgaag    120
gactggttga gattcgctat ggcttggtgg cacaccttgt gtgctgaagg tgctgaccaa    180
ttcggtggtg gtaccaagtc tttcccatgg aacgaaggta ccgacgctat cgaaatcgct    240
aagcaaaagg ttgacgctgg tttcgaaatc atgcaaaagt gggtatccc atactactgt    300
ttccacgacg tcgacttggt ttctgaaggt aactctatcg aagaatacga atctaacttg    360
aaggctgttg ttgcttactt gaaggaaaag caaaaggaaa ctggtatcaa gttgttgtgg    420
```

```
tctaccgcta acgttttcgg tcacaagaga tacatgaacg gtgcttctac caacccagac    480
ttcgacgttg ttgctagagc tatcgttcaa atcaagaacg ctatcgacgc tggtatcgaa    540
ttgggtgctg aaaactacgt tttctggggt ggtagagaag gttacatgtc tttgttgaac    600
accgaccaaa agagagaaaa ggaacacatg gctaccatgt tgaccatggc tagagactac    660
gctagatcta agggtttcaa gggtaccttc ttgatcgaac caaagccaat ggaaccaacc    720
aagcaccaat acgacgttga caccgaaacc gctatcggtt tcttgaaggc tcacaacttg    780
gacaaggact tcaaggtcaa catcgaagtt aaccacgcta ccttggctgg tcacaccttc    840
gaacacgaat tggcttgtgc tgttgacgct ggtatgttgg gttctatcga cgctaacaga    900
ggtgactacc aaaacggttg ggacaccgac caattcccaa tcgaccaata cgaattggtt    960
caagcctgga tggaaatcat cagaggtggt ggtttcgtta ctggtggtac caacttcgac   1020
gctaagacca agaaactc taccgacttg aagacatca tcatcgctca cgtttctggt   1080
atggacgcta tggctagagc tttgaaaac gctgctaagt tgttgcaaga atctccatac   1140
accaagatga agaaggaaag atacgcttct ttcgactctg gtatcggtaa ggacttcgaa   1200
gacggtaagt tgaccttgga acaagtttac gaatacggta agaagaacgg tgaaccaaag   1260
caaacctctg gtaagcaaga attgtacgaa gctatcgttg ctatgtacca ataa        1314
```

<210> SEQ ID NO 7
<211> LENGTH: 1317
<212> TYPE: DNA
<213> ORGANISM: Artificial Sequence
<220> FEATURE:
<223> OTHER INFORMATION: Synthetic: xylA from Clostridium
      phytofermentans

<400> SEQUENCE: 7

```
atgaaaaatt actttccaaa tgttccagaa gtaaatacg aaggcccaaa ttcaacgaat     60
ccatttgctt taaatatta tgacgcaaat aaagttgtag cgggtaaaac aatgaaagag    120
cactgtcgtt ttgcattatc ttggtggcat actctttgtg caggtggtgc tgatccattc    180
ggtgtaacaa ctatggatag aacctacgga aatatcacag atccaatgga acttgctaag    240
gcaaaagttg acgctggttt cgaattaatg actaaattag gaattgaatt cttctgtttc    300
catgacgcag atattgctcc agaaggtgat acttttgaag agtcaaagaa gaatcttttt    360
gaaatcgttg attacatcaa agagaagatg gatcagactg gtatcaagtt attatggggt    420
actgctaata actttagtca tccaagattt atgcatggtg cttccacatc ttgcaacgca    480
gacgtatttg catatgctgc tgctaagatt aagaatgcat agatgcaac aattaaatta    540 ggcggtaaag gttatgtatt ctggggtggt cgtgaaggtt atgaaacact tcttaataca    600
gatttaggac ttgagcttga taatatggct agacttatga agatggctgt agagtatggc    660
cgtgcaaatg gttttgatgg cgacttctat attgagccaa agccaaagga accaaccaag    720
catcaatatg attttgatac agcaaccgta cttgctttcc ttcgcaaata tggcttagaa    780
aaagatttca agatgaacat tgaagcaaac catgctactc ttgcaggtca taccttgaa    840 catgaacttg caatggctag agttaatggt gcatttggtt ctgtagatgc aaaccagggt    900
gatccaaacc ttgatgggga tacggatcaa ttcccaactg atgttcatag tgcaactctt    960
gcaatgcttc aagtacttaa ggctggtgga ttcactaacg gcggacttaa ctttgatgca   1020
aaggtaagac gtggttcctt cgaatttgat gatattgcat acggttatat tgcaggaatg   1080 gatactttg cacttggttt aattaaggct gctgagatta tcgacgatgg tagaatcgca   1140
```
aaatttgtag atgatcgtta tgcaagctat aaaacaggaa ttggtaaagc aattgtggat       1200
ggaactacat ctcttgaaga attagagcag tatgttttaa cacatagtga accagtaatg       1260
cagagtggtc gtcaggaagt tcttgaaaca atcgtaaata atattttatt tagataa        1317

<210> SEQ ID NO 8
<211> LENGTH: 1320
<212> TYPE: DNA
<213> ORGANISM: Artificial Sequence
<220> FEATURE:
<223> OTHER INFORMATION: Synthetic: xylA from Clostridium
      thermosulfurgenes

<400> SEQUENCE: 8
atgaataaat attttgagaa cgtatctaaa ataaaatatg aaggaccaaa atcaaacaat        60
ccttattctt ttaaatttta caatcctgag gaagtaatcg atggtaagac gatggaggag       120
catcttcgct tttctatagc ttattggcac acttttactg ctgatggaac agatcaattt       180
ggcaaagcta ccatgcaaag gccatggaat cactatacag atcctatgga catagctaaa       240
gcaagggtag aggcagcatt tgagttttt gataagataa atgcaccgta tttctgcttc       300
catgatagag atattgcccc tgaaggagac actcttagag acgaacaa aaatttagat        360 acaatagttg ctatgataaa ggattacttg aagaccagca agacgaaagt tttgtggggt       420
actgcgaatc ttttctccaa tccaagattt gtgcatggtg catcaacgtc ttgcaatgcc       480
gatgttttcg catattctgc agcgcaagtc aaaaaagcac ttgagattac taaggagctt       540
ggtggcgaaa actacgtatt ctggggtgga agagaaggat atgagacact tctcaataca       600
gatatggagt ttgagcttga taattttgca agatttttgc acatggctgt tgattatgca       660
aaggaaatcg gctttgaagg ccagttcttg attgagccga gccaaagga gcctacaaag       720 catcaatacg actttgacgt ggcaaatgta ttggcattct tgagaaaata cgatcttgac       780
aaatatttca agttaatat cgaagcaaat catgcaacat tagcattcca tgatttccag       840
catgagctaa gatacgccag aataaacggt gtattaggat cgattgacgc aaatacgggt       900
gatatgctat aggatggga tacagatcag ttccctacag atatacgcat gacaacactt       960
gctatgtatg aagttataa gatgggtgga tttgacaaag gcggactcaa cttcgatgcg      1020
aaagtaagac gtgcttcatt tgagccagaa gatctttct tgggtcacat agcaggaatg       1080
gatgcttttg caaaaggctt caaagtggct tacaagcttg taaaagatag ggtatttgac      1140
aagttcatcg aagaaagata tgcaagctac aaagatggca taggtgcaga tattgtaagt      1200
gggaaagctg attttagaag tcttgaaaag tatgcattag agcgcagcca gattgtcaac      1260
aaatcaggaa gacaagagct attagagtca atcctaaatc agtatttgtt tgcagaataa      1320

<210> SEQ ID NO 9
<211> LENGTH: 1803
<212> TYPE: DNA
<213> ORGANISM: Artificial Sequence
<220> FEATURE:
<223> OTHER INFORMATION: Synthetic: XKS1

<400> SEQUENCE: 9
atgttgtgtt cagtaattca gagacagaca agagaggttt ccaacacaat gtctttagac        60
tcatactatc tgggtttga tctttcgacc caacaactga aatgtctcgc cattaaccag       120
gacctaaaaa ttgtccattc agaaacagtg gaatttgaaa aggatcttcc gcattatcac       180
acaaagaagg gtgtctatat acacggcgac actatcgaat gtcccgtagc catgtggtta       240

```
gaggctctag atctggttct ctcgaaatat cgcgaggcta aatttccatt gaacaaagtt       300
atggccgtct cagggtcctg ccagcagcac gggtctgtct actggtcctc ccaagccgaa       360
tctctgttag agcaattgaa taagaaaccg gaaaaagatt tattgcacta cgtgagctct       420
gtagcatttg caaggcaaac cgcccccaat tggcaagacc acagtactgc aaagcaatgt       480
caagagtttg aagagtgcat aggtgggcct gaaaaaatgg ctcaattaac agggtccaga       540
gcccatttta gatttactgg tcctcaaatt ctgaaaattg cacaattaga accagaagct       600
tacgaaaaaa caaagaccat ttctttagtg tctaattttt tgacttctat cttagtgggc       660
catcttgttg aattagagga ggcagatgcc tgtggtatga acctttatga tatacgtgaa       720
agaaaattca gtgatgagct actacatcta attgatagtt cttctaagga taaaactatc       780
agacaaaaat taatgagagc acccatgaaa aatttgatag cgggtaccat ctgtaaatat       840
tttattgaga gtacggtttc aatacaaac tgcaaggtct ctcccatgac tggggataat       900
ttagccacta tatgttcttt accctgcgg aagaatgacg ttctcgtttc cctaggaaca       960
agtactacag ttcttctggt caccgataag tatcacccct ctccgaacta tcatcttttc      1020
attcatccaa ctctgccaaa ccattatatg ggtatgattt gttattgtaa tggttctttg      1080
gcaagggaga ggataagaga cgagttaaac aaagaacggg aaaataatta tgagaagact      1140
aacgattgga ctcttttaa tcaagctgtg ctagatgact cagaaagtag tgaaaatgaa      1200
ttaggtgtat attttcctct gggggagatc gttcctagcg taaaagccat aaacaaagg       1260 gttatcttca atccaaaaac gggtatgatt gaaagagagg tggccaagtt caaagacaag      1320
aggcacgatg ccaaaaatat tgtagaatca caggctttaa gttgcagggt aagaatatct      1380
cccctgcttt cggattcaaa cgcaagctca aacagagac tgaacgaaga tacaatcgtg      1440
aagtttgatt acgatgaatc tccgctgcgg gactacctaa ataaaaggcc agaaaggact      1500
ttttttgtag gtggggcttc taaaaacgat gctattgtga agaagtttgc tcaagtcatt      1560
ggtgctacaa agggtaattt taggctagaa acaccaaact catgtgccct tggtggttgt      1620
tataaggcca tgtggtcatt gttatatgac tctaataaaa ttgcagttcc ttttgataaa      1680
tttctgaatg acaattttcc atggcatgta atggaaagca tatccgatgt ggataatgaa      1740
aattgggatc gctataattc caagattgtc cccttaagcg aactggaaaa gactctcatc      1800
taa                                                                    1803

<210> SEQ ID NO 10
<211> LENGTH: 1871
<212> TYPE: DNA
<213> ORGANISM: Artificial Sequence
<220> FEATURE:
<223> OTHER INFORMATION: Synthetic:  xyl3 from Scheffersomyces stipitis

<400> SEQUENCE: 10
atgaccacta cccatttga tgctccagat aagctcttcc tcgggttcga tctttcgact        60
cagcagttga agatcatcgt caccgatgaa aacctcgctg ctctcaaaac ctacaatgtc       120
gagttcgata gcatcaacag ctctgtccag aagggtgtca ttgctatcaa cgacgaaatc       180
agcaagggtg ccattatttc ccccgtttac atgtggttgg atgcccttga ccatgttttt       240
gaagacatga agaaggacgg attcccttc aacaaggttg ttggtatttc cggttcttgt        300
caacagcacg ttcggtata ctggtctaga acggccgaga aggtcttgtc cgaattggac        360
gctgaatctt cgttatcgag ccagatgaga tctgctttca ccttcaagca cgctccaaac       420
```

| | |
|---|---|
| tggcaggatc actctaccgg taaagagctt gaagagttcg aaagagtgat tggtgctgat | 480 |
| gccttggctg atatctctgg ttccagagcc cattacagat tcacagggct ccagattaga | 540 |
| aagttgtcta ccagattcaa gcccgaaaag tacaacagaa ctgctcgtat ctctttagtt | 600 |
| tcgtcatttg ttgccagtgt gttgcttggt agaatcacct ccattgaaga agccgatgct | 660 |
| tgtggaatga acttgtacga tatcgaaaag cgcgagttca acgaagagct cttggccatc | 720 |
| gctgctggtg tccaccctga gttggatggt gtagaacaag acggtgaaat ttacagagct | 780 |
| ggtatcaatg agttgaagag aaagttgggt cctgtcaaac ctataacata cgaaagcgaa | 840 |
| ggtgacattg cctcttactt tgtcaccaga tacggcttca accccgactg taaaatctac | 900 |
| tcgttcaccg gagacaattt ggccacgatt atctcgttgc ctttggctcc aaatgatgct | 960 |
| ttgatctcat tgggtacttc tactacagtt ttaattatca ccaagaacta cgctccttct | 1020 |
| tctcaatacc atttgtttaa acatccaacc atgcctgacc actacatggg catgatctgc | 1080 |
| tactgtaacg gttccttggc cagagaaaag gttagagacg aagtcaacga aaagttcaat | 1140 |
| gtagaagaca agaagtcgtg ggacaagttc aatgaaatct ggacaaatc cacagacttc | 1200 |
| aacaacaagt tgggtatttta cttcccactt ggcgaaattg tccctaatgc cgctgctcag | 1260 |
| atcaagagat cggtgttgaa cagcaagaac gaaattgtag acgttgagtt gggcgacaag | 1320 |
| aactggcaac ctgaagatga tgtttcttca attgtagaat cacagacttt gtcttgtaga | 1380 |
| ttgagaactg gtccaatgtt gagcaagagt ggagattctt ctgcttccag ctctgcctca | 1440 |
| cctcaaccag aaggtgatgg tacagatttg cacaaggtct accaagactt ggttaaaaag | 1500 |
| tttggtgact tgttcactga tggaaagaag caaacctttg agtctttgac cgccagacct | 1560 |
| aaccgttgtt actacgtcgg tggtgcttcc aacaacggca gcattatccc aagatgggtt | 1620 |
| ccatcttggc tcccgtcaac ggaaactaca aggttgacat tcctaacgcc tgtgcattgg | 1680 |
| gtggtgctta caaggccagt tggagttacg agtgtgaagc caagaaggaa tggatcggat | 1740 |
| acgatcagta tcaacaga ttgtttgaag taagtgacga gatgaatctg ttcgaagtca | 1800 |
| aggataaatg gctcgaatat gccaacgggg ttggaatgtt ggccaagatg gaaagtgaat | 1860 |
| tgaaacacta a | 1871 |

<210> SEQ ID NO 11
<211> LENGTH: 1008
<212> TYPE: DNA
<213> ORGANISM: Artificial Sequence
<220> FEATURE:
<223> OTHER INFORMATION: Synthetic: TAL1

<400> SEQUENCE: 11

| | |
|---|---|
| atgtctgaac cagctcaaaa gaaacaaaag gttgctaaca actctctaga acaattgaaa | 60 |
| gcctccggca ctgtcgttgt tgccgacact ggtgatttcg gctctattgc caagtttcaa | 120 |
| cctcaagact ccacaactaa cccatcattg atcttggctg ctgccaagca accaacttac | 180 |
| gccaagttga tcgatgttgc cgtggaatac ggtaagaagc atggtaagac caccgaagaa | 240 |
| caagtcgaaa atgctgtgga cagattgtta gtcgaattcg gtaaggagat cttaaagatt | 300 |
| gttccaggca gagtctccac cgaagttgat gctagattgt cttttgacac tcaagctacc | 360 |
| attgaaaagg ctagacatat cattaaattg tttgaacaag aaggtgtctc caaggaaaga | 420 |
| gtccttatta aaattgcttc cacttgggaa ggtattcaag ctgccaaaga attggaagaa | 480 |
| aaggacggta tccactgtaa tttgactcta ttattctcct tcgttcaagc agttgcctgt | 540 |
| gccgaggccc aagttacttt tgatttcccca tttgttggta gaattctaga ctggtacaaa | 600 |

```
tccagcactg gtaaagatta caagggtgaa gccgacccag gtgttatttc cgtcaagaaa      660
atctacaact actacaagaa gtacggttac aagactattg ttatgggtgc ttcttcaga      720 agcactgacg aaatcaaaaa cttggctggt gttgactatc taacaatttc tccagcttta      780
ttggacaagt tgatgaacag tactgaacct ttcccaagag ttttggaccc tgtctccgct      840
aagaaggaag ccggcgacaa gatttcttac atcagcgacg aatctaaatt cagattcgac      900
ttgaatgaag acgctatggc cactgaaaaa ttgtccgaag gtatcagaaa attctctgcc      960
gatattgtta ctctattcga cttgattgaa aagaaagtta ccgcttaa                 1008

<210> SEQ ID NO 12
<211> LENGTH: 970
<212> TYPE: DNA
<213> ORGANISM: Artificial Sequence
<220> FEATURE:
<223> OTHER INFORMATION: Synthetic: tal1 from Scheffersomyces stipitis

<400> SEQUENCE: 12
atgtcctcca actcccttga acaattgaaa gccacaggta ccgtcatcgt caccgacacc       60
ggtgaattcg actcgattgc caagtacact ccacaagatg ccaccaccaa cccatcgttg      120
attttggctg ctgctaagaa gcctgaatac gccaaggtca ttgacgtcgc catgaatacg      180
ccaaggacaa gggttcctcc aagaaggaaa aggctgaaat cgccttggac cgtttgttga      240
ttgaattcgg taagaacatc ttggccattg ttccaggaag agtgtctacc gaagtcgacg      300
ccagattgtc tttcgacaaa gaggccacat caagaaggct cttgaattga ttgccttgta      360
cgaatcccaa ggtatctcca aggacagaat cttgatcaag atcgcctcca cttgggaagg      420
tatccaagct gccagagaat ggaagccaa gcacggtatt cactgtaact tgactttgtt      480
gttctctttc gttcaggcag ttgcctgtgc tgaagccaag gtcaccttga tctcgccatt      540
cgtcggcaga tcttggact ggtacaaggc ttctaccgga aagacctacg aaggtgacga      600
agacccaggt gtgatttctg tcagagccat ctacaactac tacaagaagt acggctacaa      660
aactattgtc atgggtgcct ctttcagaaa caccggtgaa atcaaggctt ggctggttg      720 cgactactta actgttgctc ctaagttgtt ggaagaattg ttgaactcca ctgaaccagt      780
tccacaagtg ttggacgctg cttctgcctc tgctactgat gtcgaaaagg tttcttacgt      840
tgatgacgaa gctaccttca gatacttgtt caacgaagac gccatggcta ccgaaaagtt      900
ggcccaaggt atcagagctt tcggcaagga cgctgtcacc ttgttggaac aattggaagc      960
cagattctaa                                                             970

<210> SEQ ID NO 13
<211> LENGTH: 984
<212> TYPE: DNA
<213> ORGANISM: Artificial Sequence
<220> FEATURE:
<223> OTHER INFORMATION: Synthetic: GRE3

<400> SEQUENCE: 13
atgtcttcac tggttactct taataacggt ctgaaaatgc ccctagtcgg cttagggtgc       60
tggaaaattg acaaaaaagt ctgtgcgaat caaatttatg aagctatcaa attaggctac      120
cgtttattcg atggtgcttg cgactacggc aacgaaaagg aagttggtga aggtatcagg      180
aaagccatct ccgaaggtct tgtttctaga aggatatat tgttgtttc aaagttatgg      240 aacaattttc accatcctga tcatgtaaaa ttagctttaa agaagaccct taagcgatatg      300
```

```
ggacttgatt atttagacct gtattatatt cacttcccaa tcgccttcaa atatgttcca    360
tttgaagaga ataccctcc aggattctat acgggcgcag atgacgagaa gaaaggtcac     420
atcaccgaag cacatgtacc aatcatagat acgtaccggg ctctggaaga atgtgttgat    480
gaaggcttga ttaagtctat tggtgttttcc aactttcagg gaagcttgat tcaagattta   540
ttacgtggtt gtagaatcaa gcccgtggct ttgcaaattg aacaccatcc ttatttgact    600
caagaacacc tagttgagtt ttgtaaatta cacgatatcc aagtagttgc ttactcctcc    660
ttcggtcctc aatcattcat tgagatggac ttacagttgg caaaaccac gccaactctg     720 ttcgagaatg atgtaatcaa gaaggtctca caaaaccatc caggcagtac cacttcccaa    780
gtattgctta gatgggcaac tcagagaggc attgccgtca ttccaaaatc ttccaagaag    840
gaaaggttac ttggcaacct agaaatcgaa aaaaagttca ctttaacgga gcaagaattg    900
aaggatattt ctgcactaaa tgccaacatc agatttaatg atccatggac ctggttggat    960
ggtaaattcc cacttttgc ctga                                            984

<210> SEQ ID NO 14
<211> LENGTH: 939
<212> TYPE: DNA
<213> ORGANISM: Artificial Sequence
<220> FEATURE:
<223> OTHER INFORMATION: Synthetic:  PHO13

<400> SEQUENCE: 14
atgactgctc aacaaggtgt accaataaag ataaccaata aggagattgc tcaagaattc     60
ttggacaaat atgacacgtt tctgttcgat tgtgatggtg tattatggtt aggttctcaa    120
gcattaccat acaccctgga aattctaaac cttttgaagc aattgggcaa caactgatc     180 ttcgttacga ataactctac caagtcccgt ttagcataca cgaaaaagtt tgcttcgttt    240
ggtattgatg tcaaagaaga acagattttc acctctggtt atgcgtcagc tgtttatatt    300
cgtgactttc tgaaattgca gcctggcaaa gataaggtat gggtatttgg agaaagcggt    360
attggtgaag aattgaaact aatggggtac gaatctctag gaggtgccga ttccagattg    420
gatacgccgt tcgatgcagc taaatcacca ttttttggtga acggccttga taaggatgtt    480
agttgtgtta ttgctgggtt agacacgaag gtaaattacc accgtttggc tgttacactg    540
cagtatttgc agaaggattc tgttcacttt gttggtacaa atgttgattc tactttcccg    600
caaaagggtt atacatttcc cggtgcaggc tccatgattg aatcattggc attctcatct    660
aataggaggc catcgtactg tggtaagcca aatcaaaata tgctaaacag cattatatcg    720
gcattcaacc tggatagatc aaagtgctgt atggttggtg acagattaaa caccgatatg    780
aaattcggtg ttgaaggtgg gttaggtggc acactactcg ttttgagtgg tattgaaacc    840
gaagagagag ccttgaagat ttcgcacgat tatccaagac ctaaatttta cattgataaa    900
cttggtgaca tctacacctt aaccaataat gagttatag                           939

<210> SEQ ID NO 15
<211> LENGTH: 9435
<212> TYPE: DNA
<213> ORGANISM: Artificial Sequence
<220> FEATURE:
<223> OTHER INFORMATION: Synthetic:  TEFp- PMR1 mt- CYC1t

<400> SEQUENCE: 15
gacgaaaggg cctcgtgata cgcctatttt tataggttaa tgtcatgata ataatggttt     60
cttaggacgg atcgcttgcc tgtaacttac acgcgcctcg tatcttttaa tgatggaata    120
```

```
atttgggaat ttactctgtg tttatttatt tttatgtttt gtatttggat tttagaaagt      180
aaataaagaa ggtagaagag ttacggaatg aagaaaaaaa aataaacaaa ggtttaaaaa      240
atttcaacaa aaagcgtact ttacatatat atttattaga caagaaaagc agattaaata      300
gatatacatt cgattaacga taagtaaaat gtaaaatcac aggattttcg tgtgtggtct      360
tctacacaga caagatgaaa caattcggca ttaatacctg agagcaggaa gagcaagata      420
aaaggtagta tttgttggcg atcccccctag agtcttttac atcttcggaa aacaaaaact      480
attttttctt taatttcttt ttttactttc tattttttaat ttatatattt atattaaaaa      540
atttaaatta taattatttt tatagcacgt gatgaaaagg acccaggtgg cacttttcgg      600
ggaaatgtgc gcggaacccc tatttgttta ttttttctaaa tacattcaaa tatgtatccg      660
ctcatgagac aataaccctg ataaatgctt caataatatt gaaaaaggaa gagtatgagt      720
attcaacatt tccgtgtcgc ccttattccc ttttttgcgg cattttgcct tcctgttttt      780
gctcacccag aaacgctggt gaaagtaaaa gatgctgaag atcagttggg tgcacgagtg      840
ggttacatcg aactggatct caacagcggt aagatccttg agagttttcg ccccgaagaa      900
cgttttccaa tgatgagcac ttttaaagtt ctgctatgtg gcgcggtatt atcccgtatt      960
gacgccgggc aagagcaact cggtcgccgc atacactatt ctcagaatga cttggttgag     1020
tactcaccag tcacagaaaa gcatcttacg gatggcatga cagtaagaga attatgcagt     1080
gctgccataa ccatgagtga taacactgcg gccaacttac ttctgacaac gatcggagga     1140
ccgaaggagc taaccgcttt tttgcacaac atgggggatc atgtaactcg ccttgatcgt     1200
tgggaaccgg agctgaatga agccatacca aacgacgagc gtgacaccac gatgcctgta     1260
gcaatggcaa caacgttgcg caaactatta actggcgaac tacttactct agcttcccgg     1320
caacaattaa tagactggat ggaggcggat aaagttgcag gaccacttct gcgctcggcc     1380
cttccggctg gctggtttat tgctgataaa tctggagccg gtgagcgtgg gtctcgcggt     1440
atcattgcag cactggggcc agatggtaag ccctcccgta tcgtagttat ctacacgacg     1500
gggagtcagg caactatgga tgaacgaaat agacagatcg ctgagatagg tgcctcactg     1560
attaagcatt ggtaactgtc agaccaagtt tactcatata tactttagat tgatttaaaa     1620
cttcattttt aatttaaaag gatctaggtg aagatccttt ttgataatct catgaccaaa     1680
atcccttaac gtgagttttc gttccactga gcgtcagacc ccgtagaaaa gatcaaagga     1740
tcttcttgag atcctttttt tctgcgcgta atctgctgct tgcaaacaaa aaaaccaccg     1800
ctaccagcgg tggtttgttt gccggatcaa gagctaccaa ctctttttcc gaaggtaact     1860
ggcttcagca gagcgcagat accaaatact gtccttctag tgtagccgta gttaggccac     1920
cacttcaaga actctgtagc accgcctaca tacctcgctc tgctaatcct gttaccagtg     1980
gctgctgcca gtggcgataa gtcgtgtctt accgggttgg actcaagacg atagttaccg     2040
gataaggcgc agcggtcggg ctgaacgggg gttcgtgca cacagcccag cttggagcga     2100
acgacctaca ccgaactgag atacctacag cgtgagctat gagaaagcgc cacgcttccc     2160
gaagggagaa aggcggacag gtatccggta agcggcaggg tcggaacagg agagcgcacg     2220
agggagcttc caggggggaaa cgcctggtat ctttatagtc ctgtcgggtt cgccacctc      2280 tgacttgagc gtcgattttt gtgatgctcg tcagggggggc ggagcctatg gaaaaacgcc     2340
agcaacgcgg ccttttttacg gttcctggcc ttttgctggc cttttgctca catgttcttt     2400
cctgcgttat ccccctgattc tgtggataac cgtattaccg cctttgagtg agctgatacc     2460
```

```
gctcgccgca gccgaacgac cgagcgcagc gagtcagtga gcgaggaagc ggaagagcgc    2520
ccaatacgca aaccgcctct ccccgcgcgt tggccgattc attaatgcag ctggcacgac    2580
aggtttcccg actggaaagc gggcagtgag cgcaacgcaa ttaatgtgag ttacctcact    2640
cattaggcac cccaggcttt acactttatg cttccggctc ctatgttgtg tggaattgtg    2700
agcggataac aatttcacac aggaaacagc tatgaccatg attacgccaa gcgcgcaatt    2760
aaccctcact aaagggaaca aaagctggag ctcatagctt caaaatgttt ctactccttt    2820
tttactcttc cagatttctc ggactccgcg catcgccgta ccacttcaaa cacccaagc    2880 acagcatact aaatttccct ctttcttcct ctagggtgtc gttaattacc cgtactaaag    2940
gtttggaaaa gaaaaagag accgcctcgt ttcttttct cgtcgaaaa aggcaataaa    3000 aattttatc acgtttcttt ttcttgaaaa ttttttttt gattttttc tctttcgatg    3060 acctcccatt gatatttaag ttaataaacg gtcttcaatt tctcaagttt cagtttcatt    3120
tttcttgttc tattacaact ttttttactt cttgctcatt agaaagaaag catagcaatc    3180
taatctaagt tttctagaac tagtatgagt gacaatccat ttaatgcgag tcttcttgac    3240
gaggactcaa accgtgagag agaaatacta gatgccacag cagaggccct ttcgaaacca    3300
agcccttctt tagagtattg tactttatcc gtggacgaag ctctagaaaa actgacact    3360 gacaaaaacg gtggtttacg atcatctaac gaggccaaca ataggagatc actttatggc    3420
cccaatgaaa taaccgtaga agatgatgaa agtcttttca agaagttctt gtcaaatttc    3480
attgaggatc gaatgattct acttttaata ggatccgcag tggtctctct ttttatgggt    3540
aacattgatg atgctgttag tatcacactg gccattttca tagttgtcac tgtcggtttt    3600
gtccaagaat ataggtctga aaaatctcta gaagcgttga ataaattggt tcctgctgaa    3660
tgtcacttaa tgagatgtgg tcaagagagt catgtactgg cttccacctt ggttcctggt    3720
gatttagtgc acttcagaat aggtgacaga atccccgcag acattagaat tattgaagca    3780 atcgattat ccatcgatga aagtaattta actggtgaaa atgaaccggt acataaaacc    3840
tcacaaacga tcgaaaaatc ttcctttaac gatcagccta attcaattgt accgatttct    3900
gagagatctt gtatagctta tatgggtaca ttagtcaagg aaggtcatgg taagggtatc    3960
gtcgtaggaa caggtacaaa cacatccttt ggtgccgttt ttgaaatgat gaataatatt    4020
gaaaaaccga agactccatt gcagttaaca atggacaaat tgggaaagga cttgtcactg    4080
gttagcttca tagttattgg tatgatttgt ttagttggta tcatacaagg tagatcttgg    4140
ttagaaatgt tccaaatatc ggtatcctta gcggttgctg ctattccaga agggttacca    4200
attattgtca ctgttacttt ggcattgggt gttctgagaa tggccaagcg taaagccatc    4260
gtgagaaggt taccaagtgt cgaaacttta ggctctgtca acgttatctg ctccgacaaa    4320
acaggtacac taacctcaaa ccacatgacc gtatctaaac tttggtgctt ggacagtatg    4380
tccaataagc taaacgtcct ctcattagac aaaaataaga agactaaaaa ttctaatgga    4440
aatttgaaaa actatttgac tgaagacgtt agggaaactc taactatcgg taatctctgt    4500
aataatgcat ctttctctca agaacatgcc atatttctgg gaaatcctac tgatgtagct    4560
cttttagagc aattggcaaa ctttgaaatg cctgatatca gaaacaccgt tcaaaaagtt    4620
caggaacttc catttaactc gaaaagaaaa ttaatggcaa ccaagattct caaccctgtc    4680
gacaataagt gtacagttta tgttaaaggt gcatttgaaa gaattcttga gtactccaca    4740
agttatttga aatcaagggg taaaaaaact gaaaagttga ctgaagccca aaaagctacg    4800
ataaatgagt gcgcaaattc tatggcatct gaaggtttgc gtgtctttgg atttgctaaa    4860
```

```
ctaactttgt ctgattcatc aactcctcta accgaagacc taatcaaaga tttaaccttt    4920
actggtttaa tcggtatgaa tgacccacca agaccgaacg ttaaatttgc catcgaacaa    4980
ttactacaag gtggtgtcca tattattatg atcactggtg attctgagaa taccgcagta    5040
aacattgcaa aacaaattgg tattccagtt attgatccaa agctttccgt tttatccggt    5100
gataaattag atgaaatgtc agatgatcaa ctggccaatg tcatcgacca cgttaatatt    5160
tttgctcgtg ctacgcctga gcataagtta aacattgttc gtgcattaag aaagaggggt    5220
gatgtggtag caatgactgg tgatgatgtt aacgacgctc ctgcgttgaa actttcagat    5280
attggtgttt ctatgggtag aattggtaca gatgtagcca agaagcctc agatatggtc     5340 ttaactgatg atgacttcag tactattta actgccattg aagagggtaa aggtatcttt     5400
aataatattc agaatttcct gacttttcaa ttgtctactt ctgttgccgc actatcatta    5460
gttgcactat ctacagcgtt taaactaccc aatccactga acgcaatgca aattctttgg    5520
ataaatattt taatggatgg ccaccagct caatccttag gtgtggaacc tgttgatcat     5580
gaagttatga aaaaacctcc aagaaaacgt accgataaaa ttttgaccca tgatgtaatg    5640
aaacgtttac taaccaccgc ggcctgtatc atcgttggga cagtttacat ttttgttaaa    5700
gagatggccg aagatggtaa agtaactgct agagatacta ctatgacatt tacttgtttt    5760
gttttttttg atatgtttaa tgctttggcc tgcagacata acacaaagtc aatcttcgaa    5820
atcggctttt tcacgaacaa aatgttcaac tacgccgttg gactgtctct gttaggtcaa    5880
atgtgcgcta tatatacc atttttccaa agtatcttta aaactgagaa acttggtatc      5940
tctgatatac tattgttatt gctcatcagc agtagcgttt tcatcgttga tgaattgaga    6000
aaattgtgga cgaggaaaaa gaatgaagaa gactcaacgt atttctcaaa tgtttgactc    6060
gagattagtt atgtcacgct tacattcacg ccctccccc catccgctc taaccgaaaa      6120 ggaaggagtt agacaacctg aagtctaggt ccctatttat ttttttatag ttatgttagt    6180
attaagaacg ttattatat ttcaaatttt tctttttttt ctgtacagac gcgtgtacgc     6240
atgtaacatt atactgaaaa ccttgcttga gaaggttttg ggacgctcga aggctttaat    6300
ttgggtaccc aattcgccct atagtgagtc gtattacgcg cgctcactgg ccgtcgtttt    6360
acaacgtcgt gactgggaaa accctggcgt tacccaactt aatcgccttg cagcacatcc    6420
ccctttcgcc agctggcgta atagcgaaga ggcccgcacc gatcgccctt cccaacagtt    6480
gcgcagcctg aatggcgaat ggcgcgacgc gccctgtagc ggcgcattaa gcgcggcggg    6540
tgtggtggtt acgcgcagcg tgaccgctac acttgccagc gccctagcgc ccgctccttt    6600
cgctttcttc ccttcctttc tcgccacgtt cgccggcttt ccccgtcaag ctctaaatcg    6660
ggggctccct ttagggttcc gatttagtgc tttacggcac ctcgacccca aaaaacttga    6720
ttagggtgat ggttcacgta gtgggccatc gccctgatag acggttttc gccctttgac     6780 gttggagtcc acgttcttta atagtggact cttgttccaa actggaacaa cactcaaccc    6840
tatctcggtc tattctttg atttataagg gattttgccg atttcggcct attggttaaa    6900
aaatgagctg atttaacaaa aatttaacgc gaatttaac aaaatattaa cgtttacaat     6960
ttcctgatgc ggtattttct ccttacgcat ctgtgcggta tttcacaccg catatcgacg    7020
gtcgaggaga acttctagta tatccacata cctaatatta ttgccttatt aaaaatggaa    7080
tcccaacaat tacatcaaaa tccacattct cttcaaaatc aattgtcctg tacttccttg    7140
ttcatgtgtg ttcaaaaacg ttatatttat aggataatta tactctattt ctcaacaagt    7200
```

-continued

```
aattggttgt ttggccgagc ggtctaaggc gcctgattca agaaatatct tgaccgcagt    7260
taactgtggg aatactcagg tatcgtaaga tgcaagagtt cgaatctctt agcaaccatt    7320
atttttttcc tcaacataac gagaacacac aggggcgcta tcgcacagaa tcaaattcga    7380
tgactggaaa ttttttgtta atttcagagg tcgcctgacg catataccct tttcaactga    7440
aaaattggga gaaaaggaa aggtgagagg ccggaaccgg cttttcatat agaatagaga    7500
agcgttcatg actaaatgct tgcatcacaa tacttgaagt tgacaatatt atttaaggac    7560
ctattgtttt ttccaatagg tggttagcaa tcgtcttact ttctaacttt tcttaccttt    7620
tacatttcag caatatatat atatatttca aggatatacc attctaatgt ctgcccctat    7680
gtctgcccct aagaagatcg tcgttttgcc aggtgaccac gttggtcaag aaatcacagc    7740
cgaagccatt aaggttctta aagctatttc tgatgttcgt tccaatgtca agttcgattt    7800
cgaaaatcat ttaattggtg gtgctgctat cgatgctaca ggtgtcccac ttccagatga    7860
ggcgctggaa gcctccaaga aggttgatgc cgttttgtta ggtgctgtgg gtggtcctaa    7920
atggggtacc ggtagtgtta gacctgaaca aggtttacta aaaatccgta aagaacttca    7980
attgtacgcc aacttaagac catgtaactt tgcatccgac tctcttttag acttatctcc    8040
aatcaagcca caatttgcta aaggtactga cttcgttgtt gtcagagaat tagtgggagg    8100
tatttacttt ggtaagagaa aggaagacga tggtgatggt gtcgcttggg atagtgaaca    8160
atacaccgtt ccagaagtgc aaagaatcac aagaatggcc gctttcatgg ccctacaaca    8220
tgagccacca ttgcctattt ggtccttgga taaagctaat gttttggcct cttcaagatt    8280
atggagaaaa actgtggagg aaaccatcaa gaacgaattc cctacattga aggttcaaca    8340
tcaattgatt gattctgccg ccatgatcct agttaagaac ccaacccacc taaatggtat    8400
tataatcacc agcaacatgt ttggtgatat catctccgat gaagcctccg ttatcccagg    8460
ttccttgggt ttgttgccat ctgcgtcctt ggcctctttg ccagacaaga acaccgcatt    8520
tggtttgtac gaaccatgcc acggttctgc tccagatttg ccaaagaata aggttgaccc    8580
tatcgccact atcttgtctg ctgcaatgat gttgaaattg tcattgaact tgcctgaaga    8640
aggtaaggcc attgaagatg cagttaaaaa ggttttggat gcaggtatca gaactggtga    8700
tttaggtggt tccaacagta ccaccgaagt cggtgatgct gtcgccgaag aagttaagaa    8760
aatccttgct taaaaagatt ctcttttttt atgatatttg tacataaact ttataaatga    8820
aattcataat agaaacgaca cgaaattaca aaatggaata tgttcatagg gtagacgaaa    8880
ctatatacgc aatctacata catttatcaa gaaggagaaa aaggaggata gtaaggaat    8940
acaggtaagc aaattgatac taatggctca acgtgataag gaaaaagaat tgcactttaa    9000
cattaatatt gacaaggagg agggcaccac acaaaaagtt aggtgtaaca gaaaatcatg    9060
aaactacgat tcctaatttg atattggagg attttctcta aaaaaaaaaa aatacaacaa    9120
ataaaaaaca ctcaatgacc tgaccatttg atggagttta agtcaatacc ttcttgaacc    9180
atttcccata atggtgaaag ttccctcaag aattttactc tgtcagaaac ggccttacga    9240
cgtagtcgat atggtgcact ctcagtacaa tctgctctga tgccgcatag ttaagccagc    9300
cccgacaccc gccaacaccc gctgacgcgc cctgacgggc ttgtctgctc ccggcatccg    9360
cttacagaca gctgtgacc gtctccggga gctgcatgtg tcagaggttt tcaccgtcat    9420
caccgaaacg cgcga                                                    9435
```

<210> SEQ ID NO 16
<211> LENGTH: 7815

```
<212> TYPE: DNA
<213> ORGANISM: Artificial Sequence
<220> FEATURE:
<223> OTHER INFORMATION: Synthetic:  TEFp- ASC1 mt- CYC1t (w. SpeI,
      XhoI)

<400> SEQUENCE: 16
```

| | | | | |
|---|---|---|---|---|
| gacgaaaggg | cctcgtgata | cgcctatttt | tataggttaa | tgtcatgata | ataatggttt | 60 |
| cttaggacgg | atcgcttgcc | tgtaacttac | acgcgcctcg | tatcttttaa | tgatggaata | 120 |
| atttgggaat | ttactctgtg | tttatttatt | tttatgtttt | gtatttggat | tttagaaagt | 180 |
| aaataaagaa | ggtagaagag | ttacggaatg | aagaaaaaaa | aataaacaaa | ggtttaaaaa | 240 |
| atttcaacaa | aaagcgtact | ttacatatat | atttattaga | caagaaaagc | agattaaata | 300 |
| gatatacatt | cgattaacga | taagtaaaat | gtaaaatcac | aggattttcg | tgtgtggtct | 360 |
| tctacacaga | caagatgaaa | caattcggca | ttaatacctg | agagcaggaa | gagcaagata | 420 |
| aaaggtagta | tttgttggcg | atccccctag | agtcttttac | atcttcggaa | aacaaaaact | 480 |
| atttttcctt | taatttcttt | ttttactttc | tatttttaat | ttatatattt | atattaaaaa | 540 |
| atttaaatta | taattatttt | tatagcacgt | gatgaaaagg | acccaggtgg | cacttttcgg | 600 |
| ggaaatgtgc | gcggaacccc | tatttgttta | tttttctaaa | tacattcaaa | tatgtatccg | 660 |
| ctcatgagac | aataaccctg | ataaatgctt | caataatatt | gaaaaggaa | gagtatgagt | 720 |
| attcaacatt | tccgtgtcgc | ccttattccc | ttttttgcgg | catttgcct | tcctgttttt | 780 |
| gctcacccag | aaacgctggt | gaaagtaaaa | gatgctgaag | atcagttggg | tgcacgagtg | 840 |
| ggttacatcg | aactggatct | caacagcggt | aagatccttg | agagttttcg | ccccgaagaa | 900 |
| cgttttccaa | tgatgagcac | ttttaaagtt | ctgctatgtg | gcgcggtatt | atcccgtatt | 960 |
| gacgccgggc | aagagcaact | cggtcgccgc | atacactatt | ctcagaatga | cttggttgag | 1020 |
| tactcaccag | tcacagaaaa | gcatcttacg | gatggcatga | cagtaagaga | attatgcagt | 1080 |
| gctgccataa | ccatgagtga | taacactgcg | gccaacttac | ttctgacaac | gatcggagga | 1140 |
| ccgaaggagc | taaccgcttt | tttgcacaac | atgggggatc | atgtaactcg | ccttgatcgt | 1200 |
| tgggaaccgg | agctgaatga | agccatacca | aacgacgagc | gtgacaccac | gatgcctgta | 1260 |
| gcaatggcaa | caacgttgcg | caaactatta | actggcgaac | tacttactct | agcttcccgg | 1320 |
| caacaattaa | tagactggat | ggaggcggat | aaagttgcag | gaccacttct | gcgctcggcc | 1380 |
| cttccggctg | gctggtttat | tgctgataaa | tctggagccg | gtgagcgtgg | gtctcgcggt | 1440 |
| atcattgcag | cactggggcc | agatggtaag | ccctcccgta | tcgtagttat | ctacacgacg | 1500 |
| gggagtcagg | caactatgga | tgaacgaaat | agacagatcg | ctgagatagg | tgcctcactg | 1560 |
| attaagcatt | ggtaactgtc | agaccaagtt | tactcatata | tactttagat | tgatttaaaa | 1620 |
| cttcattttt | aatttaaaag | gatctaggtg | aagatccttt | ttgataatct | catgaccaaa | 1680 |
| atcccttaac | gtgagttttc | gttccactga | gcgtcagacc | ccgtagaaaa | gatcaaagga | 1740 |
| tcttcttgag | atcctttttt | tctgcgcgta | atctgctgct | tgcaaacaaa | aaaaccaccg | 1800 |
| ctaccagcgg | tggtttgttt | gccggatcaa | gagctaccaa | ctctttttcc | gaaggtaact | 1860 |
| ggcttcagca | gagcgcagat | accaaatact | gtccttctag | tgtagccgta | gttaggccac | 1920 |
| cacttcaaga | actctgtagc | accgcctaca | tacctcgctc | tgctaatcct | gttaccagtg | 1980 |
| gctgctgcca | gtggcgataa | gtcgtgtctt | accgggttgg | actcaagacg | atagttaccg | 2040 |
| gataaggcgc | agcggtcggg | ctgaacgggg | ggttcgtgca | cacagcccag | cttggagcga | 2100 |
| acgacctaca | ccgaactgag | atacctacag | cgtgagctat | gagaaagcgc | cacgcttccc | 2160 |

```
gaagggagaa aggcggacag gtatccggta agcggcaggg tcggaacagg agagcgcacg    2220
agggagcttc caggggggaaa cgcctggtat ctttatagtc ctgtcgggtt tcgccacctc    2280
tgacttgagc gtcgattttt gtgatgctcg tcagggggggc ggagcctatg gaaaaacgcc    2340
agcaacgcgg ccttttttacg gttcctggcc ttttgctggc cttttgctca catgttcttt    2400
cctgcgttat ccctgattc tgtggataac cgtattaccg cctttgagtg agctgatacc    2460
gctcgccgca gccgaacgac cgagcgcagc gagtcagtga gcgaggaagc ggaagagcgc    2520
ccaatacgca aaccgcctct ccccgcgcgt tggccgattc attaatgcag ctggcacgac    2580
aggtttcccg actggaaagc gggcagtgag cgcaacgcaa ttaatgtgag ttacctcact    2640
cattaggcac cccaggcttt acactttatg cttccggctc ctatgttgtg tggaattgtg    2700
agcggataac aatttcacac aggaaacagc tatgaccatg attacgccaa gcgcgcaatt    2760
aaccctcact aaagggaaca aaagctggag ctcatagctt caaaatgttt ctactccttt    2820
tttactcttc cagatttctc ggactccgcg catcgccgta ccacttcaaa acacccaagc    2880
acagcatact aaatttccct cttcttcct ctagggtgtc gttaattacc cgtactaaag    2940
gtttggaaaa gaaaaagag accgcctcgt ttcttttct tcgtcgaaaa aggcaataaa    3000
aatttttatc acgtttcttt ttcttgaaaa ttttttttt gattttttc tctttcgatg    3060 acctcccatt gatatttaag ttaataaacg gtcttcaatt tctcaagttt cagtttcatt    3120
tttcttgttc tattacaact ttttttactt cttgctcatt agaaagaaag catagcaatc    3180
taatctaagt tttctagaac tagtatggca tctaacgaag ttttagtttt gagaggtacc    3240
ttggaaggtc acaacggttg ggtcacatct ttggctactt ctgctggtca accaaaccta    3300
ttgttgtccg cttcccgtga taagactttg atctcctgga agttgactgg tgacgaccaa    3360
aagtttggtg tcccagttag atcttttcaag ggtcacagtc acattgtcca agactgtact    3420
ttgactgctg acggtgctta cgcttttgtct gcttcttggg acaagacctt gagattatgg    3480
gatgttgcca ccggtgaaac ctaccaaaga ttcgtcggtc acaagtccga tgttatgtcc    3540
gttgacattg acaagaaggc ttccatgatt atctctggtt cccgtgacaa gaccatcaag    3600
gtctggacca tcaaaggtca atgtttggcc actttgttgg gtcacaatga ctgggtttcc    3660
caagtcagag ttgttccaaa cgaaaaagct gatgatgact ctgtcaccat catttctgcc    3720
ggtaacgaca aaatggttaa ggtatgtgat atattttctt tccatgatag aatatgatga    3780
caatcgagta aagaagaaa agtggatttg tgtatgccat tcaaatgatg taataacata    3840
tttgctactt cagatggaac tttgagttcc gaatgagaca taccaattat caccaagatc    3900
tctgatgaat ggtttagcat tactctgctc ttctctttac tcgttatgtc aaaatggaaa    3960
cttttttttt aaattaattt tgttcccctta ctaacaaaaa tgatataatg acaggcttgg    4020
aacttaaacc aattccaaat tgaagctgac ttcatcggtc acaactccaa catcaacact    4080
ttgactgctt ccccagacgg aactttgatt gcttccgctg gtaaggacgg tgaaattatg    4140
ttgtggaact tggctgctaa gaaggctatg tacactttgt ctgcctaaga tgaagttttc    4200
tctttggctt tctctccaaa cagatactgg ttggctgctg ccactgctac cggtattaag    4260
gtcttttctt tggaccccaca atactggtc gatgacttga gaccagaatt tgctggttac    4320
agcaaggccg ctgaaccaca tgctgttttct ttggcttggt ctgctgacgg tcaaactttg    4380
tttgccggtt acaccgacaa cgtcattaga gtttggcaag ttatgactgc taactaactc    4440
gagattagtt atgtcacgct tacattcacg ccctccccc acatccgctc taaccgaaaa    4500
```

```
ggaaggagtt agacaacctg aagtctaggt ccctatttat ttttttatag ttatgttagt    4560
attaagaacg ttatttatat ttcaaatttt tcttttttt ctgtacagac gcgtgtacgc    4620
atgtaacatt atactgaaaa ccttgcttga aaggttttg ggacgctcga aggctttaat    4680
ttgggtaccc aattcgccct atagtgagtc gtattacgcg cgctcactgg ccgtcgtttt    4740
acaacgtcgt gactgggaaa accctggcgt tacccaactt aatcgccttg cagcacatcc    4800 cccttcgcc agctggcgta atagcgaaga ggcccgcacc gatcgccctt cccaacagtt    4860
gcgcagcctg aatggcgaat ggcgcgacgc gccctgtagc ggcgcattaa gcgcggcggg    4920
tgtggtggtt acgcgcagcg tgaccgctac acttgccagc gccctagcgc ccgctccttt    4980
cgctttcttc ccttcctttc tcgccacgtt cgccggcttt ccccgtcaag ctctaaatcg    5040
ggggctccct ttagggttcc gatttagtgc tttacggcac ctcgacccca aaaaacttga    5100
ttagggtgat ggttcacgta gtgggccatc gccctgatag acggttttc gccctttgac    5160 gttggagtcc acgttcttta atagtggact cttgttccaa actggaacaa cactcaaccc    5220
tatctcggtc tattctttg atttataagg gatttgccg atttcggcct attggttaaa    5280
aaatgagctg atttaacaaa aatttaacgc gaattttaac aaaatattaa cgtttacaat    5340
ttcctgatgc ggtattttct ccttacgcat ctgtgcggta tttcacaccg catatcgacg    5400
gtcgaggaga acttctagta tatccacata cctaatatta ttgccttatt aaaaatggaa    5460
tcccaacaat tacatcaaaa tccacattct cttcaaaatc aattgtcctg tacttccttg    5520
ttcatgtgtg ttcaaaaacg ttatatttat aggataatta tactctattt ctcaacaagt    5580
aattggttgt ttggccgagc ggtctaaggc gcctgattca agaaatatct tgaccgcagt    5640
taactgtggg aatactcagg tatcgtaaga tgcaagagtt cgaatctctt agcaaccatt    5700
atttttttcc tcaacataac gagaacacac agggggcgcta tcgcacagaa tcaaattcga    5760
tgactggaaa ttttttgtta atttcagagg tcgcctgacg catataccttt ttcaactga    5820 aaaattggga gaaaaggaa aggtgagagg ccggaaccgg cttttcatat agaatagaga    5880
agcgttcatg actaaatgct tgcatcacaa tacttgaagt tgacaatatt atttaaggac    5940
ctattgtttt ttccaatagg tggttagcaa tcgtcttact ttctaacttt cttacctttt    6000
tacatttcag caatatatat atatatttca aggatatacc attctaatgt ctgcccctat    6060
gtctgcccct aagaagatcg tcgttttgcc aggtgaccac gttggtcaag aaatcacagc    6120
cgaagccatt aaggttctta agctatttc tgatgttcgt tccaatgtca agttcgattt    6180
cgaaaatcat ttaattggtg gtgctgctat cgatgctaca ggtgtcccac ttccagatga    6240
ggcgctggaa gcctccaaga aggttgatgc cgttttgtta ggtgctgtgg gtggtcctaa    6300
atggggtacc ggtagtgtta gacctgaaca aggtttacta aaaatccgta aagaacttca    6360
attgtacgcc aacttaagac catgtaactt tgcatccgac tctcttttag acttatctcc    6420
aatcaagcca caatttgcta aaggtactga cttcgttgtt gtcagagaat tagtgggagg    6480
tatttacttt ggtaagagaa aggaagacga tggtgatggt gtcgcttggg atagtgaaca    6540
atacaccgtt ccagaagtgc aaagaatcac aagaatggcc gctttcatgg ccctacaaca    6600
tgagccacca ttgcctattt ggtccttgga taaagctaat gttttggcct cttcaagatt    6660
atggagaaaa actgtggagg aaaccatcaa gaacgaattc cctacattga aggttcaaca    6720
tcaattgatt gattctgccg ccatgatcct agttaagaac ccaacccacc taatggtat    6780 tataatcacc agcaacatgt ttggtgatat catctccgat gaagcctccg ttatcccagg    6840
ttccttgggt ttgttgccat ctgcgtcctt ggcctctttg ccagacaaga acaccgcatt    6900
```

| | | |
|---|---|---|
| tggtttgtac gaaccatgcc acggttctgc tccagatttg ccaaagaata aggttgaccc | 6960 | |
| tatcgccact atcttgtctg ctgcaatgat gttgaaattg tcattgaact tgcctgaaga | 7020 | |
| aggtaaggcc attgaagatg cagttaaaaa ggttttggat gcaggtatca gaactggtga | 7080 | |
| tttaggtggt tccaacagta ccaccgaagt cggtgatgct gtcgccgaag aagttaagaa | 7140 | |
| aatccttgct taaaaagatt ctctttttt atgatatttg tacataaact ttataaatga | 7200 | |
| aattcataat agaaacgaca cgaaattaca aaatggaata tgttcatagg gtagacgaaa | 7260 | |
| ctatatacgc aatctacata catttatcaa gaaggagaaa aaggaggata gtaaaggaat | 7320 | |
| acaggtaagc aaattgatac taatggctca acgtgataag gaaaaagaat tgcactttaa | 7380 | |
| cattaatatt gacaaggagg agggcaccac acaaaaagtt aggtgtaaca gaaaatcatg | 7440 | |
| aaactacgat tcctaatttg atattggagg attttctcta aaaaaaaaaa aatacaacaa | 7500 | |
| ataaaaaaca ctcaatgacc tgaccatttg atggagttta agtcaatacc ttcttgaacc | 7560 | |
| atttcccata atggtgaaag ttccctcaag aattttactc tgtcagaaac ggccttacga | 7620 | |
| cgtagtcgat atggtgcact ctcagtacaa tctgctctga tgccgcatag ttaagccagc | 7680 | |
| cccgacaccc gccaacaccc gctgacgcgc cctgacgggc ttgtctgctc ccggcatccg | 7740 | |
| cttacagaca agctgtgacc gtctccggga gctgcatgtg tcagaggttt tcaccgtcat | 7800 | |
| caccgaaacg cgcga | 7815 | |

<210> SEQ ID NO 17
<211> LENGTH: 849
<212> TYPE: DNA
<213> ORGANISM: Artificial Sequence
<220> FEATURE:
<223> OTHER INFORMATION: Synthetic: Hbd

<400> SEQUENCE: 17

| | | |
|---|---|---|
| atgaaaaagg tatgtgttat aggtgcaggt actatgggtt caggaattgc tcaggcattt | 60 | |
| gcagctaaag gatttgaagt agtattaaga gatattaaag atgaatttgt tgatagagga | 120 | |
| ttagatttta tcaataaaaa tcttttctaaa ttagttaaaa aaggaaagat agaagaagct | 180 | |
| actaaagttg aaatcttaac tagaatttcc ggaacagttg accttaatat ggcagctgat | 240 | |
| tgcgatttag ttatagaagc agctgttgaa agaatggata ttaaaaagca gattttgct | 300 | |
| gacttagaca atatatgcaa gccagaaaca attcttgcat caaatacatc atcactttca | 360 | |
| ataacagaag tggcatcagc aactaaaaga cctgataagg ttataggtat gcatttcttt | 420 | |
| aatccagctc ctgttatgaa gcttgtagag gtaataagag gaatagctac atcacaagaa | 480 | |
| acttttgatg cagttaaaga gacatctata gcaataggaa aagatcctgt agaagtagca | 540 | |
| gaagcaccag gatttgttgt aaatagaata ttaataccaa tgattaatga agcagttggt | 600 | |
| atattagcag aaggaatagc ttcagtagaa gacatagata aagctatgaa acttggagct | 660 | |
| aatcacccaa tgggaccatt agaattaggt gatttatag gtcttgatat atgtcttgct | 720 | |
| ataatggatg tttttatactc agaaactgga gattctaagt atagaccaca tacattactt | 780 | |
| aagaagtatg taagagcagg atggcttgga agaaaatcag gaaaaggttt ctacgattat | 840 | |
| tcaaaataa | 849 | |

<210> SEQ ID NO 18
<211> LENGTH: 786
<212> TYPE: DNA
<213> ORGANISM: Artificial Sequence
<220> FEATURE:

<223> OTHER INFORMATION: Synthetic: Crt

<400> SEQUENCE: 18

| | |
|---|---|
| atggaactaa acaatgtcat ccttgaaaag gaaggtaaag ttgctgtagt taccattaac | 60 |
| agacctaaag cattaaatgc gttaaatagt gatacactaa agaaatgga ttatgttata | 120 |
| ggtgaaattg aaaatgatag cgaagtactt gcagtaattt taactggagc aggagaaaaa | 180 |
| tcatttgtag caggagcaga tatttctgag atgaaggaaa tgaataccat tgaaggtaga | 240 |
| aaattcggga tacttggaaa taaagtgttt agaagattag aacttcttga aaagcctgta | 300 |
| atagcagctg ttaatggttt tgctttagga ggcggatgcg aaatagctat gtcttgtgat | 360 |
| ataagaatag cttcaagcaa cgcaagattt ggtcaaccag aagtaggtct cggaataaca | 420 |
| cctggttttg gtggtacaca aagactttca agattagttg aatgggcat ggcaaagcag | 480 |
| cttatattta ctgcacaaaa tataaaggca gatgaagcat taagaatcgg acttgtaaat | 540 |
| aaggtagtag aacctagtga attaatgaat acagcaaaag aaattgcaaa caaaattgtg | 600 |
| agcaatgctc cagtagctgt taagttaagc aaacaggcta ttaatagagg aatgcagtgt | 660 |
| gatattgata ctgctttagc atttgaatca gaagcatttg gagaatgctt ttcaacagag | 720 |
| gatcaaaagg atgcaatgac agctttcata gagaaaagaa aaattgaagg cttcaaaaat | 780 |
| agatag | 786 |

<210> SEQ ID NO 19
<211> LENGTH: 1173
<212> TYPE: DNA
<213> ORGANISM: Artificial Sequence
<220> FEATURE:
<223> OTHER INFORMATION: Synthetic: BdhB

<400> SEQUENCE: 19

| | |
|---|---|
| atggttgatt tcgaatattc aataccaact agaatttttt tcggtaaaga taagataaat | 60 |
| gtacttggaa gagagcttaa aaaatatggt tctaaagtgc ttatagttta tggtggagga | 120 |
| agtataaaga gaatggaat atatgataaa gctgtaagta tacttgaaaa aaacagtatt | 180 |
| aaattttatg aacttgcagg agtagagcca aatccaagag taactacagt tgaaaaagga | 240 |
| gttaaaatat gtagagaaaa tggagttgaa gtagtactag ctataggtgg aggaagtgca | 300 |
| atagattgcg caaaggttat agcagcagca tgtgaatatg atggaaatcc atggatatt | 360 |
| gtgttagatg gctcaaaaat aaaaagggtg cttcctatag ctagtatatt aaccattgct | 420 |
| gcaacaggat cagaaatgga tacgtgggca gtaataaata tatggatac aaacgaaaaa | 480 |
| ctaattgcgg cacatccaga tatggctcct aagttttcta ttagatccc aacgtatacg | 540 |
| tataccgtac ctaccaatca acagcagca ggaacagctg atattatgag tcatatattt | 600 |
| gaggtgtatt ttagtaatac aaaaacagca tatttgcagg atagaatggc agaagcgtta | 660 |
| ttaagaactt gtattaaata tggaggaata gctcttgaga gccggatga ttatgaggca | 720 |
| agagccaatc taatgtgggc ttcaagtctt gcgataaatg gacttttaac atatggtaaa | 780 |
| gacactaatt ggagtgtaca cttaatggaa catgaattaa gtgcttatta cgacataaca | 840 |
| cacggcgtag gcttgcaat tttaacaccct aattggatgg agtatatttt aaataatgat | 900 |
| acagtgtaca gtttgttga atatggtgta aatgtttggg aatagacaa agaaaaaaat | 960 |
| cactatgaca tagcacatca agcaatacaa aaaacaagag attactttgt aaatgtacta | 1020 |
| ggtttaccat ctagactgag agatgttgga attgaagaag aaaaattgga cataatggca | 1080 |
| aaggaatcag taaagcttac aggaggaacc ataggaaacc taagaccagt aaacgcctcc | 1140 |

```
gaagtcctac aaatattcaa aaaatctgtg taa                                   1173
```

<210> SEQ ID NO 20
<211> LENGTH: 1197
<212> TYPE: DNA
<213> ORGANISM: Artificial Sequence
<220> FEATURE:
<223> OTHER INFORMATION: Synthetic: Erg10

<400> SEQUENCE: 20

```
atgtctcaga acgtttacat tgtatcgact gccagaaccc caattggttc attccagggt     60
tctctatcct ccaagacagc agtggaattg ggtgctgttg ctttaaaagg cgccttggct    120
aaggttccag aattggatgc atccaaggat tttgacgaaa ttattttggg taacgttctt    180
tctgccaatt gggccaagc tccggccaga caagttgctt tggctgccgg tttgagtaat     240
catatcgttg caagcacagt taacaaggtc tgtgcatccg ctatgaaggc aatcattttg    300
ggtgctcaat ccatcaaatg tggtaatgct gatgttgtcg tagctggtgg ttgtgaatct    360
atgactaacg caccatacta catgccagca gcccgtgcgg gtgccaaatt tggccaaact    420
gttcttgttg atggtgtcga aagagatggg ttgaacgatg cgtacgatgg tctagccatg    480
ggtgtacacg cagaaaagtg tgcccgtgat tgggatatta ctagagaaca acaagacaat    540
tttgccatcg aatcctacca aaatctcaa aaatctcaaa aggaaggtaa attcgacaat     600
gaaattgtac ctgttaccat taagggattt agaggtaagc ctgatactca agtcacgaag    660
gacgaggaac ctgctagatt acacgttgaa aaattgagat ctgcaaggac tgttttccaa    720
aaagaaaacg gtactgttac tgccgctaac gcttctccaa tcaacgatgg tgctgcagcc    780
gtcatcttgg tttccgaaaa agttttgaag gaaaagaatt tgaagccttt ggctattatc    840
aaaggttggg gtgaggccgc tcatcaacca gctgatttta catgggctcc atctcttgca    900
gttccaaagg ctttgaaaca tgctggcatc gaagacatca attctgttga ttactttgaa    960
ttcaatgaag cctttcggt tgtcggtttg gtgaacacta agattttgaa gctagaccca    1020
tctaaggtta atgtatatgg tggtgctgtt gctctaggtc acccattggg ttgttctggt   1080
gctagagtgg ttgttacact gctatccatc ttacagcaag aaggaggtaa gatcggtgtt   1140
gccgccattt gtaatggtgg tggtggtgct cctctattg tcattgaaaa gatatga      1197
```

<210> SEQ ID NO 21
<211> LENGTH: 1119
<212> TYPE: DNA
<213> ORGANISM: Artificial Sequence
<220> FEATURE:
<223> OTHER INFORMATION: Synthetic: Etr1

<400> SEQUENCE: 21

```
atgtcgtcct cagctcatca gattcccaag cacttcaaat cgctcatcta ttcaactcat     60
gaagttgagg attgtaccaa ggttttgtca gtgaaaaatt atacgcctaa acaagactta    120
tctcaatcaa ttgtgttaaa aactttggcc tttcccataa acccttcgga tatcaatcag    180
ttgcaaggag tatacccgtc tcgtccagaa aagacatacg attactccac agatgagcca    240
gccgctatcg ccggtaatga gggtgtcttt gaagttgttt ctttaccttc gggaagttcc    300
aagggagatt tgaaattggg tgaccgagtt atcccattgc aggcaaatca agggacttgg    360
tccaattata gagttttctc tagtagttct gatttaatca aggtaaatga tttggatctg    420
ttttctgcgg caactgtatc tgttaatggt tgtaccggtt tccaattagt atcagactat    480
```

```
atcgactgga acagtaacgg taatgaatgg attatccaaa atgccggtac atctagtgta      540
tcaaaaatag ttacgcaagt agcaaaagct aaagggatca aaacattaag tgttatacgt      600
gaccgtgata attttgatga ggtagcaaaa gttttggagg ataagtatgg tgctacgaag      660
gttatttccg aatcgcaaaa caacgacaag acttttgcca agaagtatt gtccaagatt       720 ttgggtgaaa atgcaagggt gaggcttgcc ttgaattctg ttggaggtaa atccagtgca     780
tcaatagcac gtaagttgga aaataatgct ttgatgctca cttatggagg aatgtcaaaa     840
caacctgtaa ctttaccaac atctctacac attttcaaag gcttgacatc caaagggtac     900
tgggtgactg aaaagaacaa aaaaaacccc caaagcaaga ttgacaccat cagtgatttt      960
atcaaaatgt ataattatgg tcacattatt tcaccaagag atgaaattga aactcttacc     1020
tggaatacta acactactac tgacgaacag ttactagaac tagtcaaaaa aggtataact     1080
gggaagggga agaaaaaaat ggttgtttta gaatggtaa                            1119

<210> SEQ ID NO 22
<211> LENGTH: 1404
<212> TYPE: DNA
<213> ORGANISM: Artificial Sequence
<220> FEATURE:
<223> OTHER INFORMATION: Synthetic:  EutE

<400> SEQUENCE: 22
atgaatcaac aggatattga acaggtggtg aaagcggtac tgctgaaaat gcaaagcagt       60
gacacgccgt ccgccgccgt tcatgagatg ggcgtttttcg cgtccctgga tgacgccgtt     120
gcggcagcca aagtcgccca gcaagggtta aaaagcgtgg caatgcgcca gttagccatt     180
gctgccattc gtgaagcagg cgaaaaacac gccagagatt tagcggaact gccgtcagt      240 gaaaccggca tggggcgcgt tgaagataaa tttgcaaaaa acgtcgctca ggcgcgcggc     300
acaccaggcg ttgagtgcct ctctccgcaa gtgctgactg cgacaacgg cctgacccta     360 attgaaaacg cacccctgggg cgtggtggct tcggtgacgc cttccactaa cccggcggca     420
accgtaatta caacgccat cagcctgatt gccgcgggca acagcgtcat ttttgccccg       480
catccggcgg cgaaaaagt ctcccagcgg gcgattacgc tgctcaacca ggcgattgtt      540
gccgcaggtg ggccggaaaa cttactggtt actgtggcaa atccggatat cgaaaccgcg     600
caacgcttgt tcaagtttcc gggtatcggc ctgctggtgg taaccggcgg cgaagcggta     660
gtagaagcgg cgcgtaaaca caccaataaa cgtctgattg ccgcaggcgc tggcaacccg     720
ccggtagtgg tggatgaaac cgccgacctc gccgtgccg ctcagtccat cgtcaaaggc     780 gcttcttcg ataacaacat catttgtgcc gacgaaaagg tactgattgt tgttgatagc     840
gtagccgatg aactgatgcg tctgatggaa ggccagcacg cggtgaaact gaccgcagaa     900
caggcgcagc agctgcaacc ggtgttgctg aaaaatatcg acgagcgcgg aaaaggcacc     960
gtcagccgtg actgggttgg tcgcgacgca ggcaaaatcg cggcggcaat cggccttaaa    1020
gttccgcaag aaacgcgcct gctgtttgtg gaaaccaccg cagaacatcc gtttgccgtg    1080
actgaactga tgatgccggt gttgcccgtc gtgcgcgtcg ccaacgtggc ggatgccatt    1140
gcgctagcgg tgaaactgga aggcggttgc caccacacgg cggcaatgca ctcgcgcaac    1200
atcgaaaaca tgaaccagat ggcgaatgct attgatacca gcattttcgt taagaacgga    1260
ccgtgcattg ccgggctggg gctgggcggg gaaggctgga ccaccatgac catcaccacg    1320
ccaaccggtg aaggggtaac cagcgcgcgt acgtttgtcc gtctgcgtcg ctgtgtatta    1380
gtcgatgcgt tcgcattgt ttaa                                             1404
```

<210> SEQ ID NO 23
<211> LENGTH: 8657
<212> TYPE: DNA
<213> ORGANISM: Artificial Sequence
<220> FEATURE:
<223> OTHER INFORMATION: Synthetic:
    p423-GPDp-CaHbd-PRM9t-TEF1p-CaCrt-CPS1t

<400> SEQUENCE: 23

```
gacgaaaggg cctcgtgata cgcctatttt tataggttaa tgtcatgata ataatggttt      60
cttagtatga tccaatatca aaggaaatga tagcattgaa ggatgagact aatccaattg     120
aggagtggca gcatatagaa cagctaaagg gtagtgctga aggaagcata cgatacccg     180
catggaatgg gataatatca caggaggtac tagactacct ttcatcctac ataaatagac     240
gcatataagt acgcatttaa gcataaacac gcactatgcc gttcttctca tgtatatata     300
tatacaggca acacgcagat ataggtgcga cgtgaacagt gagctgtatg tgcgcagctc     360
gcgttgcatt ttcggaagcg ctcgttttcg gaaacgcttt gaagttccta ttccgaagtt     420
cctattctct agaaagtata ggaacttcag agcgcttttg aaaaccaaaa gcgctctgaa     480
gacgcacttt caaaaaacca aaaacgcacc ggactgtaac gagctactaa atattgcga     540
ataccgcttc cacaaacatt gctcaaaagt atctctttgc tatatatctc tgtgctatat     600
ccctatataa cctacccatc cacctttcgc tccttgaact tgcatctaaa ctcgacctct     660
acatttttta tgtttatctc tagtattact ctttagacaa aaaaattgta gtaagaacta     720
ttcatagagt gaatcgaaaa caatacgaaa atgtaaacat ttcctatacg tagtatatag     780
agacaaaata gaagaaaccg ttcataattt tctgaccaat gaagaatcat caacgctatc     840
actttctgtt cacaaagtat gcgcaatcca catcggtata gaatataatc ggggatgcct     900
ttatcttgaa aaatgcacc cgcagcttcg ctagtaatca gtaaacgcgg gaagtggagt     960
caggcttttt ttatggaaga gaaaatagac accaaagtag ccttcttcta accttaacgg    1020
acctacagtg caaaaagtta tcaagagact gcattataga gcgcacaaag gagaaaaaaa    1080
gtaatctaag atgctttgtt agaaaaatag cgctctcggg atgcattttt gtagaacaaa    1140
aaagaagtat agattctttg ttggtaaaat agcgctctcg cgttgcattt ctgttctgta    1200
aaaatgcagc tcagattctt tgtttgaaaa attagcgctc tcgcgttgca ttttttgtttt    1260
acaaaaatga agcacagatt cttcgttggt aaaatagcgc tttcgcgttg catttctgtt    1320
ctgtaaaaat gcagctcaga ttctttgttt gaaaaattag cgctctcgcg ttgcattttt    1380
gttctacaaa atgaagcaca gatgcttcgt tcaggtggca cttttcgggg aaatgtgcgc    1440
ggaacccta tttgtttatt tttctaaata cattcaaata tgtatccgct catgagacaa    1500
taaccctgat aaatgcttca ataatattga aaaaggaaga gtatgagtat tcaacatttc    1560
cgtgtcgccc ttattccctt ttttgcggca ttttgccttc ctgttttgc tcacccagaa    1620
acgctggtga agtaaaaga tgctgaagat cagttgggtg cacagtggg ttacatcgaa    1680
ctggatctca acagcggtaa gatccttgag agttttcgcc ccgaagaacg ttttccaatg    1740
atgagcactt ttaaagttct gctatgtggc gcggtattat cccgtattga cgccgggcaa    1800
gagcaactcg gtcgccgcat acactattct cagaatgact tggttgagta ctcaccagtc    1860
acagaaaagc atcttacgga tggcatgaca gtaagagaat tatgcagtgc tgccataacc    1920
atgagtgata acactgcggc caacttactt ctgacaacga tcgaggacc gaaggagcta    1980
accgcttttt tgcacaacat ggggatcat gtaactcgcc ttgatcgttg gaaccggag    2040
```

```
ctgaatgaag ccataccaaa cgacgagcgt gacaccacga tgcctgtagc aatggcaaca    2100
acgttgcgca aactattaac tggcgaacta cttactctag cttcccggca acaattaata    2160
gactggatgg aggcggataa agttgcagga ccacttctgc gctcggccct tccggctggc    2220
tggtttattg ctgataaatc tggagccggt gagcgtgggt ctcgcggtat cattgcagca    2280
ctggggccag atggtaagcc ctcccgtatc gtagttatct acacgacggg gagtcaggca    2340
actatggatg aacgaaatag acagatcgct gagataggtg cctcactgat taagcattgg    2400
taactgtcag accaagttta ctcatatata ctttagattg atttaaaact tcattttaa    2460 tttaaaagga tctaggtgaa gatcctttt gataatctca tgaccaaaat cccttaacgt    2520
gagttttcgt tccactgagc gtcagacccc gtagaaaaga tcaaaggatc ttcttgagat    2580 ccttttttc tgcgcgtaat ctgctgcttg caaacaaaaa aaccaccgct accagcggtg    2640
gtttgtttgc cggatcaaga gctaccaact ctttttccga aggtaactgg cttcagcaga    2700
gcgcagatac caaatactgt ccttctagtg tagccgtagt taggccacca cttcaagaac    2760
tctgtagcac cgcctacata cctcgctctg ctaatcctgt taccagtggc tgctgccagt    2820
ggcgataagt cgtgtcttac cgggttggac tcaagacgat agttaccgga taaggcgcag    2880
cggtcgggct gaacggggg ttcgtgcaca gcccagct tggagcgaac gacctacacc    2940
gaactgagat acctacagcg tgagctatga gaaagcgcca cgcttcccga agggagaaag    3000
gcggacaggt atccggtaag cggcagggtc ggaacaggag agcgcacgag ggagcttcca    3060
gggggaaacg cctggtatct ttatagtcct gtcgggtttc gccacctctg acttgagcgt    3120
cgatttttgt gatgctcgtc aggggggcgg agcctatgga aaaacgccag caacgcggcc    3180 ttttacggt tcctggcctt ttgctggcct tttgctcaca tgttctttcc tgcgttatcc    3240
cctgattctg tggataaccg tattaccgcc tttgagtgag ctgataccgc tcgccgcagc    3300
cgaacgaccg agcgcagcga gtcagtgagc gaggaagcgg aagagcgccc aatacgcaaa    3360
ccgcctctcc ccgcgcgttg gccgattcat taatgcagct ggcacgacag gtttcccgac    3420
tggaaagcgg gcagtgagcg caacgcaatt aatgtgagtt acctcactca ttaggcaccc    3480
caggctttac actttatgct tccggctcct atgttgtgtg gaattgtgag cggataacaa    3540
tttcacacag gaaacagcta tgaccatgat tacgccaagc gcgcaattaa ccctcactaa    3600
agggaacaaa agctggagct cagtttatca ttatcaatac tcgccatttc aaagaatacg    3660
taaataatta atagtagtga ttttcctaac tttatttagt caaaaaatta gccttttaat    3720
tctgctgtaa cccgtacatg cccaaaatag ggggcgggtt acacagaata tataacatcg    3780
taggtgtctg ggtgaacagt ttattcctgg catccactaa atataatgga gcccgctttt    3840
taagctggca tccagaaaaa aaagaatcc cagcaccaaa atattgtttt cttccaac    3900 catcagttca taggtccatt ctcttagcgc aactacagag aacagggca caaacaggca    3960 aaaacgggc acaacctcaa tggagtgatg caacctgcct ggagtaaatg atgacacaag    4020
gcaattgacc cacgcatgta tctatctcat tttcttacac cttctattac cttctgctct    4080
ctctgatttg gaaaaagctg aaaaaaaagg ttgaaccag ttccctgaaa ttattcccct    4140
acttgactaa taagtatata aagacggtag gtattgattg taattctgta aatctatttc    4200
ttaaacttct taaattctac ttttatagtt agtcttttt ttagttttaa aacaccagaa    4260
cttagtttcg acggattcta gaactagtat gaaaaaggta tgtgttatag gtgcaggtac    4320
tatgggttca ggaattgctc aggcatttgc agctaaagga tttgaagtag tattaagaga    4380
```

```
tattaaagat gaatttgttg atagaggatt agattttatc aataaaaatc tttctaaatt    4440
agttaaaaaa ggaaagatag aagaagctac taaagttgaa atcttaacta gaatttccgg    4500
aacagttgac cttaatatgg cagctgattg cgatttagtt atagaagcag ctgttgaaag    4560
aatggatatt aaaaagcaga ttttgtctga cttagacaat atatgcaagc cagaaacaat    4620
tcttgcatca aatacatcat cactttcaat aacagaagtg gcatcagcaa ctaaaagacc    4680
tgataaggtt ataggtatgc atttctttaa tccagctcct gttatgaagc ttgtagaggt    4740
aataagagga atagctacat cacaagaaac ttttgatgca gttaaagaga catctatagc    4800
aataggaaaa gatcctgtag aagtagcaga agcaccagga tttgttgtaa atagaatatt    4860
aataccaatg attaatgaag cagttggtat attagcagaa ggaatagctt cagtagaaga    4920
catagataaa gctatgaaac ttggagctaa tcacccaatg ggaccattag aattaggtga    4980
ttttataggt cttgatatat gtcttgctat aatggatgtt ttatactcag aaactggaga    5040
ttctaagtat agaccacata cattacttaa gaagtatgta agagcaggat ggcttggaag    5100
aaaatcagga aaaggtttct acgattattc aaaataagtc gacacagaag acgggagaca    5160
ctagcacaca actttaccag gcaaggtatt tgacgctagc atgtgtccaa ttcagtgtca    5220
tttatgattt tttgtagtag gatataaata tatacagcgc tccaaatagt gcggttgccc    5280
caaaaacacc acggaacctc atctgttctc gtactttgtt gtgacaaagt agctcactgc    5340
cttattatca catttttcatt atgcaacgct tcggaaaata cgatgttgaa atcatagct    5400 tcaaaatgtt tctactcctt ttttactctt ccagattttc tcggactccg cgcatcgccg    5460
taccacttca aaacacccaa gcacagcata ctaaatttcc cctctttctt cctctagggt    5520
gtcgttaatt acccgtacta aaggtttgga aagaaaaaa gagaccgcct cgtttctttt    5580
tcttcgtcga aaaaggcaat aaaaattttt atcacgtttc tttttcttga aatttttttt    5640
tttgattttt ttctctttcg atgacctccc attgatattt aagttaataa acggtcttca    5700
atttctcaag tttcagtttc attttctttg ttctattaca acttttttta cttcttgctc    5760
attagaaaga aagcatagca atctaatcta agtctagaac tagtatggaa ctaaacaatg    5820
tcatccttga aaaggaaggt aaagttgctg tagttaccat taacagacct aaagcattaa    5880
atgcgttaaa tagtgataca ctaaaagaaa tggattatgt tataggtgaa attgaaaatg    5940
atagcgaagc acttgcagta atttttaactg gagcaggaga aaaatcattt gtagcaggag    6000
cagatatttc tgagatgaag gaaatgaata ccattgaagg tagaaaattc gggatacttg    6060
gaaataaagt gtttagaaga ttagaacttc ttgaaaagcc tgtaatagca gctgttaatg    6120
gttttgcttt aggaggcgga tgcgaaatag ctatgtcttg tgatataaga atagcttcaa    6180
gcaacgcaag atttggtcaa ccagaagtag gtctcggaat aacacctggt tttggtggta    6240
cacaaagact ttcaagatta gttggaatgg gcatggcaaa gcagcttata tttactgcac    6300
aaaatataaa ggcagatgaa gcattaagaa tcggacttgt aaataaggta gtagaaccta    6360
gtgaattaat gaatacagca aaagaaattg caaacaaaat tgtgagcaat gctccagtag    6420
ctgttaagtt aagcaaacag gctattaata gaggaatgca gtgtgatatt gatactgctt    6480
tagcatttga atcagaagca tttgagaat gcttttcaac agaggatcaa aaggatgcaa    6540
tgacagcttt catagagaaa agaaaaattg aaggcttcaa aaatagatag gtcgacgcgc    6600
aatgattgaa tagtcaaaga tttttttttt ttaattttt tttttttaatt tttttttttt    6660 ttcatagaac tttttattta aataaatcac gtctatatat gtatcagtat aacgtaaaaa    6720
aaaaaacacc gtcagttaaa caaaacataa ataaaaaaaa aagaagtgt caaatcaagt     6780
```

```
gtcaaatcgg ccggtaccca attcgcccta tagtgagtcg tattacgcgc gctcactggc    6840
cgtcgtttta caacgtcgtg actgggaaaa ccctggcgtt acccaactta atcgccttgc    6900
agcacatccc cctttcgcca gctggcgtaa tagcgaagag gcccgcaccg atcgcccttc    6960
ccaacagttg cgcagcctga atggcgaatg gcgcgacgcg ccctgtagcg cgcattaag     7020 cgcggcgggt gtggtggtta cgcgcagcgt gaccgctaca cttgccagcg ccctagcgcc    7080
cgctcctttc gctttcttcc cttcctttct cgccacgttc gccggctttc cccgtcaagc    7140
tctaaatcgg gggctcccctt tagggttccg atttagtgct ttacggcacc tcgaccccaa    7200
aaaacttgat tagggtgatg gttcacgtag tgggccatcg ccctgataga cggttttttcg    7260 ccctttgacg ttggagtcca cgttctttaa tagtggactc ttgttccaaa ctggaacaac    7320
actcaaccct atctcggtct attcttttga tttataaggg attttgccga tttcggccta    7380
ttggttaaaa aatgagctga tttaacaaaa atttaacgcg aattttaaca aaatattaac    7440
gtttacaatt tcctgatgcg gtattttctc cttacgcatc tgtgcggtat ttcacaccgc    7500
atagggtaat aactgatata attaaattga agctctaatt tgtgagttta gtatacatgc    7560
atttacttat aatacagttt tctacataag aacacctttg gtggagggaa catcgttggt    7620
accattgggc gaggtggctt ctcttatggc aaccgcaaga gccttgaacg cactctcact    7680
acggtgatga tcattcttgc ctcgcagaca atcaacgtgg agggtaattc tgctagcctc    7740
tgcaaagctt tcaagaaaat gcgggatcat ctcgcaagag agatctccta ctttctccct    7800
ttgcaaacca agttcgacaa ctgcgtacgg cctgttcgaa agatctacca ccgctctgga    7860
aagtgcctca tccaaaggcg caaatcctga tccaaacctt tttactccac gcgccagtag    7920
ggcctcttta aaagcttgac cgagagcaat cccgcagtct tcagtggtgt gatggtcgtc    7980
tatgtgtaag tcaccaatgc actcaacgat tagcgaccag ccggaatgct tggccagagc    8040
atgtatcata tggtccagaa acctatacc  tgtgtggacg ttaatcactt gcgattgtgt    8100
ggcctgttct gctactgctt ctgcctcttt ttctgggaag atcgagtgct ctatcgctag    8160
gggaccaccc tttaaagaga tcgcaatctg aatcttggtt tcatttgtaa tacgctttac    8220
tagggctttc tgctctgtca tgatttatct tcgtttcctg caggtttttg ttctgtgcag    8280
ttgggttaag aatactgggc aatttcatgt ttcttcaaca ctacatatgc gtatatatac    8340
caatctaagt ctgtgctcct tccttcgttc ttccttctgt tcggagatta ccgaatcaaa    8400
aaaatttcaa agaaaccgaa atcaaaaaaa agaataaaaa aaaaatgatg aattgaattg    8460
aaaagctgtg gtatggtgca ctctcagtac aatctgctct gatgccgcat agttaagcca    8520
gccccgacac ccgccaacac ccgctgacgc gccctgacgg gcttgtctgc tcccggcatc    8580
cgcttacaga caagctgtga ccgtctccgg gagctgcatg tgtcagaggt tttcaccgtc    8640
atcaccgaaa cgcgcga                                                  8657
```

<210> SEQ ID NO 24
<211> LENGTH: 9755
<212> TYPE: DNA
<213> ORGANISM: Artificial Sequence
<220> FEATURE:
<223> OTHER INFORMATION: Synthetic:
      p426-PGKp-EcEutE-CYC1t-CYC1p-CaBdhb-SPG5t

<400> SEQUENCE: 24

```
acgcacagat attataacat ctgcataata ggcatttgca agaattactc gtgagtaagg     60
aaagagtgag gaactatcgc atacctgcat ttaaagatgc cgatttgggc gcgaatcctt    120
```

```
tatttttggct tcaccctcat actattatca gggccagaaa aaggaagtgt ttccctcctt      180
cttgaattga tgttaccctc ataaagcacg tggcctctta tcgagaaaga aattaccgtc      240
gctcgtgatt tgtttgcaaa aagaacaaaa ctgaaaaaac ccagacacgc tcgacttcct      300
gtcttcctat tgattgcagc ttccaatttc gtcacacaac aaggtcctag cgacggctca      360
caggttttgt aacaagcaat cgaaggttct ggaatggcgg gaaagggttt agtaccacat      420
gctatgatgc ccactgtgat ctccagagca aagttcgttc gatcgtactg ttactctctc      480
tctttcaaac agaattgtcc gaatcgtgtg acaacaacag cctgttctca cacactcttt      540
tcttctaacc aagggggtgg tttagtttag tagaacctcg tgaaacttac atttacatat      600
atataaactt gcataaattg gtcaatgcaa gaaatacata tttggtcttt tctaattcgt      660
agtttttcaa gttcttagat gctttctttt tctcttttt acagatcatc aaggaagtaa       720
ttatctactt tttacaacaa atataaaaca tctagaacta gtatgaatca acaggatatt      780
gaacaggtgg tgaaagcggt actgctgaaa atgcaaagca gtgacacgcc gtccgccgcc      840
gttcatgaga tgggcgtttt cgcgtccctg gatgacgccg ttgcggcagc caaagtcgcc      900
cagcaaggga taaaaagcgt ggcaatgcgc cagttagcca ttgctgccat tcgtgaagca      960
ggcgaaaaac acgccagaga tttagcggaa cttgccgtca gtgaaaccgg catggggcgc     1020
gttgaagata aatttgcaaa aaacgtcgct caggcgcgcg gcacaccagg cgttgagtgc     1080
ctctctccgc aagtgctgac tggcgacaac ggcctgaccc taattgaaaa cgcaccctgg     1140
ggcgtggtgg cttcggtgac gccttccact aacccggcgg caaccgtaat taacaacgcc     1200
atcagcctga ttgccgcggg caacagcgtc atttttgccc cgcatccggc ggcgaaaaaa     1260
gtctcccagc gggcgattac gctgctcaac caggcgattg ttgccgcagg tgggccggaa     1320
aacttactgg ttactgtggc aaatccggat atcgaaaccg cgcaacgctt gttcaagttt     1380
ccgggtatcg gcctgctggt ggtaaccggc ggcgaagcgg tagtagaagc ggcgcgtaaa     1440
cacaccaata acgtctgat tgccgcaggc gctggcaacc cgccggtagt ggtggatgaa     1500
accgccgacc tcgcccgtgc cgctcagtcc atcgtcaaag cgcttctttc cgataacaac     1560
atcatttgtg ccgacgaaaa ggtactgatt gttgttgata gcgtagccga tgaactgatg     1620
cgtctgatgg aaggccagca gcggtgaaaa ctgaccgcag aacaggcgca gcagctgcaa     1680
ccggtgttgc tgaaaaatat cgacgagcgc ggaaaaggca ccgtcagccg tgactgggtt     1740
ggtcgcgacg caggcaaaat cgcggcggca atcggcctta agttccgca agaaacgcgc      1800 ctgctgtttg tggaaaccac cgcagaacat ccgtttgccg tgactgaact gatgatgccg     1860
gtgttgcccg tcgtgcgcgt cgccaacgtg gcggatgcca ttgcgctagc ggtgaaactg     1920
gaaggcggtt gccaccacac ggcggcaatg cactcgcgca acatcgaaaa catgaaccag     1980
atggcgaatg ctattgatac cagcatttc gttaagaacg gaccgtgcat tgccgggctg      2040
gggctgggcg gggaaggctg gaccaccatg accatcacca cgccaaccgg tgaaggggta     2100
accagcgcgc gtacgtttgt ccgtctgcgt cgctgtgtat tagtcgatgc gtttcgcatt     2160
gtttaaaagc ttatcgatac cgtcgacctc gagattagtt atgtcacgct tacattcacg     2220 ccctccccc acatccgctc taaccgaaaa ggaaggagtt agacaacctg aagtctaggt      2280
ccctatttat ttttttatag ttatgttagt attaagaacg ttatttatat ttcaaatttt     2340
tctttttttt ctgtacagac gcgtgtacgc atgtaacatt atactgaaaa ccttgcttga     2400
gaaggttttg ggacgctcga aggctttaat ttgagctcat ttggcgagcg ttggttggtg     2460
```

```
gatcaagccc acgcgtaggc aatcctcgag cagatccgcc aggcgtgtat atatagcgtg    2520
gatggccagg caactttagt gctgacacat acaggcatat atatatgtgt gcgacgacac    2580
atgatcatat ggcatgcatg tgctctgtat gtatataaaa ctcttgtttt cttcttttct    2640
ctaaatattc tttccttata cattaggacc tttgcagcat aaattactat acttctatag    2700
acacgcaaac acaaatacac acactaatct agaaatggtt gatttcgaat attcaatacc    2760
aactagaatt tttttcggta aagataagat aaatgtactt ggaagagagc ttaaaaaata    2820
tggttctaaa gtgcttatag tttatggtgg aggaagtata aagagaaatg gaatatatga    2880
taaagctgta agtatacttg aaaaaaacag tattaaattt tatgaacttg caggagtaga    2940
gccaaatcca agagtaacta cagttgaaaa aggagttaaa atatgtagag aaaatggagt    3000
tgaagtagta ctagctatag gtggaggaag tgcaatagat tgcgcaaagg ttatagcagc    3060
agcatgtgaa tatgatggaa atccatggga tattgtgtta gatggctcaa aaataaaaag    3120
ggtgcttcct atagctagta tattaaccat tgctgcaaca ggatcagaaa tggatacgtg    3180
ggcagtaata aataatatgg atacaaacga aaaactaatt gcggcacatc cagatatggc    3240
tcctaagttt tctatattag atccaacgta tacgtatacc gtacctacca atcaaacagc    3300
agcaggaaca gctgatatta tgagtcatat atttgaggtg tattttagta atacaaaaac    3360
agcatatttg caggatagaa tggcagaagc gttattaaga acttgtatta aatatggagg    3420
aatagctctt gagaagccgg atgattatga ggcaagagcc aatctaatgt gggcttcaag    3480
tcttgcgata aatggacttt aacatatgg taaagacact aattggagtg tacacttaat    3540
ggaacatgaa ttaagtgctt attacgacat aacacacggc gtagggcttg caatttaac    3600 acctaattgg atggagtata ttttaaataa tgatacagtg tacaagtttg ttgaatatgg    3660
tgtaaatgtt tggggaatag acaaagaaaa aaatcactat gacatagcac atcaagcaat    3720
acaaaaaaca agagattact ttgtaaatgt actaggttta ccatctagac tgagagatgt    3780
tggaattgaa gaagaaaaat tggacataat ggcaaaggaa tcagtaaagc ttacaggagg    3840
aaccatagga aacctaagac cagtaaacgc ctccgaagtc ctacaaatat tcaaaaaatc    3900
tgtgtaacca aagacgttgt ttcatcgcgc tattaccaag aaggttactt tacttgttct    3960
tgcacatgga cgcacgttgt gtgttcatat atatatatat atatatatat atatatttgt    4020
gcttgttttc attgtctcta tagttaatac attctatttt tatcgttata tttgcattct    4080
cttcgcataa aaacttcatg aaaattcggc agaaaataag ccggccggta cccaattcgc    4140
cctatagtga gtcgtattac gcgcgctcac tggccgtcgt tttacaacgt cgtgactggg    4200
aaaaccctgg cgttacccaa cttaatcgcc ttgcagcaca tccccctttc gccagctggc    4260
gtaatagcga agaggcccgc accgatcgcc cttcccaaca gttgcgcagc ctgaatggcg    4320
aatggcgcga cgcgccctgt agcggcgcat taagcgcggc gggtgtggtg gttacgcgca    4380
gcgtgaccgc tacacttgcc agcgccctag cgcccgctcc tttcgctttc ttcccttcct    4440
ttctcgccac gttcgccggc tttccccgtc aagctctaaa tcggggggctc cctttagggt    4500 tccgatttag tgctttacgg cacctcgacc ccaaaaaact tgattagggt gatggttcac    4560
gtagtgggcc atcgccctga tagacggttt ttcgcccttt gacgttggag tccacgttct    4620
ttaatagtgg actcttgttc caaactggaa caacactcaa ccctatctcg gtctattctt    4680
ttgatttata agggattttg ccgatttcgg cctattggtt aaaaaatgag ctgatttaac    4740
aaaaatttaa cgcgaatttt aacaaaatat taacgtttac aatttcctga tgcggtattt    4800
tctccttacg catctgtgcg gtatttcaca ccgcataggg taataactga tataattaaa    4860
```

```
ttgaagctct aatttgtgag tttagtatac atgcatttac ttataataca gttttttagt    4920
tttgctggcc gcatcttctc aaatatgctt cccagcctgc ttttctgtaa cgttcaccct    4980
ctaccttagc atcccttccc tttgcaaata gtcctcttcc aacaataata atgtcagatc    5040
ctgtagagac cacatcatcc acggttctat actgttgacc caatgcgtct cccttgtcat    5100
ctaaacccac accgggtgtc ataatcaacc aatcgtaacc ttcatctctt ccacccatgt    5160
ctctttgagc aataaagccg ataacaaaat ctttgtcgct cttcgcaatg tcaacagtac    5220
ccttagtata ttctccagta gatagggagc ccttgcatga caattctgct aacatcaaaa    5280
ggcctctagg ttcctttgtt acttcttctg ccgcctgctt caaaccgcta acaatacctg    5340
ggcccaccac accgtgtgca ttcgtaatgt ctgcccattc tgctattctg tatacacccg    5400
cagagtactg caatttgact gtattaccaa tgtcagcaaa ttttctgtct tcgaagagta    5460
aaaaattgta cttggcggat aatgccttta gcggcttaac tgtgccctcc atggaaaaat    5520
cagtcaagat atccacatgt gttttttagta aacaattttt gggacctaat gcttcaacta    5580
actccagtaa ttccttggtg gtacgaacat ccaatgaagc acacaagttt gtttgctttt    5640
cgtgcatgat attaaatagc ttggcagcaa caggactagg atgagtagca gcacgttcct    5700
tatatgtagc tttcgacatg atttatcttc gtttcctgca ggttttttgtt ctgtgcagtt    5760
gggttaagaa tactgggcaa tttcatgttt cttcaacact acatatgcgt atatatacca    5820
atctaagtct gtgctccttc cttcgttctt ccttctgttc ggagattacc gaatcaaaaa    5880
aatttcaaag aaaccgaaat caaaaaaaag aataaaaaaa aatgatgaa ttgaattgaa    5940
aagctgtggt atggtgcact ctcagtacaa tctgctctga tgccgcatag ttaagccagc    6000
cccgacaccc gccaacaccc gctgacgcgc cctgacgggc ttgtctgctc ccggcatccg    6060
cttacagaca agctgtgacc gtctccggga gctgcatgtg tcagaggttt tcaccgtcat    6120
caccgaaacg cgcgagacga aagggcctcg tgatacgcct attttatag gttaatgtca    6180
tgataataat ggtttcttag tatgatccaa tatcaaagga aatgatagca ttgaaggatg    6240
agactaatcc aattgaggag tggcagcata tagaacagct aaagggtagt gctgaaggaa    6300
gcatacgata ccccgcatgg aatgggataa tatcacagga ggtactagac tacctttcat    6360
cctacataaa tagacgcata taagtacgca tttaagcata aacacgcact atgccgttct    6420
tctcatgtat atatatatac aggcaacacg cagatatagg tgcgacgtga acagtgagct    6480
gtatgtgcgc agctcgcgtt gcattttcgg aagcgctcgt tttcggaaac gctttgaagt    6540
tcctattccg aagttcctat tctctagaaa gtataggaac ttcagagcgc ttttgaaaac    6600
caaaagcgct ctgaagacgc actttcaaaa aaccaaaaac gcaccggact gtaacgagct    6660
actaaaatat tgcgaatacc gcttccacaa acattgctca aaagtatctc tttgctatat    6720
atctctgtgc tatatcccta tataacctac ccatccacct ttcgctcctt gaacttgcat    6780
ctaaactcga cctctacatt ttttatgttt atctctagta ttactcttta gacaaaaaaa    6840
ttgtagtaag aactattcat agagtgaatc gaaaacaata cgaaaatgta aacatttcct    6900
atacgtagta tatagagaca aaatagaaga aaccgttcat aattttctga ccaatgaaga    6960
atcatcaacg ctatcacttt ctgttcacaa agtatgcgca atccacatcg gtatagaata    7020
taatcgggga tgcctttatc ttgaaaaaat gcacccgcag cttcgctagt aatcagtaaa    7080
cgcgggaagt ggagtcaggc ttttttttatg gaagagaaaa tagacaccaa agtagccttc    7140
ttctaacctt aacggaccta cagtgcaaaa agttatcaag agactgcatt atagagcgca    7200
```

```
caaaggagaa aaaaagtaat ctaagatgct ttgttagaaa aatagcgctc tcgggatgca    7260
tttttgtaga acaaaaaaga agtatagatt ctttgttggt aaaatagcgc tctcgcgttg    7320
catttctgtt ctgtaaaaat gcagctcaga ttctttgttt gaaaaattag cgctctcgcg    7380
ttgcatttt gttttacaaa aatgaagcac agattcttcg ttggtaaaat agcgctttcg    7440
cgttgcattt ctgttctgta aaaatgcagc tcagattctt tgtttgaaaa attagcgctc    7500
tcgcgttgca tttttgttct acaaaatgaa gcacagatgc ttcgttcagg tggcactttt    7560
cgggaaatg tgcgcggaac ccctatttgt ttatttttct aaatacattc aaatatgtat    7620
ccgctcatga caataaacc ctgataaatg cttcaataat attgaaaaag gaagagtatg    7680
agtattcaac atttccgtgt cgcccttatt ccctttttg cggcattttg ccttcctgtt    7740
tttgctcacc cagaaacgct ggtgaaagta aaagatgctg aagatcagtt gggtgcacga    7800
gtgggttaca tcgaactgga tctcaacagc ggtaagatcc ttgagagttt tcgccccgaa    7860
gaacgttttc caatgatgag cacttttaaa gttctgctat gtggcgcggt attatcccgt    7920
attgacgccg ggcaagagca actcggtcgc cgcatacact attctcagaa tgacttggtt    7980
gagtactcac cagtcacaga aaagcatctt acggatggca tgacagtaag agaattatgc    8040
agtgctgcca taaccatgag tgataacact gcggccaact tacttctgac aacgatcgga    8100
ggaccgaagg agctaaccgc ttttttgcac aacatggggg atcatgtaac tcgccttgat    8160
cgttgggaac cggagctgaa tgaagccata ccaaacgacg agcgtgacac cacgatgcct    8220
gtagcaatgg caacaacgtt gcgcaaacta ttaactggcg aactacttac tctagcttcc    8280
cggcaacaat taatagactg gatggaggcg gataaagttg caggaccact tctgcgctcg    8340
gcccttccgg ctggctggtt tattgctgat aaatctggag ccggtgagcg tgggtctcgc    8400
ggtatcattg cagcactggg gccagatggt aagccctccc gtatcgtagt tatctacacg    8460
acggggagtc aggcaactat ggatgaacga aatagacaga tcgctgagat aggtgcctca    8520
ctgattaagc attggtaact gtcagaccaa gtttactcat atatacttta gattgattta    8580
aaacttcatt tttaatttaa aaggatctag gtgaagatcc tttttgataa tctcatgacc    8640
aaaatccctt aacgtgagtt ttcgttccac tgagcgtcag accccgtaga aaagatcaaa    8700
ggatcttctt gagatccttt ttttctgcgc gtaatctgct gcttgcaaac aaaaaaacca    8760
ccgctaccag cggtggtttg tttgccggat caagagctac caactctttt tccgaaggta    8820
actggcttca gcagagcgca gataccaaat actgtccttc tagtgtagcc gtagttaggc    8880
caccacttca agaactctgt agcaccgcct acatacctcg ctctgctaat cctgttacca    8940
gtggctgctg ccagtggcga taagtcgtgt cttaccgggt tggactcaag acgatagtta    9000
ccggataagg cgcagcggtc gggctgaacg ggggggttcgt gcacacagcc cagcttggag    9060
cgaacgacct acaccgaact gagatacccta cagcgtgagc tatgagaaag cgccacgctt    9120
cccgaaggga gaaaggcgga caggtatccg gtaagcggca gggtcggaac aggagagcgc    9180
acgagggagc ttccaggggg aaacgcctgg tatctttata gtcctgtcgg gtttcgccac    9240
ctctgacttg agcgtcgatt tttgtgatgc tcgtcagggg ggcggagcct atggaaaaac    9300
gccagcaacg cggccttttt acggttcctg gccttttgct ggccttttgc tcacatgttc    9360
tttcctgcgt tatcccctga ttctgtggat aaccgtatta ccgcctttga gtgagctgat    9420
accgctcgcc gcagccgaac gaccgagcgc agcgagtcag tgagcgagga agcggaagag    9480
cgcccaatac gcaaaccgcc tctccccgcg cgttggccga ttcattaatg cagctggcac    9540
gacaggtttc ccgactggaa agcgggcagt gagcgcaacg caattaatgt gagttacctc    9600
```

```
actcattagg cacccaggc tttacactt atgcttccgg ctcctatgtt gtgtggaatt   9660
gtgagcggat aacaatttca cacaggaaac agctatgacc atgattacgc caagcgcgca   9720
attaaccctc actaaaggga acaaaagctg gagct                              9755
```

<210> SEQ ID NO 25
<211> LENGTH: 10552
<212> TYPE: DNA
<213> ORGANISM: Artificial Sequence
<220> FEATURE:
<223> OTHER INFORMATION: Synthetic:
      p425-HXT7p-SccytoEtr1-TPI7t-TEF1p-ScErg10-CYC1t

<400> SEQUENCE: 25

```
catagcttca aaatgtttct actccttttt tactcttcca gattttctcg gactccgcgc     60
atcgccgtac cacttcaaaa cacccaagca cagcatacta aatttcccct ctttcttcct    120
ctagggtgtc gttaattacc cgtactaaag gtttggaaaa gaaaaaagag accgcctcgt    180 ttcttttct tcgtcgaaaa aggcaataaa aattttatc acgttctttt tcttgaaaa     240 tttttttt gatttttttc tctttcgatg acctcccatt gatatttaag ttaataaacg     300
gtcttcaatt tctcaagttt cagtttcatt ttcttgttc tattacaact ttttttactt    360
cttgctcatt agaaagaaag catagcaatc taatctaagt ctagaactag tatgtctcag    420
aacgtttaca ttgtatcgac tgccagaacc ccaattggtt cattccaggg ttctctatcc    480
tccaagacag cagtggaatt gggtgctgtt gctttaaaag gcgccttggc taaggttcca    540
gaattggatg catccaagga ttttgacgaa attattttg gtaacgttct ttctgccaat    600
ttgggccaag ctccggccag acaagttgct ttggctgccg gtttgagtaa tcatatcgtt    660
gcaagcacag ttaacaaggt ctgtgcatcc gctatgaagg caatcatttt gggtgctcaa    720
tccatcaaat gtggtaatgc tgatgttgtc gtagctggtg gttgtgaatc tatgactaac    780
gcaccatact acatgccagc agcccgtgcg ggtgccaaat ttggccaaac tgttcttgtt    840
gatggtgtcg aaagagatgg gttgaacgat gcgtacgatg gtctagccat gggtgtacac    900
gcagaaaagt gtgcccgtga ttgggatatt actagagaac aacaagacaa ttttgccatc    960
gaatcctacc aaaaatctca aaatctcaa aaggaaggta aattcgacaa tgaaattgta   1020
cctgttacca ttaagggatt tagaggtaag cctgatactc aagtcacgaa ggacgaggaa   1080
cctgctagat tacacgttga aaaattgaga tctgcaagga ctgtttttcca aaaagaaaac   1140 ggtactgtta ctgccgctaa cgcttctcca atcaacgatg gtgctgcagc cgtcatcttg   1200
gtttccgaaa aagttttgaa ggaaaagaat ttgaagcctt ggctattat caaaggttgg   1260 ggtgaggccg ctcatcaacc agctgatttt acatgggctc catctcttgc agttccaaag   1320
gctttgaaac atgctggcat cgaagacatc aattctgttg attactttga attcaatgaa   1380
gccttttcgg ttgtcggttt ggtgaacact aagattttga agctagaccc atctaaggtt   1440
aatgtatatg gtggtgctgt tgctctaggt cacccattgg gttgttctgg tgctagagtg   1500
gttgttacac tgctatccat cttacagcaa gaaggaggta agatcggtgt tgccgccatt   1560
tgtaatggtg gtggtggtgc ttcctctatt gtcattgaaa agatatgagt cgacctcgag   1620
attagttatg tcacgcttac attcacgccc tccccccaca tccgctctaa ccgaaaagga   1680 aggagtaga caacctgaag tctaggtccc tatttatttt tttatagtta tgttagtatt   1740
aagaacgtta tttatattc aaatttttct tttttctg tacagacgcg tgtacgcatg   1800
taacattata ctgaaaacct tgcttgagaa ggttttggga cgctcgaagg ctttaatttg   1860
```

```
ggtacccaat tcgccctata gtgagtcgta ttacgcgcgc tcactggccg tcgttttaca    1920
acgtcgtgac tgggaaaacc ctggcgttac ccaacttaat cgccttgcag cacatccccc    1980
tttcgccagc tggcgtaata gcgaagaggc ccgcaccgat cgcccttccc aacagttgcg    2040
cagcctgaat ggcgaatggc gcgacgcgcc ctgtagcggc gcattaagcg cggcgggtgt    2100
ggtggttacg cgcagcgtga ccgctacact tgccagcgcc ctagcgcccg ctcctttcgc    2160
tttcttccct tcctttctcg ccacgttcgc cggctttccc cgtcaagctc taaatcgggg    2220
gctcccttta gggttccgat ttagtgcttt acggcacctc gaccccaaaa aacttgatta    2280
gggtgatggt tcacgtagtg ggccatcgcc ctgatagacg ttttttcgcc ctttgacgtt    2340
ggagtccacg ttctttaata gtggactctt gttccaaact ggaacaacac tcaaccctat    2400
ctcggtctat tcttttgatt tataagggat tttgccgatt tcggcctatt ggttaaaaaa    2460
tgagctgatt taacaaaaat ttaacgcgaa ttttaacaaa atattaacgt ttacaatttc    2520
ctgatgcggt attttctcct tacgcatctg tgcggtattt cacaccgcat atcgacggtc    2580
gaggagaact tctagtatat ccacatacct aatattattg ccttattaaa aatggaatcc    2640
caacaattac atcaaaatcc acattctctt caaaatcaat tgtcctgtac ttccttgttc    2700
atgtgtgttc aaaaacgtta tatttatagg ataattatac tctatttctc aacaagtaat    2760
tggttgtttg gccgagcggt ctaaggcgcc tgattcaaga aatatcttga ccgcagttaa    2820
ctgtgggaat actcaggtat cgtaagatgc aagagttcga atctcttagc aaccattatt    2880 ttttcctca acataacgag aacacacagg ggcgctatcg cacagaatca aattcgatga    2940
ctggaaattt tttgttaatt tcagaggtcg cctgacgcat ataccttttt caactgaaaa    3000
attgggagaa aaaggaaagg tgagaggccg gaaccggctt ttcatataga atagagaagc    3060
gttcatgact aaatgcttgc atcacaatac ttgaagttga caatattatt taaggaccta    3120
ttgttttttc caataggtgg ttagcaatcg tcttactttc taacttttct taccttttac    3180
atttcagcaa tatatatata tatttcaagg ataccatt ctaatgtctg cccctatgtc    3240
tgcccctaag aagatcgtcg ttttgccagg tgaccacgtt ggtcaagaaa tcacagccga    3300
agccattaag gttcttaaag ctatttctga tgttcgttcc aatgtcaagt tcgatttcga    3360
aaatcattta attggtggtg ctgctatcga tgctacaggt gtcccacttc cagatgaggc    3420
gctggaagcc tccaagaagg ttgatgccgt tttgttaggt gctgtggctg gtcctaaatg    3480
gggtaccggt agtgttagac ctgaacaagg tttactaaaa atccgtaaag aacttcaatt    3540
gtacgccaac ttaagaccat gtaactttgc atccgactct cttttagact tatctccaat    3600
caagccacaa tttgctaaag gtactgactt cgttgttgtc agagaattag tgggaggtat    3660
ttactttggt aagagaaagg aagacgatgg tgatggtgtc gcttgggata gtgaacaata    3720
caccgttcca gaagtgcaaa gaatcacaag aatggccgct ttcatggccc tacaacatga    3780
gccaccattg cctatttggt ccttggataa agctaatctt ttggcctctt caagattatg    3840
gagaaaaact gtggaggaaa ccatcaagaa cgaattccct acattgaagg ttcaacatca    3900
attgattgat tctgccgcca tgatcctagt taagaaccca acccacctaa atggtattat    3960
aatcaccagc aacatgtttg gtgatatcat ctccgatgaa gcctccgtta tcccaggttc    4020
cttgggtttg ttgccatctg cgtccttggc ctctttgcca gacaagaaca ccgcatttgg    4080
tttgtacgaa ccatgccacg ttctgctccc agatttgcca aagaataagg ttgaccctat    4140
cgccactatc ttgtctgctg caatgatgtt gaaattgtca ttgaacttgc ctgaagaagg    4200
```

```
taaggccatt gaagatgcag ttaaaaaggt tttggatgca ggtatcagaa ctggtgattt      4260
aggtggttcc aacagtacca ccgaagtcgg tgatgctgtc gccgaagaag ttaagaaaat      4320
ccttgcttaa aaagattctc ttttttatg atatttgtac ataaacttta taaatgaaat       4380
tcataataga aacgacacga aattacaaaa tggaatatgt tcatagggta gacgaaacta      4440
tatacgcaat ctacatacat ttatcaagaa ggagaaaaag gaggatagta aaggaataca      4500
ggtaagcaaa ttgatactaa tggctcaacg tgataaggaa aaagaattgc actttaacat      4560
taatattgac aaggaggagg gcaccacaca aaaagttagg tgtaacagaa aatcatgaaa      4620
ctacgattcc taatttgata ttggaggatt ttctctaaaa aaaaaaaaat acaacaaata      4680
aaaaacactc aatgacctga ccatttgatg gagtttaagt caataccttc ttgaagcatt      4740
tcccataatg gtgaaagttc cctcaagaat tttactctgt cagaaacggc cttacgacgt      4800
agtcgatatg gtgcactctc agtacaatct gctctgatgc cgcatagtta agccagcccc      4860
gacacccgcc aacacccgct gacgcgccct gacgggcttg tctgctcccg gcatccgctt      4920
acagacaagc tgtgaccgtc tccgggagct gcatgtgtca gaggttttca ccgtcatcac      4980
cgaaacgcgc gagacgaaag ggcctcgtga tacgcctatt tttataggtt aatgtcatga      5040
taataatggt ttcttagtat gatccaatat caaaggaaat gatagcattg aaggatgaga      5100
ctaatccaat tgaggagtgg cagcatatag aacagctaaa gggtagtgct gaaggaagca      5160
tacgataccc cgcatggaat gggataatat cacaggaggt actagactac ctttcatcct      5220
acataaatag acgcatataa gtacgcattt aagcataaac acgcactatg ccgttcttct      5280
catgtatata tatatacagg caacacgcag atataggtgc gacgtgaaca gtgagctgta      5340
tgtgcgcagc tcgcgttgca ttttcggaag cgctcgtttt cggaaacgct ttgaagttcc      5400
tattccgaag ttcctattct ctagaaagta taggaacttc agagcgcttt tgaaaaccaa      5460
aagcgctctg aagacgcact ttcaaaaaac caaaaacgca ccggactgta acgagctact      5520
aaaatattgc gaataccgct tccacaaaca ttgctcaaaa gtatctcttt gctatatatc      5580
tctgtgctat atccctatat aacctaccca tccaccttc gctccttgaa cttgcatcta      5640
aactcgacct ctacattttt tatgtttatc tctagtatta ctctttagac aaaaaaattg      5700
tagtaagaac tattcataga gtgaatcgaa aacaatacga aaatgtaaac atttcctata      5760
cgtagtatat agagacaaaa tagaagaaac cgttcataat tttctgacca atgaagaatc      5820
atcaacgcta tcactttctg ttcacaaagt atgcgcaatc cacatcggta tagaatataa      5880
tcggggatgc ctttatcttg aaaaaatgca cccgcagctt cgctagtaat cagtaaacgc      5940
gggaagtgga gtcaggcttt ttttatggaa gagaaaatag acaccaaagt agccttcttc      6000
taaccttaac ggacctacag tgcaaaaagt tatcaagaga ctgcattata gagcgcacaa      6060
aggagaaaaa aagtaatcta agatgctttg ttagaaaaat agcgctctcg ggatgcattt      6120
ttgtagaaca aaaagaagt atagattctt tgttggtaaa atagcgctct cgcgttgcat       6180
ttctgttctg taaaaatgca gctcagattc tttgtttgaa aaattagcgc tctcgcgttg      6240 cattttttgtt ttacaaaaat gaagcacaga ttcttcgttg gtaaaatagc gctttcgcgt      6300
tgcatttctg ttctgtaaaa atgcagctca gattctttgt ttgaaaaatt agcgctctcg      6360
cgttgcattt ttgttctaca aaatgaagca cagatgcttc gttcaggtgg cacttttcgg      6420
ggaaatgtgc gcggaacccc tatttgttta ttttttctaaa tacattcaaa tatgtatccg      6480
ctcatgagac aataaccctg ataaatgctt caataatatt gaaaaggaa gagtatgagt      6540 attcaacatt tccgtgtcgc ccttattccc ttttttgcgg cattttgcct tcctgttttt      6600
```

```
gctcacccag aaacgctggt gaaagtaaaa gatgctgaag atcagttggg tgcacgagtg   6660
ggttacatcg aactggatct caacagcggt aagatccttg agagttttcg ccccgaagaa   6720
cgttttccaa tgatgagcac tttttaaagtt ctgctatgtg gcgcggtatt atcccgtatt   6780
gacgccgggc aagagcaact cggtcgccgc atacactatt ctcagaatga cttggttgag   6840
tactcaccag tcacagaaaa gcatcttacg gatggcatga cagtaagaga attatgcagt   6900
gctgccataa ccatgagtga taacactgcg gccaacttac ttctgacaac gatcggagga   6960
ccgaaggagc taaccgcttt tttgcacaac atggggatc atgtaactcg ccttgatcgt   7020
tgggaaccgg agctgaatga agccatacca aacgacgagc gtgacaccac gatgcctgta   7080
gcaatggcaa caacgttgcg caaactatta actggcgaac tacttactct agcttcccgg   7140
caacaattaa tagactggat ggaggcggat aaagttgcag gaccacttct gcgctcggcc   7200
cttccggctg gctggtttat tgctgataaa tctggagccg gtgagcgtgg gtctcgcggt   7260
atcattgcag cactggggcc agatggtaag ccctcccgta tcgtagttat ctacacgacg   7320
gggagtcagg caactatgga tgaacgaaat agacagatcg ctgagatagg tgcctcactg   7380
attaagcatt ggtaactgtc agaccaagtt tactcatata tactttagat tgatttaaaa   7440
cttcattttt aatttaaaag gatctaggtg aagatccttt ttgataatct catgaccaaa   7500
atcccttaac gtgagttttc gttccactga gcgtcagacc ccgtagaaaa gatcaaagga   7560
tcttcttgag atcctttttt tctgcgcgta atctgctgct tgcaaacaaa aaaaccaccg   7620
ctaccagcgg tggtttgttt gccggatcaa gagctaccaa ctcttttcc gaaggtaact   7680 ggcttcagca gagcgcagat accaaatact gtccttctag tgtagccgta gttaggccac   7740
cacttcaaga actctgtagc accgcctaca tacctcgctc tgctaatcct gttaccagtg   7800
gctgctgcca gtggcgataa gtcgtgtctt accgggttgg actcaagacg atagttaccg   7860
gataaggcgc agcggtcggg ctgaacgggg gttcgtgca cacagcccag cttggagcga   7920
acgacctaca ccgaactgag atacctacag cgtgagctat gagaaagcgc cacgcttccc   7980
gaagggagaa aggcggacag gtatccggta agcggcaggg tcggaacagg agagcgcacg   8040
agggagcttc caggggggaaa cgcctggtat ctttatagtc ctgtcgggtt cgccacctc   8100 tgacttgagc gtcgattttt gtgatgctcg tcagggggc ggagcctatg gaaaaacgcc   8160
agcaacgcgg cctttttacg gttcctggcc ttttgctggc cttttgctca catgttcttt   8220
cctgcgttat cccctgattc tgtggataac cgtattaccg cctttgagtg agctgatacc   8280
gctcgccgca gccgaacgac cgagcgcagc gagtcagtga gcgaggaagc ggaagagcgc   8340
ccaatacgca aaccgcctct ccccgcgcgt tggccgattc attaatgcag ctggcacgac   8400
aggtttcccg actggaaagc gggcagtgag cgcaacgcaa ttaatgtgag ttacctcact   8460
cattaggcac cccaggcttt acactttatg cttccggctc ctatgttgtg tggaattgtg   8520
agcggataac aatttcacac aggaaacagc tatgaccatg attacgccaa gcgcgcaatt   8580
aaccctcact aaagggaaca aaagctggag ctcacttctc gtaggaacaa tttcgggccc   8640
ctgcgtgttc ttctgaggtt catctttac atttgcttct gctggataat tttcagaggc   8700
aacaaggaaa aattagatgg caaaagtcg tcttcaagg aaaaatcccc accatctttc   8760
gagatcccct gtaacttatt ggcaactgaa agaatgaaaa ggaggaaaat acaaaatata   8820
ctagaactga aaaaaaaaaa gtataaatag agacgtata tgccaatact tcacaatgtt   8880
cgaatctatt cttcatttgc agctattgta aaataataaa acatcaagaa caaacaagct   8940
```

```
                                                                -continued
caacttgtct tttctaagaa caaagaataa acacaaaaac aaaaagtttt tttaatttta    9000
atcaaaaatc tagaatgtcg tcctcagctc atcagattcc caagcacttc aaatcgctca    9060
tctattcaac tcatgaagtt gaggattgta ccaaggtttt gtcagtgaaa aattatacgc    9120
ctaaacaaga cttatctcaa tcaattgtgt taaaaacttt ggcctttccc ataaaccctt    9180
cggatatcaa tcagttgcaa ggagtatacc cgtctcgtcc agaaaagaca tacgattact    9240
ccacagatga gccagccgct atcgccggta atgagggtgt ctttgaagtt gtttctttac    9300
cttcgggaag ttccaaggga gatttgaaat tgggtgaccg agttatccca ttgcaggcaa    9360
atcaagggac ttggtccaat tatagagttt tctctagtag ttctgattta atcaaggtaa    9420
atgatttgga tctgttttct gcggcaactg tatctgttaa tggttgtacc ggtttccaat    9480
tagtatcaga ctatatcgac tggaacagta acggtaatga atggattatc caaaatgccg    9540
gtacatctag tgtatcaaaa atagttacgc aagtagcaaa agctaaaggg atcaaaacat    9600
taagtgttat acgtgaccgt gataattttg atgaggtagc aaaagttttg gaggataagt    9660
atggtgctac gaaggttatt tccgaatcgc aaaacaacga caagacttt gccaaagaag    9720 tattgtccaa gattttgggt gaaaatgcaa gggtgaggct tgccttgaat tctgttggag    9780
gtaaatccag tgcatcaata gcacgtaagt tggaaaataa tgctttgatg ctcacttatg    9840
gaggaatgtc aaaacaacct gtaactttac caacatctct acacattttc aaaggcttga    9900
catccaaagg gtactgggtg actgaaaaga acaaaaaaaa cccccaaagc aagattgaca    9960
ccatcagtga ttttatcaaa atgtataatt atggtcacat tatttcacca agagatgaaa   10020
ttgaaactct tacctggaat actaacacta ctactgacga acagttacta gaactagtca   10080
aaaaaggtat aactgggaag gggaagaaaa aatggttgt tttagaatgg taagtcgacc   10140
tcgaggatta atataattat ataaaaatat tatcttcttt tctttatatc tagtgttatg   10200
taaaataaat tgatgactac ggaaagcttt tttatattgt ttcttttca ttctgagcca    10260 cttaaatttc gtgaatgttc ttgtaaggga cggtagattt acaagtgata caacaaaaag   10320
caaggcgctt tttctaataa aaagaagaaa agcatttaac aattgaacac ctctatatca   10380
acgaagaata ttactttgtc tctaaatcct tgtaaaatgt gtacgatctc tatatgggtt   10440
actcataagt gtaccgaaga ctgcattgaa agtttatgtt ttttcactgg aggcgtcatt   10500
ttcgcgttga gaagatgttc ttatccaaat ttcaactgtt atataggagc tc           10552
```

YEAST STRAIN WITH GLUCOSE AND XYLOSE CO-UTILIZATION CAPACITY

DESCRIPTION OF GOVERNMENT-SPONSORED RESEARCH AND DEVELOPMENT

This research is sponsored by Ministry of Trade, Industry and Energy, New and Renewable Energy R&D Program (Development of a lipid-producing yeast strain co-converting C6/C5 for lignocellulosic bio-diesel production, Project Serial No.: 1415154268) under the management of Korea Institute of Energy Technology Evaluation and Planning.

CROSS-REFERENCE TO RELATED APPLICATION

This application claims priority to Korean Patent Application No. 10-2018-0136647 filed on Nov. 8, 2018 and Korean Patent Application No. 10-2019-0061921, filed on May 27, 2019, and all the benefits accruing therefrom under 35 U.S.C. .sctn.119, the contents of which in its entirety are herein incorporated by reference.

REFERENCE TO SEQUENCE LISTING SUBMITTED VIA EFS-WEB

This application includes an electronically submitted sequence listing in .txt format. The .txt file contains a sequence listing entitled "5398-0122PUS1_ST25.txt" created on Oct. 22, 2019 and is 100,327 bytes in size. The sequence listing contained in this .txt file is part of the specification and is hereby incorporated by reference herein in its entirety.

BACKGROUND OF THE INVENTION

Field of the Invention

This specification relates to a yeast strain capable of simultaneously converting glucose and xylose and a method for producing a biofuel and biomaterial using the same.

Description of the Related Art

New technology for producing biofuel/materials using lignocellulosic biomass have been developed as a method for producing economical fuels/materials that are sustainable in preparation for the post-fossil fuel era. The lignocellulosic biomass is the most abundant carbon source as it accounts for more than 90% of the total biomass produced on earth, is an eco-friendly renewable source, and includes herbaceous and woody biomass. Lignocellulosic biomass includes wood waste, agricultural and forestry waste, bioenergy crops, etc. Production of biofuels using the lignocellulosic biomass leads a great reduction in carbon consumption compared to the fossil fuels and first-generation biofuels.

Biological production technology of biofuels/materials using microorganism fermentation process is economical and eco-friendly, and thus is advantageous. The bioethanol-producing process using *Saccharomyces cerevisiae*, a yeast strain, is operated all over the world. In order to more increase the economics and sustainability of such bioethanol, a process for producing a fuel/material using inedible biomass such as lignocellulosic biomass has been suggested, but *Saccharomyces cerevisiae* has reduced conversion efficiency as it uses biomass-derived hexose (representatively glucose; 50% of the biomass at maximum) only but not pentose (representatively xylose; 25% of the biomass at maximum). If the problem is overcome, a maximum biomass conversion rate is expected to increase up to 50% to 75%. In this regard, the development of xylose converting-strain is underway.

Such yeast strain does not endogenously possess a xylose metabolic pathway, and thus is incapable of xylose metabolism. There has been a report that a transformed strain in which an oxidoreductase based-xylose metabolic pathway has been developed to provide the yeast with xylose utilization capacity. However, the xylose utilization capacity has not reached a satisfactory level. In particular, the oxidoreductase based-xylose metabolic pathway has a problem in that ethanol production yield is low due to cofactor imbalance. Further, when glucose and xylose, which are main carbon sources derived from lignocellulosic biomass, are simultaneously present, xylose utilization capacity rapidly decreases, and xylose is consumed only after all glucose is consumed, thereby causing a problem of reduced productivity. There is a limitation on an additional modification of xylose-utilizing strains that have so far been developed, thus limiting the product to bioethanol.

CITATION LIST

Patent Literature

Non-Patent Literature 1: Sun-Mi Lee et al., Systematic and evolutionary engineering of xylose isomerase-based pathway in *Saccharomyces cerevisiae* for efficient conversion yields, Biotechnol. Biofuel., 2014 1:122

Non-Patent Literature 2: Verhoeven M D et al., Mutations in PMR1 stimulate xylose isomerase activity and anaerobic growth on xylose of engineered *Saccharomyces cerevisiae* by influencing manganese homeostasis, Sci. Rep. 2017 7:46155

SUMMARY OF THE INVENTION

Technical Problem

In an aspect, the technical problem of the present invention is to provide a transformed yeast strain capable of co-converting glucose/xylose and having enhanced xylose utilization capacity.

In an aspect, the technical problem of the present invention is to provide a method for preparing a transformed yeast strain capable of co-converting glucose/xylose and having enhanced xylose utilization capacity.

In an aspect, the technical problem of the present invention is to provide a method for producing biofuels and biomaterials using a transformed yeast strain capable of co-converting glucose/xylose and having enhanced xylose utilization capacity.

Technical Solution

To solve the problems, an exemplary embodiment of the present invention provides a transformed yeast strain of *Saccharomyces cerevisiae*, comprising at least one of a mutation or deletion of PMR1 represented by the base sequence of SEQ ID NO: 1 and a mutation or deletion of ASC1 represented by the base sequence of SEQ ID NO: 3; and a gene encoding a xylose isomerase; and at least one of a gene encoding a xylulokinase and a gene encoding a transaldolase, wherein the mutation of PMR1 represented by the base sequence of SEQ ID NO: 1 is a mutation to PMR1$^{G681A}$ represented by the base sequence of SEQ ID NO: 2; and the mutation of ASC1 represented by the base sequence of SEQ ID NO: 3 is a mutation to ASC1$^{Q237*}$ represented by the base sequence of SEQ ID NO: 4.

To solve the problems, an exemplary embodiment of the present invention provides a method for preparing the transformed yeast strain, comprising inserting a gene encoding a xylose isomerase; and at least one of a gene encoding a xylulokinase and a gene encoding a transaldolase; and performing at least one of a mutation or deletion of PMR1 represented by the base sequence of SEQ ID NO: 1 and a mutation or deletion of ASC1 represented by the base sequence of SEQ ID NO: 3, while having *Saccharomyces cerevisiae* as a parent strain, wherein the mutation of PMR1 or ASC1 comprises adaptive evolution by subculturing the strain in a minimal medium containing xylose as a sole carbon source.

To solve the problems, an exemplary embodiment of the present invention provides a method for producing a biofuel and biomaterial, comprising fermenting the transformed yeast strain by culturing the transformed yeast strain in a medium containing xylose or glucose as a sole carbon source or a medium containing glucose and xylose as mixed carbon sources.

DETAILED DESCRIPTION OF THE PREFERRED EMBODIMENTS

Figure 1A:
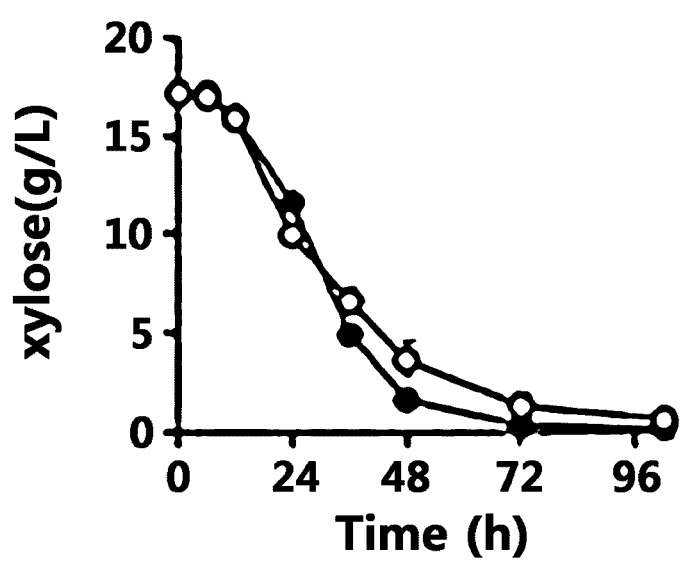
FIG. 1A is a diagram showing curves of xylose utilization of *Saccharomyces cerevisiae* SXA-R2P-E strain (Comparative Example 1), a comparative example of the present invention, and that of the xylose-utilizing strain (XUSE; Example 1), an exemplary embodiment of the present invention, in a medium containing xylose as a sole carbon source.

Hereinafter, the following Examples will be described in detail.

An exemplary embodiment of the present invention provides a transformed yeast strain of *Saccharomyces cerevisiae* capable of co-converting glucose and xylose.

A *Saccharomyces cerevisiae* yeast strain is a representative bioethanol-producing strain, and is used as a platform strain for the production of various biofuels and biomaterials due to its ease of metabolic engineering. However, the wild-type *Saccharomyces cerevisiae* strain is known to be unable to use xylose as a carbon source. Glucose is a carbon source which a yeast strain such as *Saccharomyces cerevisiae* strain can utilize among available carbon sources within lignocellulosic biomass and accounts for about 50% of the total lignocellulosic biomass. When lignocellulosic biomass is used as a raw material which provides a yeast strain a carbon source necessary for the production of biofuels and biomaterials, the yeast strain only uses glucose as the carbon source, causing a problem of a low conversion rate to ethanol.

In this regard, the present inventors have developed as a technology of producing biofuels and biomaterials a yeast strain capable of co-utilizing lignocellulosic biomass-derived mixed sugars (glucose/xylose) by transforming a yeast strain capable of utilizing lignocellulosic biomass-derived glucose only, specifically a *Saccharomyces cerevisiae* strain, to provide with xylose utilization capacity.

As an exemplary embodiment, the *Saccharomyces cerevisiae* yeast strain capable of co-converting glucose and xylose may include at least one of a mutation or deletion of PMR1 represented by the base sequence of SEQ ID NO: 1 and a mutation or deletion of ASC1 represented by the base sequence of SEQ ID NO: 3, a gene encoding a xylose isomerase; and at least one of a gene encoding a xylulokinase and a gene encoding a transaldolase.

A parent strain of the transformed *Saccharomyces cerevisiae* is a wild-type *Saccharomyces cerevisiae* yeast strain incapable of utilizing xylose as a carbon source. The wild-type yeast strain may be one that is commercially available or may be a verified one which is deposited in a deposition institution and can be freely furnished by a catalog, etc., issued by the deposition institution. As an exemplary embodiment, the wild-type *Saccharomyces cerevisiae* yeast strain may be *Saccharomyces cerevisiae* BY4741, but is not limited thereto as long as it is a wild-type *Saccharomyces cerevisiae* yeast strain. The *Saccharomyces cerevisiae* BY4741 is deposited under Accession No. ATCC 201388.

As an exemplary embodiment, the PMR1 is a gene represented by the base sequence of SEQ ID NO: 1, encoding Golgi $Ca^{2+}/Mg^{2+}$ATPase. As an exemplary embodiment, the mutation of PMR1 represented by the base sequence of SEQ ID NO: 1 may be a mutation to PMR1$^{G681A}$ represented by the base sequence of SEQ ID NO: 2. The PMR1$^{G681A}$ is a mutant type of a PMR1 gene, and includes a conversion of glycine (G), the 681st amino acid of the entire gene sequence of the *Saccharomyces cerevisiae* parent strain, to alanine (A).

As an exemplary embodiment, the ASC1 is a gene represented by the base sequence of SEQ ID NO: 3, encoding a guanine dissociation inhibitor of Gpa2p. The mutation of ASC1 represented by the base sequence of SEQ ID NO: 3 may be a mutation to ASC1$^{Q237*}$ represented by the base sequence of SEQ ID NO: 4. The ASC1$^{Q237*}$ is a mutant type of an ASC1 gene, and includes a conversion of glutamine (Q) at position 237 of the entire amino acid sequence of the *Saccharomyces cerevisiae* parent strain with a stop codon.

In an exemplary embodiment, xylose isomerase activity can be enhanced by deleting at least one of the PMR1 and ASC1 or containing at least one mutant gene of the PMR1$^{G681A}$ and ASC1$^{Q237*}$.

As an exemplary embodiment, the gene encoding the xylose isomerase is a gene encoding an enzyme interconverting D-xylose and D-xylulose, but is not limited thereto as long as xylose isomerization is feasible. As an exemplary embodiment, the xylose isomerase-encoding gene may include xylA3* represented by the base sequence of SEQ ID NO: 5, xylA isolated from *Piromyces* sp., which is represented by the base sequence of SEQ ID NO: 6, xylA isolated from *Clostridium phytofermentans*, which is represented by the base sequence of SEQ ID NO: 7 or xylA isolated from *Clostridium thermosulfurgenes*, which is represented by the base sequence of SEQ ID NO: 8. In terms of isomerization efficiency, the gene may preferably include xylA3* represented by the base sequence of SEQ ID NO: 5.

As an exemplary embodiment, the gene encoding xylulokinase is a gene encoding an enzyme producing D-xylulose-5-phosphate from D-xylulose, but is not limited thereto as long as xylose phosphorylation is feasible. As an exemplary embodiment, the xylulokinase-encoding gene may include XKS1 represented by the base sequence of SEQ ID NO: 9 or xyl3 isolated from *Scheffersomyces stipites*, which is represented by the base sequence of SEQ ID NO: 10.

As an exemplary embodiment, the transaldolase-encoding gene is not limited as long as it is an enzyme which catalyzes conversions of sedoheptulose-7-phosphate and glyceraldehyde-3-phosphate to fructose-6-phosphate and erythrose-4-phosphate. As an exemplary embodiment, the transaldolase may include TAL1 represented by the base sequence of SEQ ID NO: 11 or tal1 isolated from *Scheffersomyces stipites*, which is represented by the base sequence of SEQ ID NO: 12.

As an exemplary embodiment, the *Saccharomyces cerevisiae* transformed yeast strain may include at least one deletion of an aldose reductase-encoding gene and a phosphatase-encoding gene.

As an exemplary embodiment, the aldose reductase-encoding gene may include GRE3 represented by the base sequence of SEQ ID NO: 13. As an exemplary embodiment, the phosphatase-encoding gene may include PHO13 represented by the base sequence of SEQ ID NO: 14.

As an exemplary embodiment, the transformed yeast strain may be a transformed yeast strain in which PMR1 represented by the base sequence of SEQ ID NO: 1 and ASC1 represented by the base sequence of SEQ ID NO: 3 are deleted, genes encoding xylose isomerase, xylulokinase and transaldolase are included, and genes encoding aldose reductase and phosphatase are deleted.

In another exemplary embodiment, the transformed yeast strain may be a transformed yeast strain in which PMR1$^{G681A}$ represented by the base sequence of SEQ ID NO: 2 and ASC1$^{Q237*}$ represented by the base sequence of SEQ ID NO: 4 are included, genes encoding xylose isomerase, xylulokinase and transaldolase are included, and genes encoding aldose reductase and phosphatase are deleted.

As an exemplary embodiment, the *Saccharomyces cerevisiae* transformed yeast strain is deposited under Accession No. KCTC13614BP.

In this specification, the mutant can be introduced by treating a microorganism with any chemical and/or physical means known in the technical field of the present invention to cause a mutation. The chemical means may be nitrosoguanidine (NTG), which is a guanidine derivative, methyl methanesulfonate (MMS), ethyl methanesulfonate (EMS), benzopyrene, and other chemicals useful as a mutation inducer (mutagen), and the physical means may be radiation such as X-ray and γ-ray, but is not limited thereto. In addition, the mutant gene can be introduced using a molecular biological method, specifically genetic scissors such as CRISPR-Cas9, but is not limited thereto.

As an exemplary embodiment, the *Saccharomyces cerevisiae* transformed yeast strain may have an improved xylose fermentation rate compared to *Saccharomyces cerevisiae*, which is a parent strain, since a xylose isomerase-based xylose metabolic pathway is introduced by the transformation as the above. Specifically, the rate may be improved by at least 30% or 50%, and more specifically by 30% to 150%.

Further, as an exemplary embodiment, the *Saccharomyces cerevisiae* transformed yeast strain can simultaneously ferment glucose and xylose to convert to ethanol, and thus may have an increased conversion rate of glucose and xylose to ethanol compared to the parent strain *Saccharomyces cerevisiae*. Specifically, the rate may be increased by at least 50% or 100%, and more specifically by 50% to 300%.

As xylose and glucose account for up to about 30% and about 50%, respectively, within lignocellulosic biomass, the transformed yeast strain according to the exemplary embodiments of the present invention can utilize resources available within the lignocellulosic biomass up to about 80% by simultaneously converting glucose and xylose. Accordingly, the economics and sustainability of the biofuel and biomaterial production using lignocellulosic biomass can be greatly enhanced by greatly improving ethanol production yield over unit biomass.

Additionally, the *Saccharomyces cerevisiae* transformed yeast strain according to the present invention can produce not only bioethanol but also other biofuels or biomaterials such as butanol without an additional process through an additional modification of the stain itself. The additional modification may include introducing a combination of genes constituting a synthetic pathway of a product in a strain and expressing the same. For example, the *Saccharomyces cerevisiae* transformed yeast strain can be modified so as to produce butanol by further including genes constituting a butanol biosynthetic pathway. As an exemplary embodiment, the butanol biosynthetic pathway-constituting genes may include β-hydroxybutyryl-CoA dehydrogenase (Hbd; SEQ ID NO: 17), 3-hydroxybutyryl-CoA dehydratase (Crt; SEQ ID NO: 18) and butanol dehydrogenase (BdhB; SEQ ID NO: 19), which are derived from *Clostridium acetobutyricum*, acetoacetyl-CoA thiolase (Erg10; SEQ ID NO: 20) and enoyl thioester reductase (Etr1; SEQ ID NO: 21), which are derived from *Saccharomyces cerevisiae*, and butyraldehyde dehydrogenase (EutE; SEQ ID NO: 22) which is derived from *Escherichia coli*. As an exemplary embodiment, the *Saccharomyces cerevisiae* transformed yeast strain may have the butanol biosynthetic pathway-constituting genes introduced in the form of a plasmid. As an exemplary embodiment, the *Saccharomyces cerevisiae* transformed yeast strain may include the butanol biosynthetic pathway-constituting genes introduced in the form of being introduced in a genomic DNA. Specifically, the additionally modified *Saccharomyces cerevisiae* transformed yeast strain may be one in which p423-GPDp-CaHbd-PRM9t-TEF1p-CaCrt-CPS1t, which is a plasmid represented by the base sequence of SEQ ID NO: 23, p426-PGKp-EcEute-CYC1t-CYC1p-CaBdhb-SPG5t, which is a plasmid represented by the base sequence of SEQ ID NO: 24 and p425-HXT7p-SccytoEtr1-TPI1t-TEF1p-ScErg10-CYC1t, which is a plasmid represented by the base sequence of SEQ ID NO: 25 are introduced. Such modified *Saccharomyces cerevisiae* transformed yeast strain can produce butanol in addition to ethanol by co-fermenting glucose and xylose.

As an exemplary embodiment, the present invention may include a culture of the *Saccharomyces cerevisiae* transformed yeast strain previously described. The culture may include ethanol, and may also include other biofuels such as butanol through an additional modification.

As used herein, the term "culture" may unlimitedly include any culture method known in the art. As an exemplary embodiment, the culture of the yeast strain may be any one selected from the group consisting of shaken culture, stationary culture, batch culture, fed-batch culture, and continuous culture. The "shaken culture" refers to a method of culturing a culture inoculated with a microorganism by shaking, and the "stationary culture" refers to a method of culturing a liquid culture inoculated with a microorganism in a stationary state without shaking. The "batch culture" refers to a method of culturing in a fixed volume of a culture medium without adding a fresh culture, and an apparatus for such culture method is called a "batch reactor". The "fed-batch culture", contrary to simple batch culture involving putting an entire amount of a raw material to a culture tank at the beginning of the culturing, refers to a culture method involving supplying a small amount of an element to a culture tank and then adding small amounts of raw materials, and an apparatus for such culture method is called a "fed-batch reactor". The "continuous culture" refers to a culture method involving continuous supply of fresh nutrient media while removing a culture containing cells and products, and an apparatus for such culture method is called "continuous culture reactor". Specifically, the culture may be practiced in the batch reactor, continuous reactor or fed-batch reactor.

As an exemplary embodiment, the culture may be practiced in a conventional culture medium containing at least one selected from the group consisting of an appropriate carbon source, a nitrogen source, an amino acid, a vitamin, etc. while adjusting temperature, pH, etc., thereby fulfilling culture requirements of a yeast strain in a suitable manner. For example, carbon sources that can be utilized may include sugars and carbohydrates such as glucose, xylose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; organic acids such as acetic acid; volatile fatty acid (VFA) such as acetic acid, butyric acid, isobutyric acid, propionic acid, valeric acid, isovaleric acid, and caproic acid; etc. These carbon sources can be included individually or in combinations. Nitrogen sources that can be utilized may include inorganic nitrogen sources such as ammonia, ammonium sulfate, ammonium chloride, ammonium acetate, ammonium phosphate, ammonium carbonate, and ammonium nitrate; amino acids such as glutamate, methionine, and glutamine; organic nitrogen sources such as peptone, NZ-amine, meat extract, yeast extract, malt extract, corn steep liquor, casein hydrolysates, fish or decomposition products thereof, defatted soybean cake or decomposition products thereof, etc. These nitrogen sources may be used individually or in combination. The medium may include potassium phosphate, dipotassium hydrogen phosphate or corresponding sodium-containing salts as phosphorus sources. Phosphorus sources that may be utilized may include potassium dihydrogen phosphate, dipotassium hydrogen phosphate or corresponding sodium-containing salts. Further, sodium chloride, calcium chloride, iron chloride, magnesium sulfate, iron sulfate, manganese sulfate, calcium carbonate, etc. may be used as an inorganic compound. In addition to the above substances, other substances such as amino acids and vitamins can be utilized.

As an exemplary embodiment, appropriate precursors may be used in a culture medium. The previously described raw materials can be added to the culture in a batch, fed-batch or continuous mode by an appropriate method during the culturing process, but are not limited thereto. A pH of the culture may be adjusted by using an appropriate amount of a basic compound such as sodium hydroxide, potassium hydroxide, and ammonia, or an acidic compound such as phosphoric acid and sulfuric acid by an appropriate method.

An exemplary embodiment according to the present invention can provide a method for preparing the *Saccharomyces cerevisiae* transformed yeast strain.

As an exemplary embodiment, the preparation method may comprise inserting into the strain a gene encoding a xylose isomerase; and at least one of a gene encoding a xylulokinase and a gene encoding a transaldolase; and performing at least one of a mutation or deletion of PMR1 represented by the base sequence of SEQ ID NO: 1 and a mutation or deletion of ASC1 represented by the base sequence of SEQ ID NO: 3, while having *Saccharomyces cerevisiae* as a parent strain. As an exemplary embodiment, the method can comprise deleting at least one of an aldose reductase-encoding gene and a phosphatase-encoding gene.

As an exemplary embodiment, the order of the genes which are inserted or deleted can be any order and is not limited to the order described herein.

Further, as an exemplary embodiment, the preparation method may include performing at least one of a mutation or deletion of PMR1 represented by the base sequence of SEQ ID NO: 1 and a mutation or deletion of ASC1 represented by the base sequence of SEQ ID NO: 3 after inserting a gene encoding a xylose isomerase; and at least one of a gene encoding a xylulokinase and a gene encoding a transaldolase, and/or deleting at least one of an aldose reductase-encoding gene and a phosphatase-encoding gene.

As another exemplary embodiment, the preparation method can include inserting a gene encoding a xylose isomerase; and inserting at least one of a gene encoding a xylulokinase and a gene encoding a transaldolase, and/or deleting at least one of an aldose reductase-encoding gene and a phosphatase-encoding gene, after performing at least one of a mutation or deletion of PMR1 represented by the base sequence of SEQ ID NO: 1 and a mutation or deletion of ASC1 represented by the base sequence of SEQ ID NO: 3.

As an exemplary embodiment, the mutation of PMR1 or ASC1 comprises adaptive evolution by subculturing the strain in a minimal medium including xylose as a sole carbon source, but is not limited thereto and can be included within the scope of the present invention as long as the PMR1 and ASC1 can be mutated to PMR1$^{G681A}$ and ASC1$^{Q237*}$, respectively.

As an exemplary embodiment, the adaptive evolution is a method allowing an evolution occurring in nature to rapidly and effectively occur in vitro so as to obtain an excellent strain. The method can include subculturing the strain in a medium including xylose as a carbon source and then screening a strain with high xylose utilization capacity to select a strain having enhanced xylose utilization capacity. As an exemplary embodiment, the mutation of at least one gene of the PMR1 and ASC1 can include subculturing by culturing the strain in a xylose medium and inoculating and culturing a particular concentration, e.g., about 0.5% (v/v), of the strain in an exponential growth phase in a fresh xylose medium, followed by inoculating a particular concentration, e.g., about 0.5% (v/v), of the strain again in a fresh medium when the strain reaches its exponential phase. Specifically, the minimal medium contains xylose as a carbon source, and may be a medium further including nutrients necessary for the strain growth. For example, the minimal medium is a Yeast Synthetic Complete medium (YSC medium).

A transformed yeast strain having improved xylose utilization capacity can be prepared by introducing a xylose isomerase-based xylose metabolic pathway in a yeast strain adaptively evolved through metabolic engineering and evolutionary engineering. As an exemplary embodiment, the adaptive evolution can include an adaptive evolution allowing to have xylose utilization capacity by subculturing the strain in a medium containing xylose as a sole carbon source two, three, four, five times or more, but is not limited thereto.

As an exemplary embodiment, the insertion or deletion of gene may be carried out using CRISPR/Cas9, but is not limited thereto as long as the gene can be inserted or deleted. As an exemplary embodiment, when the CRISPR/Cas9 is used to transform a strain, an additional modification of a transformed yeast strain, such as an introduction of a synthetic pathway of a fuel/material other than bioethanol, is easily employed.

For example, the preparation method can further include introducing genes constituting a biosynthetic pathway of butanol as another biofuel in the *Saccharomyces cerevisiae* transformed yeast strain. As an exemplary embodiment, the genes constituting the butanol biosynthetic pathway can include β-hydroxybutyryl-CoA dehydrogenase (Hbd; SEQ ID NO: 17), 3-hydroxybutyryl-CoA dehydratase (Crt; SEQ ID NO: 18) and butanol dehydrogenase (BdhB; SEQ ID NO: 19), which are derived from *Clostridium acetobutyricum*, acetoacetyl-CoA thiolase (Erg10; SEQ ID NO: 20) and enoyl thioester reductase (Etr1; SEQ ID NO: 21), which are derived from *Saccharomyces cerevisiae*, and butyraldehyde dehydrogenase (EutE; SEQ ID NO: 22) which is derived from *Escherichia coli*. As an exemplary embodiment, the method can include an introduction of the butanol biosynthetic pathway-constituting genes in the form of a plasmid. As a more specific exemplary embodiment, the preparation method may include introducing p423-GPDp-CaHbd-PRM9t-TEF1-CaCrt-CPS1t, which is a plasmid represented by the base sequence of SEQ ID NO: 23, p426-PGKp-EcEute-CYC1t-CYC1p-CaBdhb-SPG5t, which is a plasmid represented by the base sequence of SEQ ID NO: 24 and p425-HXT7p-SccytoEtr1-TPI7t-TEF1p-ScErg10-CYC1t, which is a plasmid represented by the base sequence of SEQ ID NO: 25 in the *Saccharomyces cerevisiae* transformed yeast strain. As an exemplary embodiment, the further step may involve introducing the plasmid into the strain by transformation, but is not limited thereto as long as the plasmid form can be introduced. As another exemplary embodiment, the genes constituting the butanol biosynthetic pathway can be introduced in the *Saccharomyces cerevisiae* transformed yeast strain in the form of being inserted into a genomic DNA. This gene insertion can be performed using CRISPR/Cas9, but is not limited thereto as long as the gene can be inserted.

An exemplary embodiment according to the present invention can provide a method for producing a biofuel and biomaterial, comprising fermenting the *Saccharomyces cerevisiae* transformed yeast strain by the transformed yeast strain in a medium containing xylose as a sole carbon source. Specifically, the culturing may include inoculating the *Saccharomyces cerevisiae* transformed yeast strain in a minimal medium (YSC medium) containing xylose as a sole carbon source and culturing the same at 28° C. to 32° C. for 24 hours to 168 hours.

Another exemplary embodiment can provide a method for producing a biofuel and biomaterial, comprising fermenting the *Saccharomyces cerevisiae* transformed yeast strain by the transformed yeast strain in a medium containing glucose and xylose as carbon sources. Specifically, the culturing may include inoculating the *Saccharomyces cerevisiae* transformed yeast strain in a minimal medium (YSC medium) containing xylose and glucose as carbon sources and culturing the same at 28° C. to 32° C. for 24 hours to 168 hours.

As an exemplary embodiment, the medium may include lignocellulosic biomass, and the ethanol production method may further include producing at least one of glucose and xylose by disintegrating the lignocellulosic biomass before culturing the yeast strain in the medium. The production of at least one of glucose and xylose by disintegrating the lignocellulosic biomass can include, for example, strong acid-saccharification, weak acid-saccharification, organic solvent pre-treatment, etc., but is not limited thereto as long as at least one of glucose and xylose can be produced from lignocellulosic biomass.

As an exemplary embodiment, the method may further include producing a biofuel and biomaterial using a culture or fermented product of the strain. The term "fermented product", in a broadest sense, refers to not only materials obtained by culturing, i.e., fermenting, the transformed yeast strain according to an exemplary embodiment of the present invention, but also those obtained by culturing a genetically recombinant microorganism having the transformed yeast strain as a parent strain. Examples of the fermented products that are produced can include raw materials capable of producing biofuels and biomaterials. As an exemplary embodiment, the culture or fermented product of the strain may include ethanol and butanol, but is not limited thereto.

The "biofuel" refers to a fuel obtained when biomass is a raw material, and can include ethanol obtained by a method according to an exemplary embodiment of the present invention, but is not limited thereto. As another exemplary embodiment, the method may further produce at least one biofuel or biomaterial selected from butanol, fatty acid ethyl ester, isoprenoid compounds, etc. through an introduction of an additional metabolic pathway in the transformed yeast strain.

Hereinafter, the present invention will be described in more detail with reference to the Examples and accompanying drawings. However, these Examples and accompanying drawings are for illustrative purposes only, and the scope of the present invention is not limited by these Examples and accompanying drawings.

EXAMPLE

Preparation of Transformed Yeast Strain

As an exemplary embodiment of the present invention, the *Saccharomyces cerevisiae* transformed yeast strain having xylose utilization capacity was prepared using the following method:

First, CRISPR/Cas9 system was used to insert xylA3*, which is a xylose isomerase-encoding gene represented by the base sequence of SEQ ID NO: 5, and XKS1, which is a xylulokinase-encoding gene represented by the base sequence of SEQ ID NO: 9, into *Saccharomyces cerevisiae* BY4741 (Accession No.: ATCC 201388), a wild-type *Saccharomyces cerevisiae* yeast strain and also to delete GRE3, an aldose reductase-encoding gene represented by the base sequence of SEQ ID NO: 13. The strain was further modified by inserting xylA3*, which is a xylose isomerase-encoding gene, and TAL1, which is a transaldolase-encoding gene represented by the base sequence of SEQ ID NO: 11, while deleting PHO13, which is a phosphatase-encoding gene represented by the base sequence of SEQ ID NO: 14.

In order to enhance the xylose utilization capacity, the transformed strain was subcultured for adaptive evolution; the strain was cultured in a minimal medium (YSC medium) containing xylose as a sole carbon source, and about 0.5% (v/v) of the strain in exponential phase was inoculated in a fresh xylose medium followed by inoculating about 0.5% (v/v) of the strain again in another fresh medium when the strain reached its exponential phase. As a result, PMR1 represented by the base sequence of SEQ ID NO: 1 and ASC1 represented by the base sequence of SEQ ID NO: 4 were mutated to PMR1$^{G681A}$ represented by the base sequence of SEQ ID NO: 2 and ASC1$^{Q237*}$ represented by the base sequence of SEQ ID NO: 4, respectively.

The strain was named XUSE and was deposited under Accession No. KCTC13614BP.

Test Example 1

To evaluate the xylose utilization capacity of the XUSE strain prepared in the above example (Example 1), the strain was cultured by inoculating in a minimal medium (YSC medium) containing xylose as a sole carbon source and stirring at 200 rpm at 30° C. and observed with respect to the xylose utilization, ethanol production and strain growth.

SXA-R2P-E, an existing xylose-utilizing strain, disclosed in Sun-Mi Lee et al., Systematic and evolutionary engineering of xylose isomerase-based pathway in *Saccharomyces cerevisiae* for efficient conversion yields, Biotechnol. Biofuel., 2014 1:122, incorporated herein in its entirety by reference, was cultured under the same conditions as the XUSE strain to compare the xylose utilization capacity (Comparative Example 1).

Figure 1B:
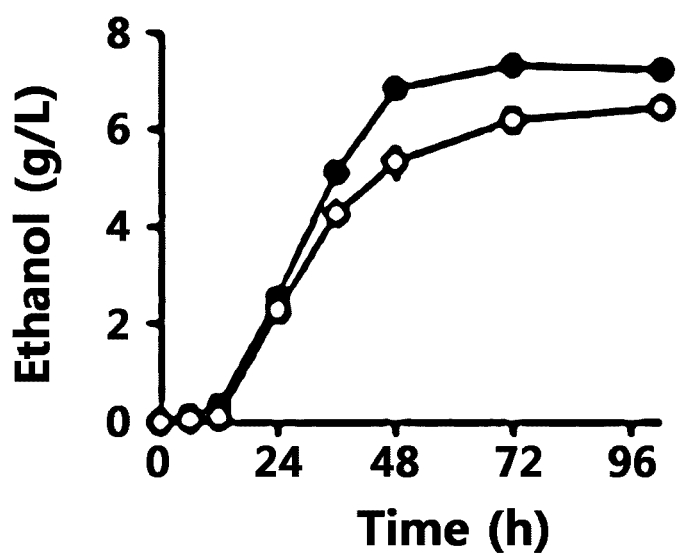
FIG. 1B is a diagram showing curves of ethanol production of *Saccharomyces cerevisiae* SXA-R2P-E strain (Comparative Example 1), a comparative example of the present invention, and that of the xylose-utilizing strain (XUSE; Example 1), an exemplary embodiment of the present invention, in a medium containing xylose as a sole carbon source.
Figure 1C:
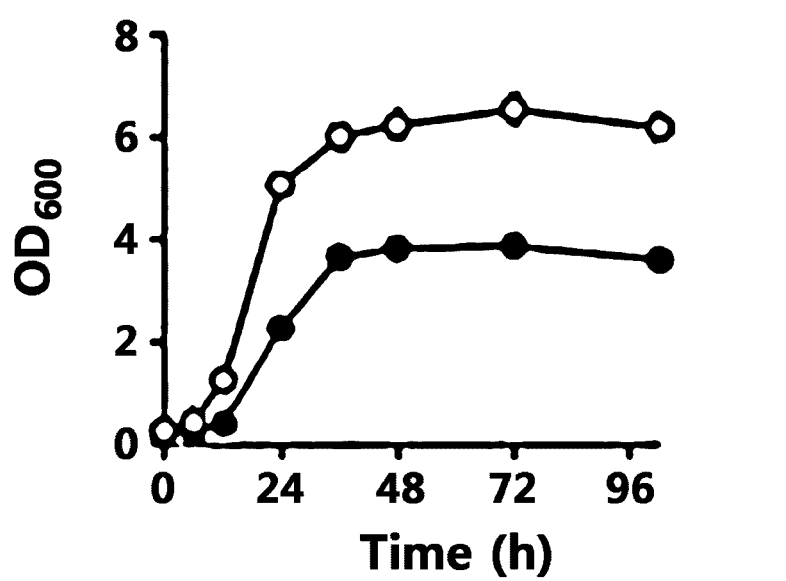
FIG. 1C is a diagram showing curves of strain growth of *Saccharomyces cerevisiae* SXA-R2P-E strain (Comparative Example 1), a comparative example of the present invention, and that of the xylose-utilizing strain (XUSE; Example 1), an exemplary embodiment of the present invention, in a medium containing xylose as a sole carbon source.
Figure 2A:
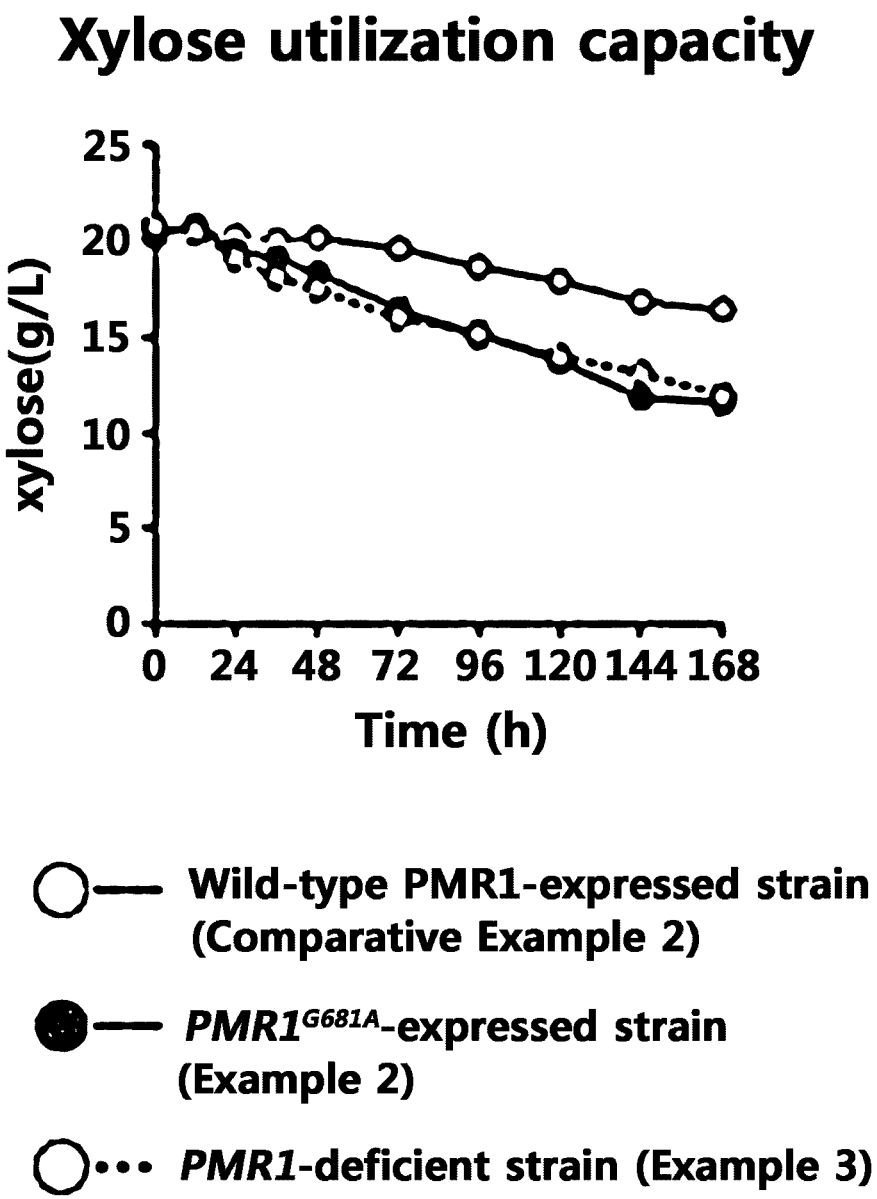
FIG. 2A is a diagram showing curves of xylose utilization of the transformed strain according to PMR1 mutation (Example 2) and PMR1-deleted strain (Example 3), which are exemplary embodiments of the present invention, and wild-type PMR1-expressing strain (Comparative Example 2), which is a comparative example of the present invention, when they were cultured in a medium containing xylose as a sole carbon source.
Figure 2B:
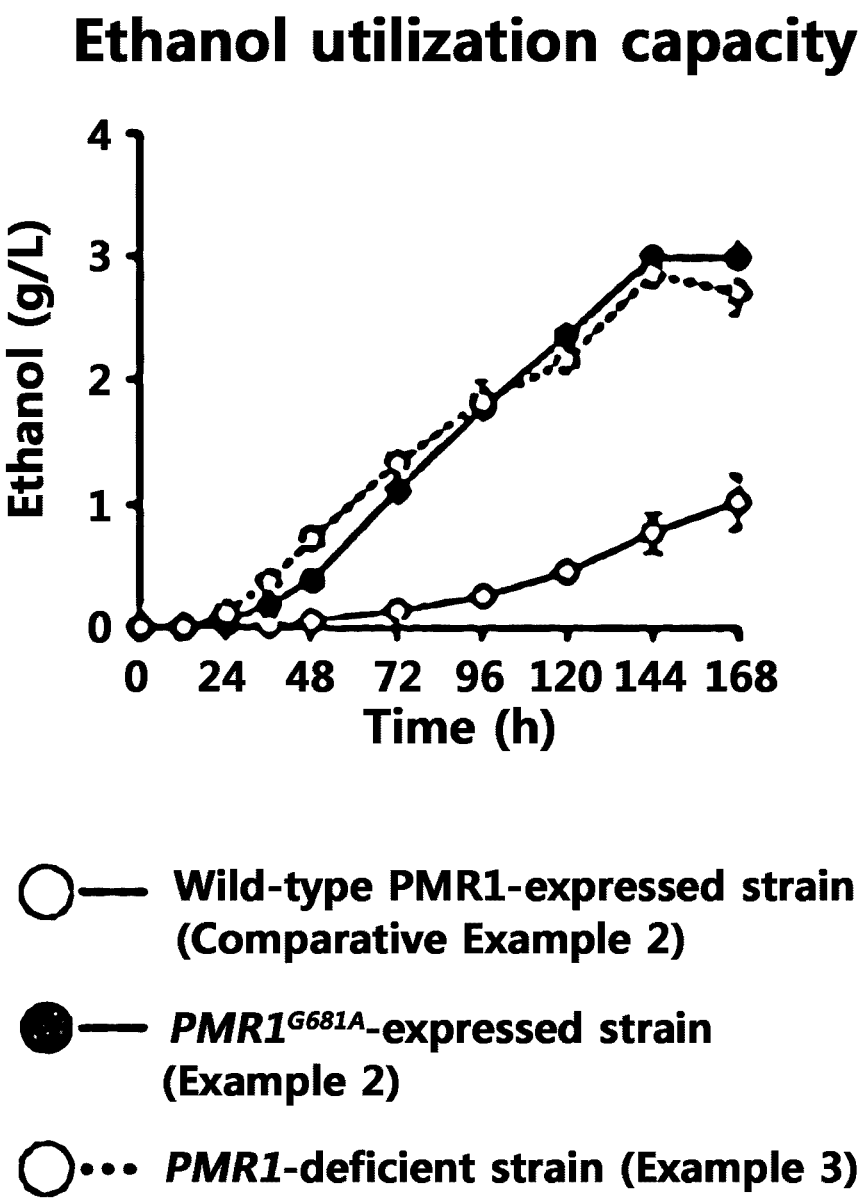
FIG. 2B is a diagram showing curves of ethanol production of the transformed strain according to PMR1 mutation (Example 2) and PMR1-deleted strain (Example 3), which are exemplary embodiments of the present invention, and wild-type PMR1-expressing strain (Comparative Example 2), which is a comparative example of the present invention, when they were cultured in a medium containing xylose as a sole carbon source.
Figure 3A:
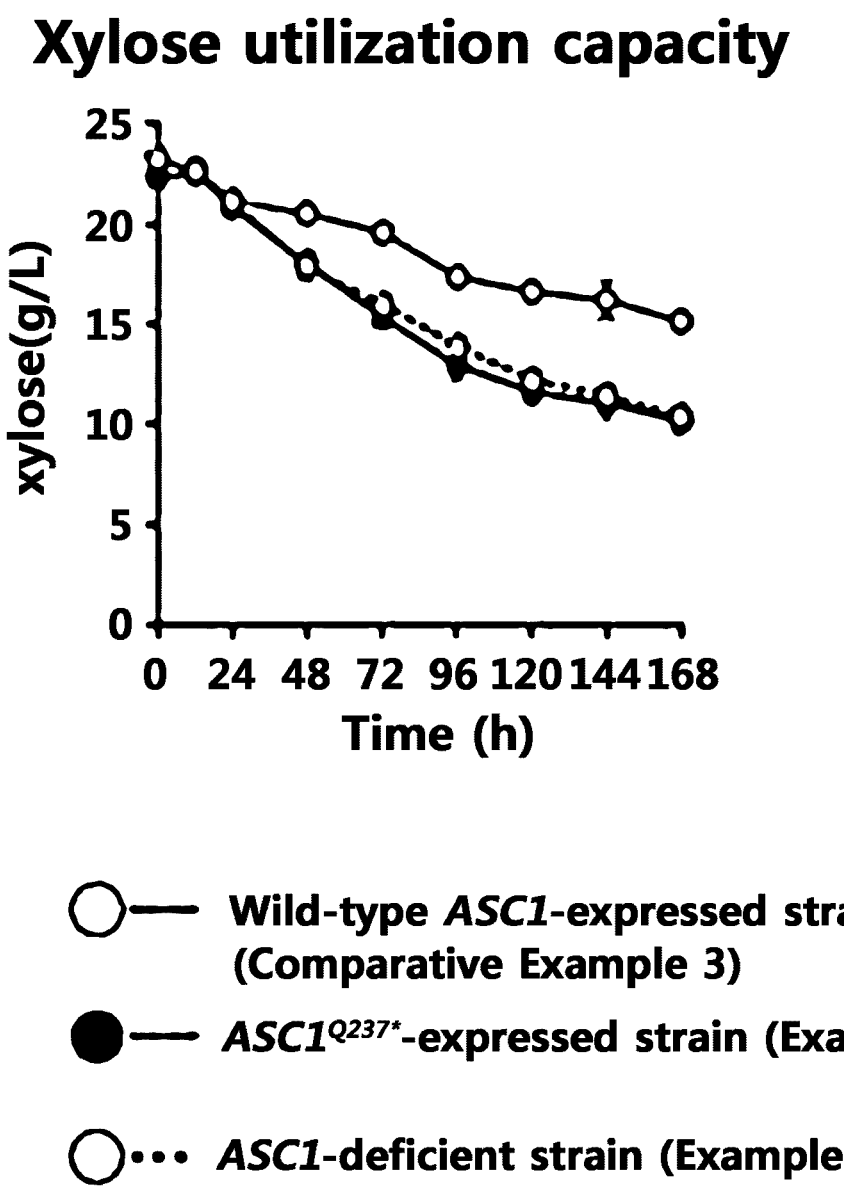
FIG. 3A is a diagram showing curves of xylose utilization of the transformed strain according to ASC1 mutation (Example 4) and ASC1-deleted strain (Example 5), which are exemplary embodiments of the present invention, and wild-type ASC1-expressing strain (Comparative Example 3), which is a comparative example of the present invention, when they were cultured in a medium containing xylose as a sole carbon source.
Figure 3B:
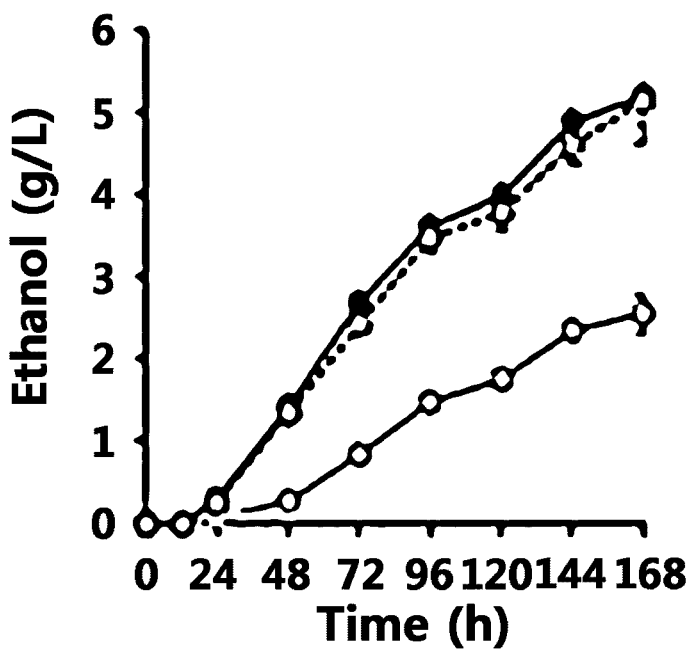
FIG. 3B is a diagram showing curves of ethanol production of the transformed strain according to ASC1 mutation (Example 4) and ASC1-deleted strain (Example 5), which are exemplary embodiments of the present invention, and wild-type ASC1-expressing strain (Comparative Example 3), which is a comparative example of the present invention, when they were cultured in a medium containing xylose as a sole carbon source.

As a result, as shown in FIGS. 1A to 1C, the XUSE strain, an exemplary embodiment of the present invention (Example 1), consumed all 20 g/L xylose in 72 hours and produced ethanol at a yield of 0.43 g ethanol/g xylose. It produced a larger amount of ethanol with lower strain growth (0.43 vs. 0.4) while consuming the same amount of xylose with the SXA-R2P-E strain, a comparative example (Comparative Example 1). The SXA-R2P-E strain is known to have highest yield of ethanol converted from xylose among existing transformed yeast strains, and this indicates that the transformed yeast strain according to the present invention is a strain converting xylose in higher yield, capable of producing high yield of ethanol from xylose. In addition, while it is not easy to additionally modify the SXA-R2P-E strain, the comparative example, thereby limiting a product thereof to ethanol, it is easy to perform additional engineering on the transformed yeast strain according to the present invention using CRISPR-Cas9, which leads to diversification of products. This brings an advantage that the strain can be applied to development of a strain producing fuels and materials in addition to ethanol.

Test Example 2

PMR1 and ASC1 genes were confirmed to be mutated to PMR1$^{G681A}$ and ASC1$^{Q237*}$, respectively, by performing whole genome sequencing on the transformed yeast strain according to an exemplary embodiment of the present invention. The following experiment was carried out to verify that the increased xylose utilization is due to the mutation.

A transformed yeast strain was prepared from the wild-type *Saccharomyces cerevisiae* strain using the same method used for the XUSE strain of the above example (Example 1), except the following difference with respect to gene constitution:

A vector in which a wild-type gene is expressed (Comparative Example 2), a vector represented by the base sequence of SEQ ID NO: 15, which expresses PMR1$^{G681A}$, the mutated gene according to the present invention (Example 2), and a vector in which PMR1 is deleted, that is, an empty vector (Example 3), were introduced in a *Saccharomyces cerevisiae* strain in which PMR1 is deleted.

A vector in which a wild-type gene is expressed (Comparative Example 3), a vector represented by the base sequence of SEQ ID NO: 16, which expresses ASC1$^{Q237*}$, the mutated gene according to the present invention (Example 4), and a vector in which ASC1 is deleted, that is, an empty vector (Example 5), were introduced in a *Saccharomyces cerevisiae* strain in which ASC1 is deleted.

Each of the strains with the respective vectors was inoculated and cultured in a minimal medium (YSC medium) containing xylose as a sole carbon source and stirred at 200 rpm at 30° C. to confirm the xylose utilization capacity and ethanol productivity.

As a result, it was shown in FIGS. 2A, 2B, 3A and 3B that the *Saccharomyces cerevisiae* of Examples 2 to 5 in which PMR1 or ASC1 is deleted, or in which PMR1$^{G681A}$ or ASC1$^{Q237*}$ is expressed showed a great increase in the xylose utilization and ethanol productivity.

In the case of PMR1$^{G681}$-expressing strain (Example 2), the xylose utilization and ethanol production were increased to 115% and 196%, respectively, compared to the strain in which the wild-type PMR1 is expressed (Comparative Example 2). In the case of ASC1$^{Q237*}$-expressing strain (Example 4), the xylose utilization and ethanol production were increased to 60% and 104%, respectively, compared to the strain in which the wild-type ASC1 is expressed (Comparative Example 3). A result of the PMR1 or ASC1 deletion was similar to that of gene mutation, which is due to the fact that a 237th amino acid of ASC1 was substituted with a stop codon and thus lost its function.

This indicates that the deletion or mutation of the PMR1 or ASC1 according to an exemplary embodiment of the present invention plays an important role in the increase in the xylose utilization efficiency.

Text Example 3

In order to confirm the conversion capacity of the transformed yeast strain of an exemplary embodiment of the present invention to the mixed sugars of glucose/xylose, the XUSE strain prepared in Example 1 was cultured by inoculating in a minimal medium (YSC medium) containing xylose and glucose as mixed sugars and stirring at 30° C. at 200 rpm and observed with respect to the xylose/glucose utilization and ethanol production.

Figure 4A:
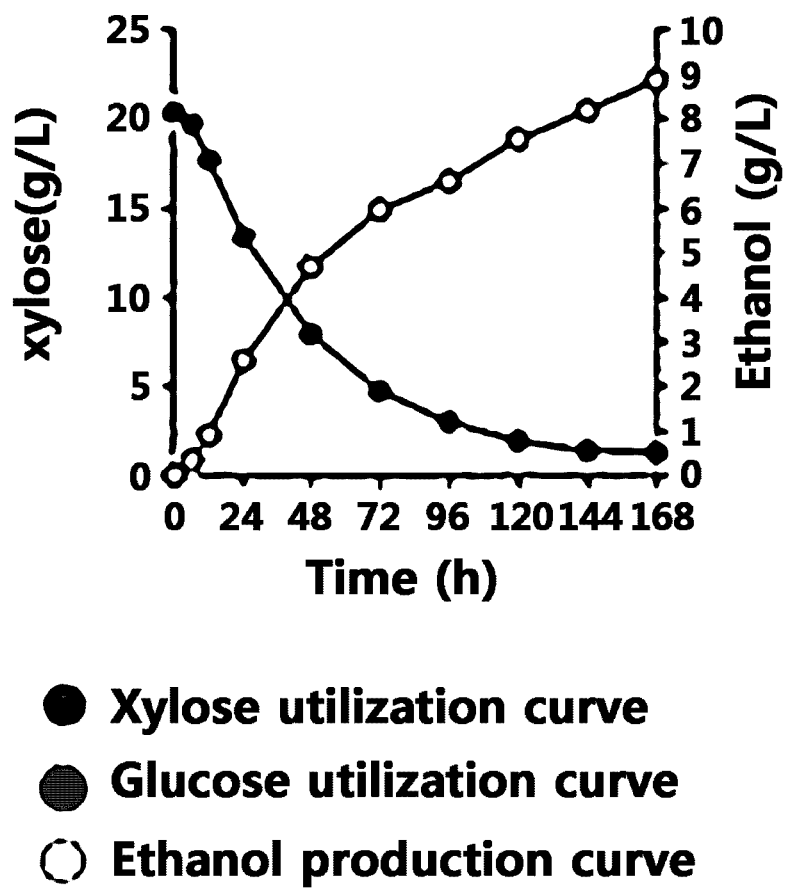
FIG. 4A is a diagram showing glucose utilization curves representing mixed sugar (glucose/xylose) utilization capacity when the transformed strain (XUSE; Example 1) according to an exemplary embodiment of the present invention was cultured in the presence of xylose only.
Figure 4B:
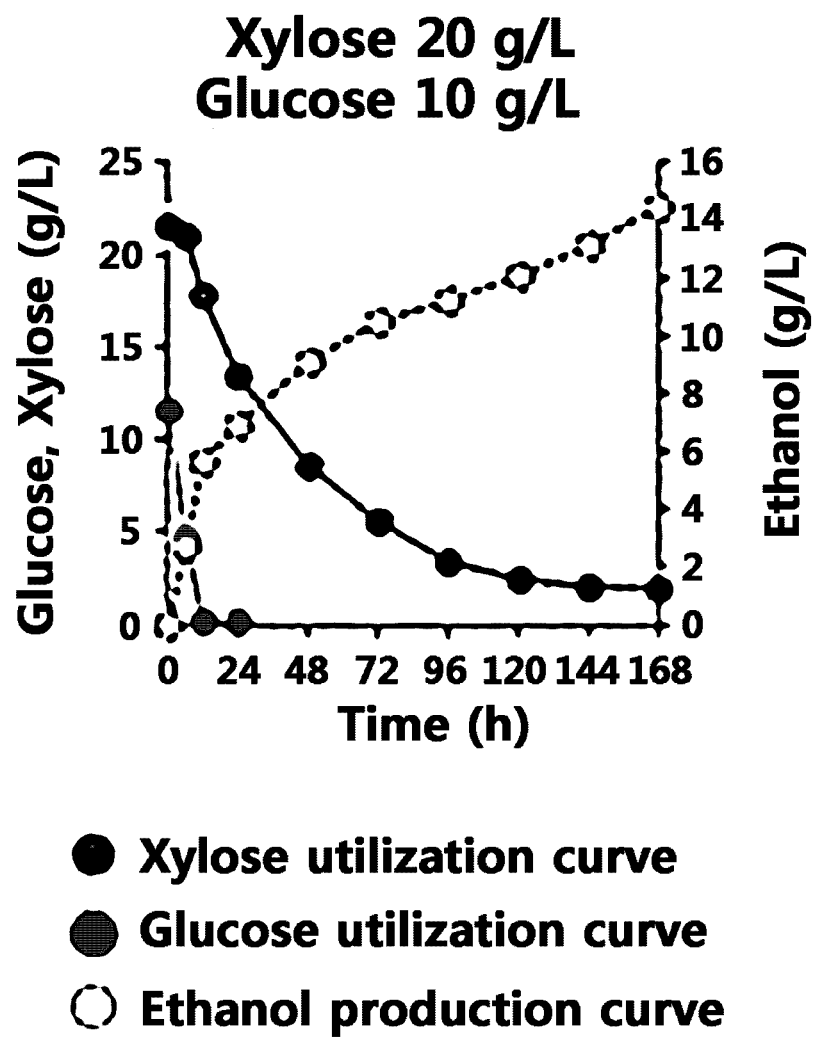
FIG. 4B is a diagram showing xylose utilization curves representing mixed sugar (glucose/xylose) utilization capacity when the transformed strain (XUSE; Example 1) according to an exemplary embodiment of the present invention was cultured in the presence of both xylose and glucose.
Figure 4C:
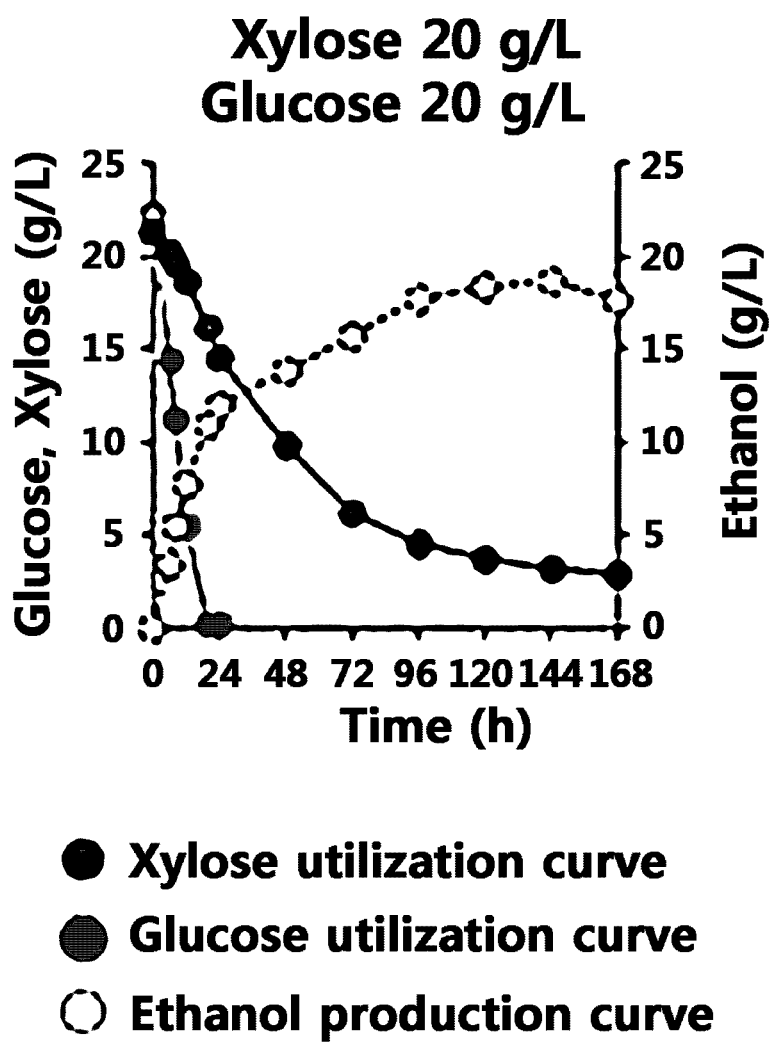
FIG. 4C is a diagram showing ethanol production curves representing mixed sugar (glucose/xylose) utilization capacity when the transformed strain (XUSE; Example 1) according to an exemplary embodiment of the present invention was cultured in the presence of both xylose and glucose.

Most of strains that have been reported to utilize xylose tend to consume all glucose first and then sequentially utilize xylose in an environment where glucose and xylose are simultaneously present, thereby causing a problem of reduced conversion efficiency of lignocellulosic biomass-derived glucose/xylose. As shown in FIGS. 4A to 4C, however, it can be confirmed that the transformed yeast strain according to an exemplary embodiment of the present invention utilizes xylose to produce ethanol even in the presence of glucose, that is simultaneous co-fermentation of mixed sugars. Particularly when glucose is present as the same amount as xylose, xylose utilization capacity is maintained high without inhibition of the glucose, thereby achieving an improved mixed sugar (glucose/xylose) conversion yield compared to existing technology.

Test Example 4

The following experiment was carried out to determine whether the transformed yeast strain according to the present invention can be easily transformed into a strain producing biofuels other than bioethanol.

A modified strain having butanol productivity (Example 6) was prepared by introducing the 1-butanol biosynthetic pathway-constituting genes in the XUSE strain (Example 1) prepared in the above Example. The genes constituting a butanol biosynthetic pathway comprising β-hydroxybutyryl-CoA dehydrogenase (Hbd; SEQ ID NO: 17), 3-hydroxybutyryl-CoA dehydratase (Crt; SEQ ID NO: 18) and butanol dehydrogenase (BdhB; SEQ ID NO: 19), which are derived from *Clostridium acetobutyricum*; acetoacetyl-CoA thiolase (Erg10; SEQ ID NO: 20) and enoyl thioester reductase (Etr1; SEQ ID NO: 21), which are derived from *Saccharomyces cerevisiae*, and butyraldehyde dehydrogenase (EutE; SEQ ID NO: 22), which is derived from *Escherichia coli*. The genes were introduced in the following three forms through a transformation method:

p423-GPDp-CaHbd-PRM9t-TEF1p-CaCrt-CPS1t (SEQ ID NO: 23)

p426-PGKp-EcEute-CYC1t-CYC1p-CaBdhb-SPG5t (SEQ ID NO: 24)

p425-HXT7p-SccytoEtr1-TPI7t-TEF1p-ScErg10-CYC1t) (SEQ ID NO: 25)

As a comparative example of the present invention, the genes of SEQ ID NOS: 23 to 25 constituting the 1-butanol biosynthetic pathway were introduced in BY4741 (Accession No.: ATCC 201388), the wild-type *Saccharomyces cerevisiae* yeast strain as well.

Each of the XUSE modified strain of the present invention, in which the butanol biosynthetic pathway-constituting genes are introduced (Example 6), and the wild-type strain was cultured by inoculating in a minimal medium (YSC medium) containing glucose, that containing xylose, or that containing glucose and xylose as mixed sugars, respectively, and stirring at 30° C. at 200 rpm and observed with respect to the 1-butanol production in the culture after 96 hours.

Figure 5:
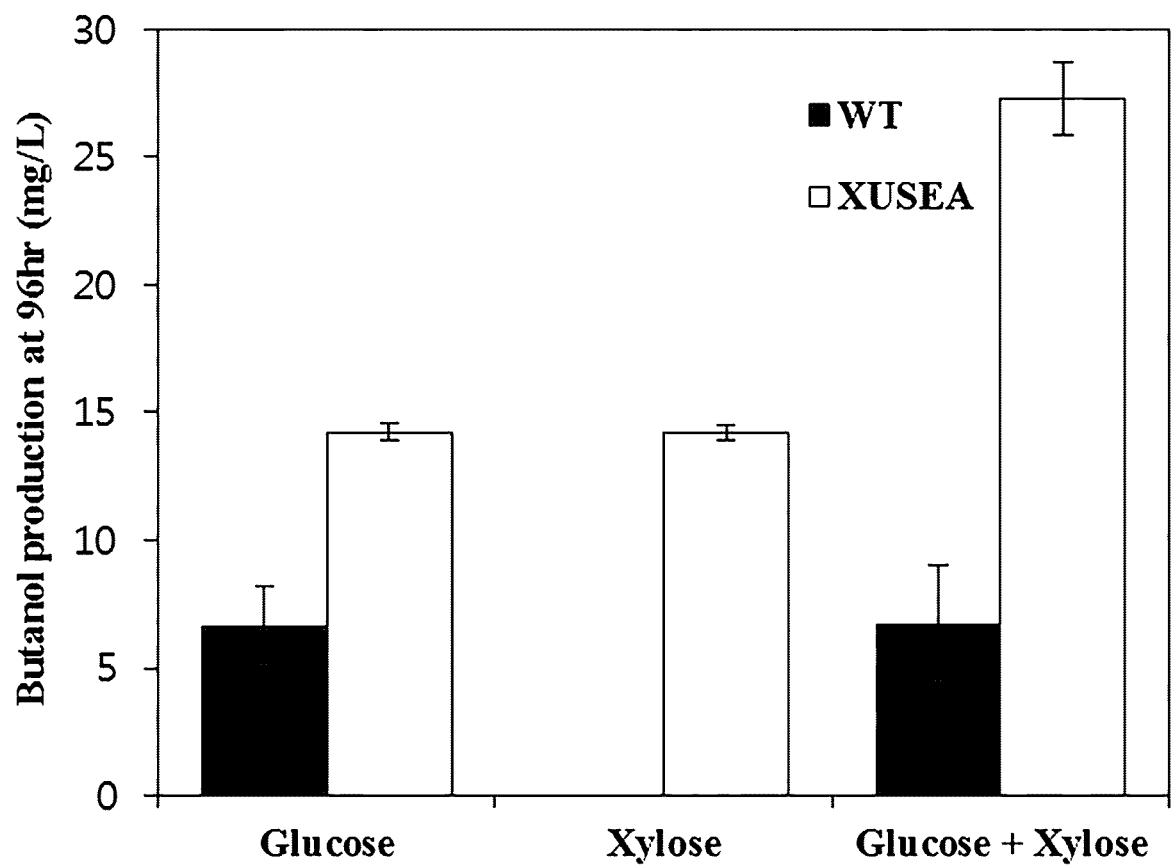
FIG. 5 is a diagram showing the butanol productivity when the modified strain prepared by introducing the butanol biosynthetic pathway in the transformed strain (XUSE A) according to an exemplary embodiment of the present invention (Example 6) was cultured in the presence of glucose or xylose only or both xylose and glucose (glucose+xylose), compared to the wild-type *Saccharomyces cerevisiae* strain (WT).

As shown in FIG. 5, the result showed that the wild-type strain (WT) did not produce 1-butanol at all when xylose was used as a sole carbon source, whereas the XUSE modified strain (Example 6) produced about 14.2 mg/L 1-butanol. Under the condition where both glucose and xylose are simultaneously present, it was confirmed that the XUSE modified strain of the present invention (Example 6) produced about 4 times greater amount of 1-butanol (27.3 mg/L) compared to the WT. This result indicates that the transformed yeast strain according to the present invention can be easily transformed into a strain producing other biofuels such as 1-butanol through a simple additional modification such as introducing a gene having a biosynthetic pathway of another biofuel and has excellent productivity thereof.

According to the present invention, a wild-type yeast strain incapable of utilizing xylose as a carbon source is transformed to be provided with xylose isomerase-based xylose metabolism capacity and is applied with an evolution method to enhance xylose utilization capacity. The present invention does not involve an introduction of an oxidoreductase-based xylose metabolic pathway, and thus can produce ethanol at high yield by co-converting glucose and xylose without causing a problem of cofactor imbalance. The transformed yeast strain according to the present invention can be easily transformed to a strain producing high yield of biofuels/materials through additional modifications, and thus can produce not only bioethanol but also other biofuels or biomaterials such as butanol without an additional process. Therefore, the economics and sustainability of the biofuel and biomaterial production processes can be highly enhanced.

While the present invention has been described with respect to the specific embodiments, it will be apparent to those skilled in the art that various changes and modifications may be made without departing from the spirit and scope of the invention as defined in the following claims.

What is claimed is:

1. A transformed yeast strain of *Saccharomyces cerevisiae*, comprising
   at least one of a mutant of SEQ NO: 1 (PMR1) and a mutant of SEQ ID NO: 3 (ASC1); and
   a gene encoding a xylose isomerase; and at least one of a gene encoding a xylulokinase and a gene encoding a transaldolase,
   wherein the mutant of SEQ ID NO: 1 (PMR1) is SEQ ID NO: 2 (PMR1$^{G681A}$); and
   wherein the mutant of SEQ ID NO: 3 (ASC1) is SEQ ID NO: 4 (ASC1$^{Q237*}$);
   wherein the gene encoding the xylose isomerase is SEQ ID NO: 5 (xylA3*), SEQ ID NO: 6 (xylA), SEQ ID NO: 7 (xylA), or SEQ ID NO: 8 (xylA);
   wherein the gene encoding the xylulokinase is SEQ ID NO: 9 (XKS1) or SEQ ID NO: 10 (xyl3); and
   wherein the gene encoding the transaldolase is SEQ ID NO: 11 (TAL1) or SEQ ID NO: 12 (tal1).

2. The transformed yeast strain of claim 1, wherein at least one of an aldose reductase-encoding gene and a phosphatase-encoding gene is deleted.

3. The transformed yeast strain of claim 1, wherein a parent strain of the transformed *Saccharomyces cerevisiae* is a wild type *Saccharomyces cerevisiae* yeast strain.

4. The transformed yeast strain of claim 3, wherein the wild type *Saccharomyces cerevisiae* yeast strain is ATCC 201388.

5. The transformed yeast strain of claim 2,
   wherein the gene encoding the aldose reductase is SEQ ID NO: 13 (GRE3); and/or
   wherein the gene encoding the phosphatase is SEQ ID NO: 14 (PHO13).

6. The transformed yeast strain of claim 1, wherein the transformed yeast strain is Accession No.KCTC13614BP.

7. The transformed yeast strain of claim 1, wherein the transformed yeast strain simultaneously ferments glucose and xylose to convert into ethanol.

8. The transformed yeast strain of claim 1, further comprising genes constituting a butanol biosynthetic pathway comprising of SEQ ID NO: 17 (β-hydroxybutyryl-CoA dehydrogenase, Hbd), SEQ ID NO: 18 (3-hydroxybutyryl-CoA dehydratase, Crt), SEQ ID NO: 19 (butanol dehydrogenase, BdhB), SEQ ID NO: 20 (acetoacetyl-CoA thiolase, Erg10), SEQ ID NO: 21 (enoyl thioester reductase, Etr1), and SEQ ID NO: 22 (butyraldehyde dehydrogenase, EutE).

9. The transformed yeast strain of claim 8, wherein the butanol biosynthetic pathway-constituting genes are introduced in the form of being inserted in a genomic DNA or in the form of a plasmid.

10. The transformed yeast strain of claim 9, wherein a plasmid of SEQ ID NO: 23, a plasmid of SEQ ID NO: 24 and a plasmid of SEQ ID NO: 25 are introduced.

11. A method for preparing the transformed yeast strain according to claim 1, comprising:
    inserting the gene encoding xylose isomerase; and at least one of the gene encoding xylulokinase and the gene encoding transaldolase; and
    performing at least one of a mutation of SEQ ID NO: 1 (PMR1) and a mutation of SEQ ID NO: 3 (ASC1), while having *Saccharomyces cerevisiae* as a parent strain.

12. The method of claim 11, further comprising deleting at least one of an aldose reductase-encoding gene and a phosphatase-encoding gene.

13. The method of claim 11, wherein the mutation of PMR1 or ASC1 comprises adaptive evolution by subculturing the strain in a minimal medium comprising xylose as a sole carbon source.

14. The method of claim 11, wherein the insertion of gene is carried out using CRISPR/Cas9.

15. The method of claim 11, further comprising introducing genes constituting a butanol biosynthetic pathway comprising β-hydroxybutyryl-CoA dehydrogenase (Hbd), 3-hydroxybutyryl-CoA dehydratase (Crt), butanol dehydrogenase (BdhB), acetoacetyl-CoA thiolase (Erg10), enoyl thioester reductase (Etr1), and butyraldehyde dehydrogenase (EutE).

16. The method of claim 15, wherein the introduction of the butanol biosynthetic pathway-constituting genes comprises introducing the butanol biosynthetic pathway-constituting genes in the form of a plasmid or in the form of being inserted into a genomic DNA.

17. The method of claim 16, wherein the introduction of the butanol biosynthetic pathway-constituting genes comprises introducing a plasmid of SEQ ID NO: 23, a plasmid of SEQ ID NO: 24 and a plasmid of SEQ ID NO: 25.

18. A method for producing a biofuel and biomaterial, comprising fermenting the transformed yeast strain according to claim 1 by culturing the transformed yeast strain in a medium comprising xylose as a sole carbon source or a medium comprising glucose and xylose as carbon sources.

19. The method of claim 18, wherein the biofuel includes ethanol.

* * * * *